United States Patent
Van Delft et al.

(10) Patent No.: US 10,266,502 B2
(45) Date of Patent: Apr. 23, 2019

(54) PROCESS FOR THE CYCLOADDITION OF A HALOGENATED 1,3-DIPOLE COMPOUND WITH A (HETERO)CYCLOALKYNE

(71) Applicant: SynAffix B.V., Oss (NL)

(72) Inventors: Floris Louis Van Delft, Nijmegen (NL); Remon Van Geel, Lith-Oijen (NL); Maria Antonia Wijdeven, Lent (NL); Ryan Heesbeen, Nijmegen (NL)

(73) Assignee: SYNAFFIX B.V., Oss (NL)

( * ) Notice: Subject to any disclaimer, the term of this patent is extended or adjusted under 35 U.S.C. 154(b) by 0 days.

(21) Appl. No.: 15/113,751

(22) PCT Filed: Jan. 26, 2015

(86) PCT No.: PCT/NL2015/050047
§ 371 (c)(1),
(2) Date: Jul. 22, 2016

(87) PCT Pub. No.: WO2015/112016
PCT Pub. Date: Jul. 30, 2015

(65) Prior Publication Data
US 2017/0008858 A1      Jan. 12, 2017

(30) Foreign Application Priority Data
Jan. 24, 2014  (EP) .................................... 14152500

(51) Int. Cl.
| | | |
|---|---|---|
| C07D 249/16 | (2006.01) |
| C07C 247/04 | (2006.01) |
| C07H 19/10 | (2006.01) |
| C07C 247/18 | (2006.01) |
| C07C 247/12 | (2006.01) |
| C07H 1/00 | (2006.01) |
| C07H 13/12 | (2006.01) |
| C07D 225/02 | (2006.01) |
| C07H 19/00 | (2006.01) |
| C07H 13/00 | (2006.01) |
| C07D 321/12 | (2006.01) |
| C07D 225/08 | (2006.01) |
| C07K 16/32 | (2006.01) |

(52) U.S. Cl.
CPC .......... *C07D 249/16* (2013.01); *C07C 247/04* (2013.01); *C07C 247/12* (2013.01); *C07C 247/18* (2013.01); *C07D 225/02* (2013.01); *C07D 225/08* (2013.01); *C07D 321/12* (2013.01); *C07H 1/00* (2013.01); *C07H 13/00* (2013.01); *C07H 13/12* (2013.01); *C07H 19/00* (2013.01); *C07H 19/10* (2013.01); *C07K 16/32* (2013.01); *C07K 2317/24* (2013.01)

(58) Field of Classification Search
CPC .. C07D 249/16; C07D 321/12; C07D 225/08; C07D 225/02; C07C 247/04; C07C 247/18; C07C 247/12; C07H 1/00; C07H 19/00; C07H 19/10; C07H 13/00; C07H 13/12
See application file for complete search history.

(56) References Cited

U.S. PATENT DOCUMENTS

2013/0011901 A1   1/2013 Hosoya et al.

FOREIGN PATENT DOCUMENTS

| JP | 2005-314382 A | 11/2005 |
|---|---|---|
| WO | WO-03/031464 A2 | 4/2003 |
| WO | WO-2005/063784 A1 | 7/2005 |
| WO | WO-2006/035057 A1 | 4/2006 |
| WO | WO-2006/102717 A1 | 10/2006 |
| WO | WO-2007/081031 A1 | 7/2007 |
| WO | WO-2007/095506 A1 | 8/2007 |
| WO | WO-2008/029281 A2 | 3/2008 |
| WO | WO-2008/071672 A2 | 6/2008 |
| WO | WO-2010/125065 A2 | 11/2010 |
| WO | WO-2012/047663 A2 | 4/2012 |
| WO | WO-2013/013244 A2 | 1/2013 |
| WO | WO-2013/036748 A1 | 3/2013 |
| WO | WO-2013/132268 A1 | 9/2013 |
| WO | WO-2013/151697 A1 | 10/2013 |
| WO | WO-2014/065661 A1 | 5/2014 |

OTHER PUBLICATIONS

Banert et al., Tetrahedron Letters, 2010, 51, p. 2880-2882. (Year: 2010).*

(Continued)

*Primary Examiner* — Jonathan S Lau
(74) *Attorney, Agent, or Firm* — Gilberto M. Villacorta; Sunit Talapatra; Foley & Lardner LLP

(57) ABSTRACT

The present invention relates to a cycloaddition process comprising the step of reacting a halogenated aliphatic 1,3-dipole compound with a (hetero)cycloalkyne according to Formula (1): Preferably, the (hetero)cycloalkyne according to Formula (1) is a (hetero)cyclooctyne. The invention also relates to the cycloaddition products obtainable by the process according to the invention. The invention further relates to halogenated aliphatic 1,3-dipole compounds, in particular to halogenated aliphatic 1,3-dipole compounds comprising N-acetylgalactosamine-UDP (GalNAc-UDP), and to halogenated 1,3-dipole compounds comprising (peracylated) N-acetylglucosamine (GlcNAc), N-acetylgalactosamine (GalNAc), N-acetylmannosamine (ManNAc) and N-acetyl neuraminic acid (NeuNAc).

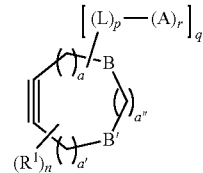

(1)

15 Claims, 9 Drawing Sheets

(56) References Cited

OTHER PUBLICATIONS

Whisstock et al., "Prediction of protein function from protein sequence and structure", Quarterly Reviews of Biophysics, 2003, vol. 36, No. 3, pp. 307-340.
Beal et al., "Click-enabled heterotrifunctional template for sequential bioconjugations" Organic & Biomolecular Chemistry, 2012, vol. 10, pp. 548-554.
Dommerholt et al., "Readily accessible bicylononynes for bioorthogonal labeling and three-dimensional imaging of living cells", Angew. Chem. Int. Ed., 2010, vol. 49, pp. 9422-9425.
Gordon et al., "Reactivity of biarylazacyclooctynones in copper-free click chemistry", Journal of the American Chemical Society, 2012, vol. 134, pp. 9199-9208.
Jayaprakash et al., "Non-nucleoside building blocks for copper-assisted and copper-free click chemistry for the efficient synthesis of RNA conjugates", Organic Letters, 2010, vol. 12, No. 23, pp. 5410-5413.
Knorre et al., "Photoactivatable analogues of the initiating substrates of RNA polymerase II based on aryl azide derivatives of NTP Y-Amidophosphate: synthesis and chemical and photochemical reactions of functional groups", Russian Journal of Bioorganic Chemistry, 2005, vol. 31, No. 4, pp. 332-343.
Manova et al., "Copper-free click biofunctionalization of silicon nitride surfaces via strain-promoted alkyne-azide cycloadditions reactions", Langmuir, 2012, vol. 28, pp. 8651-8663.
Plougastel et al., "4-Halogeno-sydnones for fast strain promotes cycloaddition with bicycle-[6.1.0]-nonyne", Chemical Communications, 2014, vol. 50, pp. 9376-9378.
Qasba et al., "Site-specific linking of biomolecules via glycan residues using glycosyltransferases", Biotechnology Progress, 2008, vol. 24, pp. 520-526.
Temming et al., "N-terminal dual protein functionalization by strain-promoted alkyne-nitrone cycloaddition" Organic & Biomolecular Chemistry, 2013, vol. 11, pp. 2772-2779.
Trinidade et al., "'Click and go': simple and fast folic acid conjugation", Organic & Biomolecular Chemistry, 2014, vol. 12, pp. 1381-3190.
Wallace et al., "Strain-promoted sydnone bicycle-[6.1.0]-nonyne cycloaddition", Chemical Science, 2014, vol. 5, pp. 1742-1744.
International Search Report issued in International Patent Application No. PCT/NL2015/050047, dated Mar. 19, 2015.
Bertozzi et al,. "Second-generation difluorinated cyclooctynes for copper-free click chemistry", J Am Chem Soc, 2008, vol. 130, pp. 11486-11493.
Bertozzi et al., "A hydrophilic azacyclooctyne for cu-free click chemistry", Org. Lett., Jun. 2008, vol. 10, No. 14, pp. 3097-3099.
Bertozzi et al., "A strain-promoted [3 2] azide-alkyne cycloaddition for covalent modification of biomolecules in living systems", J Am Chem Soc, 2004, vol. 126, pp. 15046-15047.
Bertozzi et al., "Copper-free click chemistry for dynamic in vivo imaging", PNAS, Oct. 2007, vol. 104, No. 43, pp. 16793-16797.
Boeggeman et al., "Site specific conjugation of fluoroprobes to the remodeled Fc N-Glycans of monoclonal antibodies using mutant glycosyltransferases: Application for cell surface antigen detection", Bioconjugate Chemistry, 2009, vol. 20, pp. 1228-1236.
Boons et al., "Polar dibenzocyclooctynes for selective labeling of extracellular glycoconjugates of living cells", Journal of the American Chemical Society, 2012, vol. 134, pp. 5381-5389.
Elling et al., "Chemoenzymatic synthesis of biotinylated nucleotide sugars as substrates for glyosyltransferases", ChemBioChem, 2001, vol. 2, pp. 884-894.
Etoc et al., "Subcellular control of Rac-GTPase signalling by magnetogenetic manipulation inside living cells", Nature Nanotechnology, Mar. 2013, vol. 8, pp. 193-198.
Fang et al., "The mechanism of action of ramoplanin and enduracidin", Molecular Biosytems, 2006, vol. 2, pp. 69-76.
Fleet et al., "Affinity labeling of antibodies with aryl nitrene as reactive group", Nature, Nov. 1969, vol. 224, pp. 511-512.
Friscourt et al., "A fluorogenic probe for the catalyst-free detection of azide-tagged molecules", Journal of the American Chemical Society, 2012, vol. 134, pp. 18809-18815.
Grenouillat et al., "Simple synthesis of nodulation-factor analogues exhibiting high affinity towards a specific binding protein", Angew. Chem. Int. Ed., 2004, vol. 43, pp. 4644-4646.
Gross et al., "Discovery of O-GlcNAc transferase inhibitors", Journal of the American Chemical Society, 2005, vol. 127, pp. 14588-14589.
Guan et al., "Highly efficient synthesis of UDP-GalNAc/GlcNAc analogues with promiscuous recombinant human UDP-GalNAc pyrophosphorylase AGX1", Chemistry—A European Journal, 2010, vol. 16, pp. 13343-13345.
Hospital et al., "Access to functionalised silver(I) and gold(I) N-heterocyclic carbenes by [2 3] dipolar cycloadditions", Dalton Transactions, 2012, vol. 41, pp. 6803-6812.
International Search Report issued in International Patent Application No. PCT/NL2015/050044, dated May 27, 2015.
International Search Report issued in International Patent Application No. PCT/NL2015/050045, dated Mar. 19, 2015.
Jawalekar et al., "Synthesis of isoxazoles by hypervalent iodine-induced cycloaddition of nitrile oxides to alkynes", Chemical Communications, 2011, vol. 47, pp. 3198-3200.
Leeper et al., "Development and evaluation of new cyclooctynes for cell surface glycan imaging in cancer cells", Chemical Science, 2011, vol. 2, pp. 932-936.
Lisse et al., "Monofunctional stealth nanoparticle for unbiased single molecule tracking inside living cells", Nano Letters, 2014, vol. 14, pp. 2189-2195.
Liu et al., "Perfluorophenyl azides: new appplications in surface functionalization and nanomaterial synthesis", Acc Chem Res., Nov. 2010, vol. 43, No. 11, pp. 1434-1443.
Masuko et al., "Chemoenzymatic synthesis of uridine disphosphate-GlcNAc and Uridine Diphosphate-GalNAc analogs for the preparation of unnatural glycosaminoglycans", The Journal of Organic Chemistry, 2012, vol. 77, pp. 1449-1456.
McKay et al., "Kinetics studies of rapid strain-promoted [3 2]-cycloadditions of nitrones with biaryl-aza-cyclooctynone", Organic & Biomolecular Chemistry, 2012, vol. 10, pp. 3066-3070.
McKay et al., "Nitrones as dipoles for rapid strain-promoted 1,3-dipolar cycloadditions with cyclooctynes", Chemical Communications, 2010, vol. 46, No. 6, pp. 931-933.
Mercer et al., "Use of novel mutant Galactosyltransferase for the bioconjugation of terminal N-Acetylglucosamine (GlcNAc) residues on live cell surface", Bioconjugate Chemistry, 2013, vol. 24, pp. 144-152.
Pannecoucke et al., "6-Azido D-galactose transfer to N-acetyl-D-glucosamine derivative using commercially available B-1,4-galactosyltransferase", Tetrahedron Letters, 2008, vol. 49, pp. 2294-2297.
Qasba et al., "Structure-based design of B1,4-galactosyltransferase I (B4Gal-T1) with equally efficient N-Acetylgalactosaminyltransferase activity", The Journal of Biological Chemistry, Jun. 7, 2002, vol. 277, No. 23, pp. 20833-20839.
Sanders et al., "Metal-free sequential [3+2]-dipolar cycloadditions using cyclooctynes and 1,3-dipoles of different reactivity", Journal of the American Chemical Society, 2011, vol. 133, pp. 949-957.
Shieh et al., "Imaging bacterial peptidoglycan with near-infrared fluorogenic azide probes", PNAS, Apr. 15, 2014, vol. 111, No. 5, pp. 5456-5461.
Singh et al., "Fast RNA conjugations on solid phase by strain-promoted cycloadditions", Organic & Biomolecular Chemistry, 2012, vol. 10, pp. 6633-6639.
Tummatorn et al., "Strain-promotes azide-alkyne cycloadditions of benzocyclononynes", The Journal of Organic Chemistry, 2012, vol. 77, pp. 2093-2097.
Van Delft et al., "Bioconjugation with strained alkenes and alkynes", Accounts of Chemical Research, 2011, vol. 44, No. 9, pp. 805-815.
Welle et al., "Tri- and tetravalent photoactivable cross-linking agents", Synthesis, 2012, vol. 44, pp. 2249-2254.
Xie et al., 1,3-dipolar cycloadditon reactivities of perfluorinated aryl azides with enamines and strained dipolarophiles, The Journal of the American Chemical Society, 2015, vol. 137, pp. 2958-2966.

(56) References Cited

OTHER PUBLICATIONS

Zlatopolskiy et al., "Beyond azide-alkyne click reaction: easy access to F-labelled compounds via nitrile oxide cycloadditions", Chemical Communications, 2012, vol. 48, pp. 7134-7136.
Zou et al., "One-pot three-enzyme synthesis of UDP-Glc, UDP-Gal, and their derivatives", Carbohydrate Research, 2013, vol. 373, pp. 76-81.
U.S. Appl. No. 15/113,740, US2017-0009266 A1.
U.S. Appl. No. 15/113,730, US2017-0002012 A1.

* cited by examiner

41

43

42

44

PROCESS FOR THE CYCLOADDITION OF A HALOGENATED 1,3-DIPOLE COMPOUND WITH A (HETERO)CYCLOALKYNE

CROSS-REFERENCE TO RELATED APPLICATIONS

This application is the National Phase of International Patent Application No. PCT/NL2015/050047, filed Jan. 26, 2015, published on Jul. 30, 2015 as WO 2015/112016 A1, which claims priority to European Patent Application No. 14152500.6, filed Jan. 24, 2014. The contents of these applications are herein incorporated by reference in their entirety.

FIELD OF THE INVENTION

The present invention is in the field of 1,3-dipolar cycloaddition reactions. The invention relates to a process for the 1,3-dipolar cycloaddition of a halogenated 1,3-dipole compound with a (hetero)cycloalkyne, preferably a (hetero)cyclooctyne.

BACKGROUND OF THE INVENTION

A 1,3-dipolar cycloaddition, also called Huisgen (3+2) cycloaddition, is a chemical reaction between a 1,3-dipole and a dipolarophile to form a five-membered ring. Typical dipoles that are used in (3+2) cycloaddition reactions involve azides, nitrones, nitrile oxides and diazo compounds, to react with alkynes or alkenes as dipolarophile, leading to five-membered heterocycles. Typical conditions for Huisgen cycloaddition involve the prolonged heating of starting components. However, cycloaddition can also be induced by means of addition of a metal catalyst or by means of the use of a strained alkene or alkyne.

Strain-promoted azide-alkyne cycloaddition (SPAAC) involves the formation of a 1,2,3-triazole by reaction of an azide with a strained, cyclic alkyne. Apart from azides, strained alkynes also show high reactivity with other dipoles, such as nitrones and nitrile oxides. For example, the strain-promoted alkyne-nitrone cycloaddition (SPANC) was applied for the N-terminal modification of proteins.

SPAAC and SPANC cycloaddition reactions proceed spontaneously, hence in the absence of a (metal) catalyst, and these and a select number of additional cycloadditions are also referred to as "metal-free click reactions".

Original reports on the reaction of phenyl azide with cyclooctyne date back more than 50 years, but it was not until 2004 that the practical use of SPAAC was recognized for the functional connection of two molecular entities, connected to azide or cyclooctyne, respectively. For example, Bertozzi et al. have demonstrated in *J. Am. Chem. Soc.* 2004, 126, 15046 (incorporated by reference) that incubation of Jurkat cells with azide-functionalized mannosamine led to effective exposure of azide on the cell surface, as visualized by treatment with cyclooctyne-conjugated biotin, then staining with FITC-avidin and flow cytometry. However, it was also found that the reaction rate of plain cyclooctyne with azide was relatively low, for example less effective than similar staining of azide-labeled cells with copper-catalyzed cycloaddition of azide with a biotinylated terminal alkyne (CuAAC) or with a phosphine reagent (Staudinger ligation). As a consequence, in subsequent years much attention has been focused on the development of cyclooctynes with superior reaction rates, for example difluorocyclooctyne (DIFO), dibenzocyclooctynol (DIBO), dibenzoazacyclooctyne (DIBAC/DBCO), bisarylazacyclooctynone (BARAC), bicyclo[6.1.0]nonyne (BCN) and carboxymethylmonobenzocyclooctyne (COMBO). Of these, the most frequently applied cyclooctynes are DIBO, DIBAC/DBCO and BCN, all of which are commercially available and display high reactivity in cycloadditions not only with azides, but also with other 1,3-dipoles such as nitrones, nitrile oxides and diazo compounds.

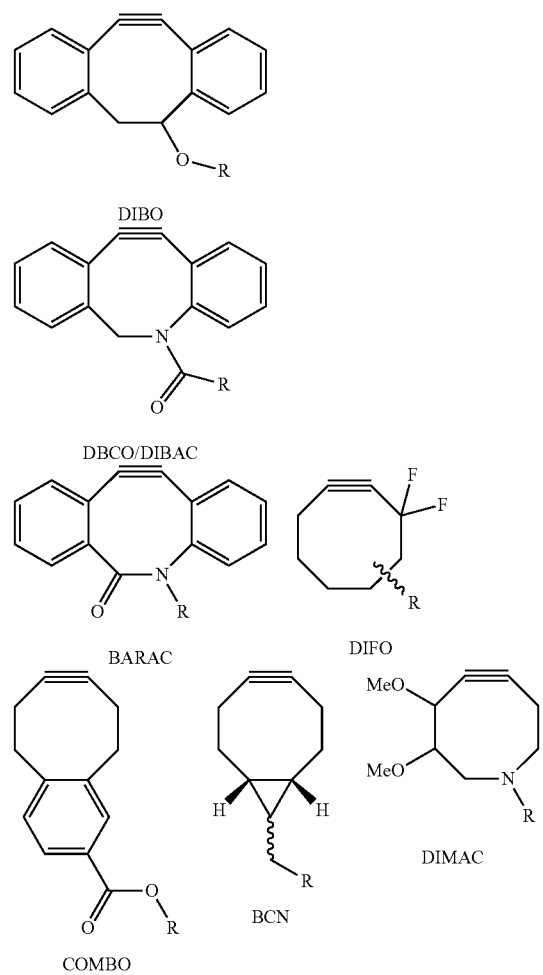

An example of a cyclononyne is the benzocyclononyne shown below, disclosed by Tummatorn et al., *J. Org. Chem.* 2012, 77, 2093, incorporated by reference.

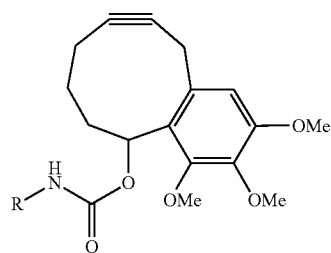

The ease of operation of SPAAC and the high stability of the resulting triazole functionality have led to a wide range of applications, including in vitro and in vivo labeling, patterning of solid surfaces, formation of bioconjugates from proteins, nucleic acid and glycans, medical applications etc. Two prime parameters that determine the choice of cyclooctyne for a particular application are lipophilicity and reaction rate. Since the vast majority of cyclooctynes exist predominantly of hydrocarbon, they are typically hydrophobic and hence poorly water-soluble. To enhance water-solubility, Bertozzi et al. developed dimethoxy-azacyclooctyne (DIMAC) from a carbohydrate precursor, as reported in *Org. Lett.* 2008, 10, 3097 (incorporated by reference), but the increase in polarity was accompanied by attenuated reactivity. Two successful strategies to enhance water-solubility of a benzoannulated cyclooctyne, as was demonstrated for derivatization of DIBO, are by aromatic sulfonation (Boons et al., 2012, 134, 5381, incorporated by reference) or by tetramethoxy-substitution (Leeper et al. 2011, 2, 932, incorporated by reference). However, it is also clear that from a steric perspective it is more desirable to avoid the presence of a (bulky) substituent in a cyclooctyne altogether. Thus, the desire to optimize hand-in-hand polarity and reactivity of cyclooctynes is still driving research for further improvement.

In a recent report, Bertozzi et al. in *J. Am. Chem. Soc.* 2012, 134, 9199, incorporated by reference, explicitly mention that BARAC reacts with azide faster than any other reported cyclooctyne, thereby underlining the general perception that reaction rate of cyclooctynes is not influenced by azide substituents (aliphatic or aromatic or substituted versions).

A halogenated aryl azide with particular application in the field of labeling is 4-azido-2,3,5,6-tetrafluorobenzoic acid ($N_3$-TFBA). Originally introduced by Fleet et al. in *Nature* 1969, 224, 511, incorporated by reference, aryl azides have become popular precursors of nitrenes as versatile photoaffinity labeling agents. Upon photolysis, $N_2$ is liberated and a highly unstable singlet phenylnitrene is formed in situ, which reacts with neighbouring molecules in a variety of reactions. Perfluorophenyl azides are of particular interest in the field of photoaffinity labeling because highly stabilized nitrene intermediates are formed that undergo insertion and addition reaction in moderate to good yields rather than intermolecular rearrangements. For this purpose, a variety of derivatives of 4-azido-2,3,5,6-tetrafluorobenzoic acid ($N_3$-TFBA) are commercially available and have been applied for labeling of biomolecules, polymers, small molecules, carbon materials, gold/silver, metal oxides and silicate/semiconductors, as inter alia reviewed in Liu et al. *Acc. Chem. Res.* 2011, 43, 1434 and Welle et al. *Synthesis* 2012, 44, 2249, both incorporated by reference. However, none of the earlier applications of $N_3$-TFBA mention labeling or conjugation by strain-promoted cycloaddition reaction.

SUMMARY OF THE INVENTION

The present invention relates to a process comprising the step of reacting a halogenated 1,3-dipole compound with a (hetero)cycloalkyne:
wherein a halogenated 1,3-dipole compound is defined as a compound comprising a 1,3-dipole functional group and one or more substituents $R^4$, wherein $R^4$ is independently selected from the group consisting of F, Cl, Br, I and —$C_yR^{13}_{(2y+1)}$ wherein y is 1-6 and $R^{13}$ is independently selected from the group consisting of F, Cl, Br and I; wherein the 1,3-dipole functional group is bonded to an $sp^3$ C-atom, and at least one of the one or more substituents $R^4$ is bonded to that same $sp^3$ C-atom; and wherein the (hetero)cycloalkyne is according to Formula (1):

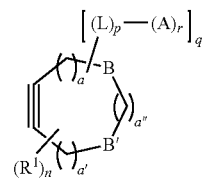

wherein:
a is 0-8;
a' is 0-8;
a" is 0-8;
with the proviso that a+a'+a"=4, 5, 6, 7 or 8;
n is 0-16;
$R^1$ is independently selected from the group consisting of oxo, halogen, —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups; B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when n is 2 or more, two $R^1$ groups may together form a (hetero)aryl group, the (hetero)aryl group optionally being substituted with an $(L)_p$-$(A)_r$ substituent;
p is 0 or 1;
r is 1-4;
L is a linker;
A is independently selected from the group consisting of D, E or Q, wherein D, E and Q are as defined below;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or n is 2 or more and two $R^1$ groups together form a (hetero)aryl group wherein the (hetero)aryl group is substituted with an $(L)_p$-$(A)_r$ substituent;
D is a molecule of interest;
E is a solid surface; and
Q is a functional group.

In particular, the invention relates to a process as defined above, wherein the (hetero)cycloalkyne is a (hetero)cyclooctyne according to Formula (1), wherein a is 0, 1, 2, 3 or 4, a' is 0, 1, 2, 3 or 4 and a" is 0, 1, 2, 3 or 4, with the proviso that a+a'+a"=4, and wherein n is 0-8.

The present invention further relates to a product obtainable by the process according to the invention.

The invention also relates to several halogenated 1,3-dipole compounds, particularly to halogenated 1,3-dipole compounds according to Formula (2d), (2w) (2zc) or (2zd), or their GlcNAc derived diastereoisomers:

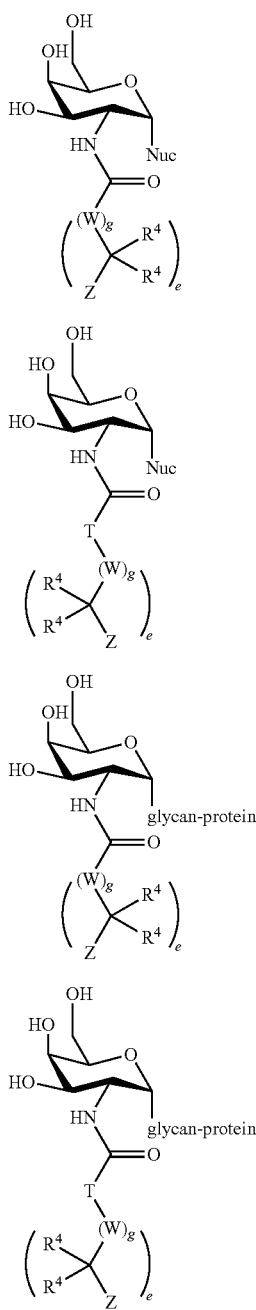

wherein:
Z is a 1,3-dipole functional group;
$R^4$ is independently selected from the group consisting of halogen (F, Cl, Br, I) and $-C_y R^{13}{}_{(2y+1)}$, wherein y is 1-6 and $R^{13}$ is selected from the group consisting of F, Cl, Br and I;
e is 1-10;
g is 0 or 1;

W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl (hetero)arylene groups and (hetero)arylalkylene groups are optionally interrupted by one or more heteroatoms selected from the group consisting of O, S and N;
T is O or NH: and
Nuc is selected from the group consisting of a nucleoside monophosphate and a nucleoside diphosphate.

DETAILED DESCRIPTION OF THE INVENTION

Definitions

Figure 1:
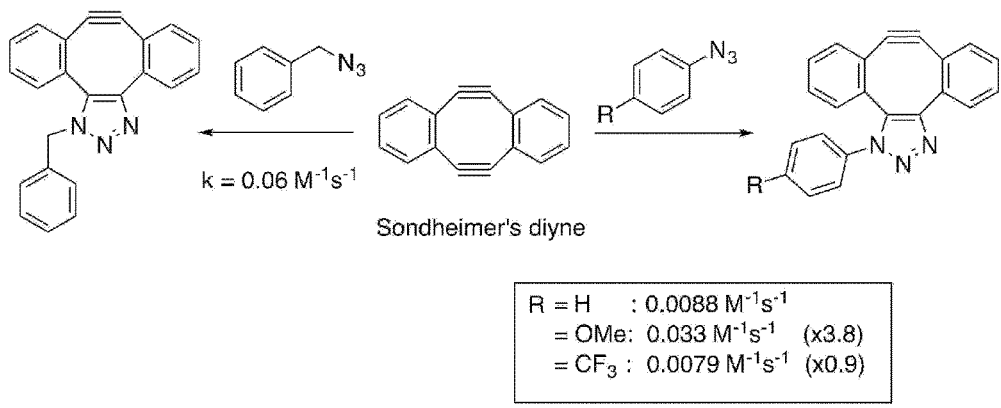
FIG. 1 shows the cycloaddition reaction and reaction rate constants of benzyl azide, phenyl azide, p-MeOPhN$_3$ and p-CF$_3$PhN$_3$ with Sondheimer's diyne (a dibenzoannulated cyclooctyne) in MeOH.

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

Unsubstituted alkyl groups have the general formula $C_nH_{2n+1}$ and may be linear or branched. Optionally, the alkyl groups are substituted by one or more substituents further specified in this document. Examples of alkyl groups include methyl, ethyl, propyl, 2-propyl, t-butyl, 1-hexyl, 1-dodecyl, etc.

Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl and cyclohexyl.

Unsubstituted alkenyl groups have the general formula $C_nH_{2n-1}$, and may be linear or branched. Examples of suitable alkenyl groups include, but are not limited to, ethenyl, propenyl, isopropenyl, butenyl, pentenyl, decenyl, octadecenyl, and eicosenyl and the like. Unsubstituted alkenyl groups may also contain a cyclic moiety, and thus have the concomitant general formula $C_nH_{2n-3}$.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

Unless stated otherwise, alkyl groups, alkenyl groups, alkenes, alkynes, (hetero)aryl groups, (hetero)arylalkyl groups, alkyl(hetero)aryl groups, alkylene groups, alkenylene groups, cycloalkylene groups, (hetero)arylene groups, alkyl(hetero)arylene groups, (hetero)arylalkylene groups, alkenyl groups, alkynyl groups, cycloalkyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, Cl, Br, I), amino groups, oxo and silyl groups, wherein the silyl groups can be represented by the formula $(R^{Si})_3Si—$, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more heteroatoms selected from the group consisting of O, N and S.

An alkynyl group comprises a carbon-carbon triple bond. An unsubstituted alkynyl group comprising one triple bond has the general formula $C_nH_{2n-3}$. A terminal alkynyl is an alkynyl group wherein the triple bond is located at a terminal position of a carbon chain. Optionally, the alkynyl group is substituted by one or more substituents further specified in this document, and/or interrupted by heteroatoms selected from the group of oxygen, nitrogen and sulphur. Examples of alkynyl groups include ethynyl, propynyl, butynyl, octynyl, etc.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

The term "(hetero)aryl group" comprises an aryl group and a heteroaryl group. The term "alkyl(hetero)aryl group" comprises an alkylaryl group and an alkylheteroaryl group. The term "(hetero)arylalkyl group" comprises an arylalkyl group and a heteroarylalkyl group. The term "(hetero)alkynyl group" comprises an alkynyl group and a heteroalkynyl group. The term "(hetero)cycloalkynyl group" comprises an cycloalkynyl group and a heterocycloalkynyl group.

A (hetero)cycloalkyne compound is herein defined as a compound comprising a (hetero)cycloalkynyl group.

Several of the compounds described in this description and in the claims may be described as fused (hetero)cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) or an arene (e.g. benzene) may be annulated to the (hetero)cyclooctynyl group. Unless otherwise stated, the triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). Unless otherwise stated, the description of a fused (hetero)cyclooctyne compound in this description and in the claims is meant to include all three individual regioisomers of the cyclooctyne moiety.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA). Examples of a sugar derivative also include compounds herein denoted $Su(A)_x$, wherein Su is a sugar or a sugar derivative, and wherein Su comprises x functional groups A.

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (*candida antartica* lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan.

A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein.

A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar.

A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The end of an oligosaccharide that is directly attached to the protein is called the reducing end of a glycan. The other end of the oligosaccharide is called the non-reducing end of a glycan.

For O-linked glycans, a wide diversity of chains exist. Naturally occurring O-linked glycans typically feature a serine or threonine-linked α-O-GalNAc moiety, further substituted with galactose, sialic acid and/or fucose. The hydroxylated amino acid that carries the glycan substitution may be part of any amino acid sequence in the protein.

For N-linked glycans, a wide diversity of chains exist. Naturally occurring N-linked glycans typically feature an asparagine-linked β-N-GlcNAc moiety, in turn further substituted at its 4-OH with β-GlcNAc, in turn further substituted at its 4-OH with β-Man, in turn further substituted at its 3-OH and 6-OH with α-Man, leading to the glycan pentasaccharide $Man_3GlcNAc_2$. The core GlcNAc moiety may be further substituted at its 6-OH by α-Fuc. The pentasaccharide $Man_3GlcNAc_2$ is the common oligosaccharide scaffold of nearly all N-linked glycoproteins and may carry a wide variety of other substituents, including but not limited to Man, GlcNAc, Gal and sialic acid. The asparagine that is substituted with the glycan on its side-chain is typically part of the sequence Asn-X-Ser/Thr, with X being any amino acid but proline and Ser/Thr being either serine or threonine.

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, F(ab')$_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Suitable marketed antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

Cycloaddition of a Halogenated 1,3-Dipole Compound with a (Hetero)Cycloalkyne

The present invention discloses a process for the cycloaddition of a halogenated 1,3-dipole compound with a (hetero) cycloalkyne. The cycloaddition of a 1,3-dipole compound with an alkyne is also referred to as a 1,3-dipolar cycloaddition.

In a first aspect, the invention relates to a process comprising the step of reacting a halogenated 1,3-dipole compound with a (hetero)cycloalkyne,
wherein a halogenated 1,3-dipole compound is defined as a compound comprising a 1,3-dipole functional group and one or more substituents $R^4$, wherein $R^4$ is independently selected from the group consisting of F, Cl, Br, I and —$C_yR^{13}_{(2y+1)}$ wherein y is 1-6 and $R^{13}$ is independently selected from the group consisting of F, Cl, Br and I;
wherein the 1,3-dipole functional group is bonded to an sp$^3$ C-atom, and at least one of the one or more substituents $R^4$ is bonded to that same sp$^3$ C-atom;
and wherein the (hetero)cycloalkyne is according to Formula (1):

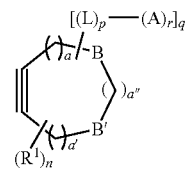

wherein:
a is 0-8;
a' is 0-8;
a" is 0-8;
with the proviso that a+a'+a"=4, 5, 6, 7 or 8;
n is 0-16;
$R^1$ is independently selected from the group consisting of oxo, halogen (F, Cl, Br, I), —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero) aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen (F, Cl, Br, I), $C_1$-$C_{24}$ alkyl groups, $C_3$-$C_{24}$ cycloalkyl groups, $C_2$-$C_{24}$ (hetero)aryl groups, $C_3$-$C_{24}$ alkyl (hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;

optionally, when n is 2 or more, two $R^1$ groups may together form a (hetero)cycloalkyl group, the (hetero)cycloalkyl group optionally being substituted with an $(L)_p$-$(A)_r$ substituent;
optionally, when n is 2 or more, two $R^1$ groups may together form a (hetero)aryl group, the (hetero)aryl group optionally being substituted with an $(L)_p$-$(A)_r$ substituent;
p is 0 or 1;
r is 1-4;
L is a linker;
A is independently selected from the group consisting of D, E or Q, wherein D, E and
Q are as defined below;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or n is 2 or more and two $R^1$ groups together form a (hetero)aryl group wherein the (hetero)aryl group is substituted with an $(L)_p$-$(A)_r$ substituent;
D is a molecule of interest; E is a solid surface; and Q is a functional group;
in order to form to form the cycloaddition product of said halogenated 1,3-dipole compound and (hetero)cycloalkyne.

In particular, the invention relates to a process as defined above, wherein the (hetero)cycloalkyne is a (hetero)cyclooctyne according to Formula (1), wherein a is 0, 1, 2, 3 or 4, a' is 0, 1, 2, 3 or 4 and a" is 0, 1, 2, 3 or 4, with the proviso that a+a'+a"=4, and wherein n is 0-8, in order to form to form the cycloaddition product of said halogenated 1,3-dipole compound and (hetero)cyclooctyne.

The process for the cycloaddition of a halogenated 1,3-dipole compound and a (hetero)cycloalkyne is preferably performed in a suitable solvent, for example dichloromethane, chloroform, THF, Me-THF, ethyl acetate, diethyl ether, DMF, DMA, toluene, benzene, xylene, acetone or hexane. The cycloaddition process may also be performed in water, or a mixture of water and a water miscible solvent (e.g. acetonitrile or THF). Alternatively, the reaction can be performed without any solvent (neat).

The process is preferably performed at a temperature in the range of about −78° C. to about 300° C., more preferably in the range of −40° C. to 200° C., even more preferably in the range of about −20° C. to 100° C., and most preferably in the range of about 0° C. to 60° C.

The process is preferably performed with a stoichiometry of reagents in the range of 10 to 1 (or vice versa), more preferably in the range of 5 to 1, even more preferably in the range of 2 to 1, and most preferably in the range close to 1 to 1.

The process is thus preferably performed with a stoichiometry of reagents in the range of 10:1 to 1:10. More preferably the process is performed with a stoichiometry of reagents in the range of 5:1 to 1:5, even more preferably in the range of 2:1 to 1:2. In one embodiment, when one of the reagents is present in excess, it is preferred that the halogenated 1,3-dipole compound is present in excess, i.e. the process is preferably performed with a ratio of halogenated 1,3-dipole compound to (hetero)cycloalkyne in the range of 10 to 1, more preferably in the range of 5 to 1, even more preferably in the range of 2 to 1. In another embodiment, when one of the reagents is present in excess, it is preferred that the (hetero)cycloalkyne is present in excess, i.e. the process is preferably performed with a ratio of (hetero)cycloalkyne to (halogenated 1,3-dipole compound in the range of 10 to 1, more preferably in the range of 5 to 1, even more preferably in the range of 2 to 1.

Most preferably the process is performed with a stoichiometry of reagents close to 1:1. The halogenated 1,3-dipole compound and the (hetero)cycloalkyne compound, and preferred embodiments thereof, are described in more detail below.

Halogenated 1,3-Dipole Compound

A halogenated 1,3-dipole compound is herein defined as a compound comprising a 1,3-dipole functional group and one or more substituents $R^4$, wherein $R^4$ is independently selected from the group consisting of halogen (F, Cl, Br, I) and $—C_yR^{13}_{(2y+1)}$ wherein y is 1-6 and $R^{13}$ is independently selected from the group consisting of F, Cl, Br and I, and wherein the 1,3-dipole functional group is bonded to an sp$^3$ C-atom, and at least one of the one or more substituents $R^4$ is bonded to that same sp$^3$ C-atom.

When the 1,3-dipole functional group is bonded to an sp$^3$ C-atom, and at least one of the one or more substituents $R^4$ is bonded to that same sp$^3$ C-atom, the halogenated 1,3-dipole compound is herein referred to as a halogenated aliphatic 1,3-dipole compound.

In a halogenated aliphatic 1,3-dipole compound, when $R^4$ is $—C_yR^{13}_{(2y+1)}$, it is preferred that $R^{13}$ is F. Preferably, y is 1, 2, 3 or 4, more preferably y is 1 or 2, and even more preferably y is 1. Preferably, $R^{13}$ is F and y is 1, 2, 3 or 4, more preferably $R^{13}$ is F and y is 1 or 2, and most preferably $R^{13}$ is F and y is 1. In other words, when $R^4$ is $—C_yR^{13}_{(2y+1)}$ it is preferred that $R^4$ is $—C_4F_9$, $—C_3F_7$, $—C_2F_5$ or $—CF_3$, more preferred that $R^4$ is $—C_2F_5$ or $—CF_3$, and most preferred that $R^4$ is $—CF_3$.

In a halogenated aliphatic 1,3-dipole compound, $R^4$ is preferably independently selected from the group consisting of F, Cl, Br and $—C_yR^{13}_{(2y+1)}$, wherein y and $R^{13}$ are as defined above. More preferably, $R^4$ is independently selected from the group consisting of F, Cl, Br, $—C_4F_9$, $—C_3F_7$, $—C_2F_5$ and $—CF_3$. Even more preferably, $R^4$ is independently selected from the group consisting of F, Cl, Br, $—C_2F_5$ and $—CF_3$. Yet even more preferably, $R^4$ is independently selected from the group consisting of F, Cl and $—CF_3$, and even more preferably $R^4$ is selected independently from the group consisting of F and Cl. Most preferably, $R^4$ is F.

In a halogenated aliphatic 1,3-dipole compound it is preferred that two substituents $R^4$ are bonded to the same sp$^3$ C-atom that the 1,3-dipole functional group is bonded to. It is further preferred that the two substituents $R^4$ that are bonded to the same sp$^3$ C-atom as the 1,3-dipole functional group, are identical.

The term "1,3-dipole functional group" herein refers to a group comprising a three-atom π-electron system containing four electrons delocalized over the three atoms. 1,3-Dipole compounds, i.e. compounds comprising a 1,3-dipole functional group, are well known in the art.

In a preferred embodiment of the process according to the invention, the halogenated aliphatic 1,3-dipole compound is selected from the group consisting of a halogenated aliphatic nitrone compound, a halogenated aliphatic azide compound, a halogenated aliphatic diazo compound, a halogenated aliphatic nitrile oxide compound, a halogenated aliphatic nitronate compound, a halogenated aliphatic nitrile imine compound, a halogenated aliphatic sydnone compound, a halogenated aliphatic sulfon hydrazide compound, a halogenated aliphatic pyridine oxide compound, a halogenated aliphatic oxadiazole 1-oxide compound, a halogenated aliphatic dipole resulting from deprotonation of an alkylated pyridinium compound, a halogenated aliphatic [1,2,3]triazol-8-ium-1-ide compound, a halogenated aliphatic 1,2,3-oxadiazol-3-ium-5-olate compound and a halogenated aliphatic 5-oxopyrazolidin-2-ium-1-ide compound.

In a further preferred embodiment of the process according to the invention, the halogenated aliphatic 1,3-dipole compound is selected from the group consisting of a halogenated aliphatic nitrone compound, a halogenated aliphatic azide compound, a halogenated aliphatic diazo compound, a halogenated aliphatic nitrile oxide compound, a halogenated aliphatic nitronate compound, a halogenated aliphatic nitrile imine compound, a halogenated aliphatic sydnone compound, a halogenated aliphatic sulfon hydrazide compound, a halogenated aliphatic pyridine oxide compound and a halogenated aliphatic oxadiazole 1-oxide compound, more preferably from the group consisting of a halogenated aliphatic nitrone compound, a halogenated aliphatic azide compound, a halogenated aliphatic diazo compound and a halogenated aliphatic nitrile oxide compound, and even more preferably from the group consisting of a halogenated aliphatic nitrone compound, a halogenated aliphatic azide compound and a halogenated aliphatic nitrile oxide compound.

Most preferably, the halogenated aliphatic 1,3-dipole compound is a halogenated aliphatic azide compound.

As was described above, in the process according to the invention the halogenated 1,3-dipole compound is a halogenated aliphatic 1,3-dipole compound.

In a preferred embodiment of the process according to the invention, the halogenated aliphatic 1,3-dipole compound is according to Formula (2):

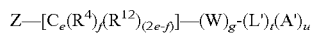   2 wherein:
t is 0 or 1;
u is 1-4;
Z is a 1,3-dipole functional group;
L' is a linker;
A' is independently selected from the group consisting of D, E or Q, wherein D, E and Q are as defined below;
$R^4$ is independently selected from the group consisting of halogen (F, Cl, Br, I) and $-C_yR^{13}_{(2y+1)}$, wherein y is 1-6 and $R^{13}$ is selected from the group consisting of F, Cl, Br and I;
e is 1-10;
f is 1-2e;
g is 0 or 1; and
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl (hetero)arylene groups and (hetero)arylalkylene groups are optionally interrupted by one or more heteroatoms selected from the group consisting of O, S and N.

As defined above, e is 1-10 and f is 1-2e. In other words, when e is 1-10, then f is 1-20. Preferably, e is 1-8 and f is 1-16, more preferably, e is 1-6 and f is 1-12, more preferably, e is 1, 2, 3 or 4 and f is 1, 2, 3, 4, 5, 6, 7 or 8, yet more preferably e is 1, 2 or 3 and f is 1, 2, 3, 4, 5 or 6, 7 and even more preferably, e is 1 or 2 and f is 1, 2, 3 or 4. Most preferably, e is 1 and f is 1 or 2, preferably 2.

Z is a 1,3-dipole functional group. 1,3-Dipole functional groups are described in more detail above. Preferably, Z is selected from the group consisting of a nitrone group, an azide group, a diazo group, a nitrile oxide group, a nitronate group, a nitrile imine group, a sydnone group, a sulfon hydrazide group, a pyridine oxide group, an oxadiazole 1-oxide group, a 1,3-dipole functional group resulting from deprotonation of an alkylated pyridinium compound, a [1,2,3]triazol-8-ium-1-ide group, a 1,2,3-oxadiazol-3-ium-5-olate group and a 5-oxopyrazolidin-2-ium-1-ide group.

More preferably, Z is selected from the group consisting of a nitrone group, an azide group, a diazo group, a nitrile oxide group, a nitronate group, a nitrile imine group, a sydnone group, a sulfon hydrazide group, a pyridine oxide group and a oxadiazole 1-oxide group, more preferably from the group consisting of a nitrone group, an azide group, a diazo group and a nitrile oxide group, and even more preferably from the group consisting of a nitrone group, an azide group and a nitrile oxide group. Most preferably, Z is an azide group.

$R^{12}$ is preferably independently selected from the group consisting of hydrogen and $C_1$-$C_{12}$ alkyl groups, more preferably from the group consisting of hydrogen and $C_1$-$C_6$ alkyl groups, and even more preferably from the group consisting of hydrogen, methyl, ethyl, n-propyl, i-propyl, n-butyl, s-butyl and t-butyl. Most preferably, $R^{12}$ is hydrogen.

When $R^4$ is $-C_yR^{13}_{(2y+1)}$, it is preferred that $R^{13}$ is F. Preferably, y is 1, 2, 3 or 4, more preferably y is 1 or 2, and even more preferably y is 1. Preferably, $R^{13}$ is F and y is 1, 2, 3 or 4, more preferably $R^{13}$ is F and y is 1 or 2, and most preferably $R^{13}$ is F and y is 1. In other words, when $R^4$ is $-C_yR^{13}_{(2y+1)}$ it is preferred that $R^4$ is $-C_4F_9$, $-C_3F_7$, $-C_2F_5$ or $-CF_3$, more preferred that $R^4$ is $-C_2F_5$ or $-CF_3$, and most preferred that $R^4$ is $-CF_3$.

$R^4$ is preferably independently selected from the group consisting of F, Cl, Br and $-C_yR^{13}_{(2y+1)}$, wherein y and $R^{13}$ are as defined above. More preferably, $R^4$ is independently selected from the group consisting of F, Cl, Br, $-C_4F_9$, $-C_3F_7$, $-C_2F_5$ and $-CF_3$. Even more preferably, $R^4$ is independently selected from the group consisting of F, Cl, Br, $-C_2F_5$ and $-CF_3$. Yet even more preferably, $R^4$ is independently selected from the group consisting of F, Cl and $-CF_3$, and even more preferably $R^4$ is selected independently from the group consisting of F and Cl. Most preferably, $R^4$ is F.

In a halogenated aliphatic 1,3-dipole compound it is preferred that two substituents $R^4$ are bonded to the same $sp^3$ C-atom the 1,3-dipole functional group is bonded to. It is further preferred that the two substituents $R^4$ that are bonded to the same $sp^3$ C-atom as the 1,3-dipole functional group, are identical.

When the halogenated aliphatic 1,3-dipole compound is according to Formula (2), it is particularly preferred that f is 2e. In other words, when e is 1, it is particularly preferred that f is 2, when e is 2 it is particularly preferred that f is 4, etc. In a preferred embodiment, the halogenated aliphatic 1,3-dipole compound thus is according to Formula (2a):

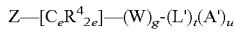   2a wherein:
Z, $R^4$, W, L', A', e, g, t and u, are as defined above for (2).

In (2a), e is preferably 1-8, more preferably 1-6, more preferably e is 1, 2, 3 or 4, yet more preferably e is 1, 2 or 3, even more preferably e is 1 or 2, and most preferably e is 1.

When $R^4$ is $-C_yR^{13}_{(2y+1)}$, it is preferred that $R^{13}$ is F. Preferably, y is 1, 2, 3 or 4, more preferably y is 1 or 2, and even more preferably y is 1. Preferably, $R^{13}$ is F and y is 1, 2, 3 or 4, more preferably $R^{13}$ is F and y is 1 or 2, and most preferably $R^{13}$ is F and y is 1. In other words, when $R^4$ is $-C_yR^{13}_{(2y+1)}$ it is preferred that $R^4$ is $-C_4F_9$, $-C_3F_7$, $-C_2F_5$ or $-CF_3$, more preferred that $R^4$ is $-C_2F_5$ or $-CF_3$, and most preferred that $R^4$ is $-CF_3$.

$R^4$ is preferably selected from the group consisting of F, Cl, Br and $-C_yR^{13}_{(2y+1)}$, wherein y and $R^{13}$ are as defined above. More preferably, $R^4$ is selected from the group consisting of F, Cl, Br, $-C_4F_9$, $-C_3F_7$, $-C_2F_5$ and $-CF_3$. Even more preferably, $R^4$ is selected from the group consisting of F, Cl, Br, $-C_2F_5$ and $-CF_3$. Yet even more preferably, $R^4$ is selected from the group consisting of F, Cl and $-CF_3$, and even more preferably $R^4$ is selected from the group consisting of F and Cl. Most preferably, $R^4$ is F.

W, if present, is preferably selected from the group consisting of $C_1$-$C_{12}$ alkylene groups, $C_2$-$C_{12}$ alkenylene groups, $C_3$-$C_{12}$ cycloalkylene groups, $C_2$-$C_{12}$ (hetero)arylene groups, $C_3$-$C_{12}$ alkyl(hetero)arylene groups and $C_3$-$C_{12}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N.

More preferably, W, when present, is selected from the group consisting of $C_1$-$C_6$ alkylene groups, $C_2$-$C_6$ alkenylene groups, $C_3$-$C_6$ cycloalkylene groups, $C_2$-$C_6$ (hetero)arylene groups, $C_3$-$C_6$ alkyl(hetero)arylene groups and $C_3$-$C_6$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N.

Even more preferably W, when present, is selected from the group consisting of $C_1$-$C_4$ alkylene groups, wherein the alkylene groups are optionally substituted and optionally interrupted by one or more heteroatoms selected from the group consisting of O, S and N.

Even more preferably W, when present, is selected from the group consisting of $-CH_2-$, $-CH_2-CH_2-$, $-CH_2-CH_2-CH_2-$ and $-CH_2-CH_2-CH_2-CH_2-$, more preferably from the group consisting of $-CH_2-$, $-CH_2-CH_2-$ and $-CH_2-CH_2-CH_2-$. Yet even more preferably W, when present, is $-CH_2-$ or $-CH_2-CH_2-$, and most preferably W, when present, is $-CH_2-$.

In a further preferred embodiment, the halogenated aliphatic 1,3-dipole compound is according to Formula (2b) or (2c), more preferably (2b):

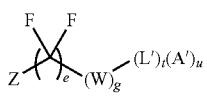

2b

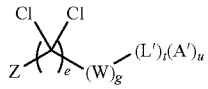

2c wherein:
Z, W, L', A', e, g, t and u are as defined above.

In (2b) and (2c), e is preferably 1-8, more preferably e is 1, 2, 3, 4, 5 or 6, more preferably e is 1, 2, 3 or 4, yet more preferably e is 1, 2 or 3, even more preferably e is 1 or 2 and most preferably e is 1.

Z is preferably selected from the group consisting of an azide group, a nitrone group, a nitrile oxide group and a diazo group. Most preferably, Z is an azide group. W, if present, is preferably selected from the group consisting of $C_1$-$C_{24}$ alkylene groups and $C_1$-$C_{24}$ (hetero)arylene groups. Further preferred embodiments of W are described above.

Preferred embodiments of L', A', t and u are described in more detail below.

In a particularly preferred embodiment of all halogenated aliphatic 1,3-dipole compounds described herein, A' is a saccharide moiety. The saccharide moiety may be a monosaccharide moiety, an oligosaccharide moiety or a polysaccharide moiety. The monosaccharide moiety, oligosaccharide moiety or polysaccharide moiety is optionally substituted, for example with a nucleotide (Nuc).

The nucleotide Nuc is preferably selected from the group consisting of a nucleoside monophosphate and a nucleoside diphosphate, more preferably from the group consisting of uridine diphosphate (UDP), guanosine diphosphate (GDP), thymidine diphosphate (TDP), cytidine diphosphate (CDP) and cytidine monophosphate (CMP), more preferably from the group consisting of uridine diphosphate (UDP), guanosine diphosphate (GDP), cytidine diphosphate and (CDP). Most preferably, the nucleotide is UDP.

Preferably, the saccharide moiety is a monosaccharide moiety, more preferably a saccharide moiety selected from the group consisting of galactose (Gal), mannose (Man), N-acetylglucosamine (GlcNAc), glucose (Glc), N-acetylgalactosamine (GalNAc), fucose (Fuc) and N-acetylneuraminic acid (sialic acid Sia or NeuNAc), even more preferably from the group consisting of GlcNAc, Glc, Gal and GalNAc, yet even more preferably from Gal or GalNAc. Most preferably, the monosaccharide moiety is GalNAc. The nucleotide is preferably bonded to C1 of the monosaccharide moiety, and the 1,3-dipole functional group is preferably bonded via the N-acetyl group of the GalNAc moiety.

In a particularly preferred embodiment, the aliphatic halogenated 1,3-dipole compound is according to Formula (2d), and in an even more particularly preferred embodiment, the aliphatic halogenated 1,3-dipole compound is according to Formula (2e):

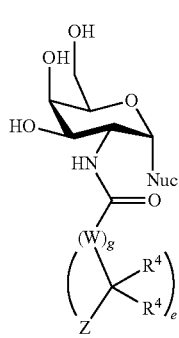

2d

-continued

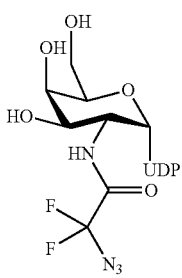

2e wherein:
Z, W, e, g and R$^4$ are as defined above;
Nuc is a nucleotide;
UDP is uridine diphosphate.

In another particularly preferred embodiment, the aliphatic halogenated 1,3-dipole compound is the GlcNAc-derived diastereoisomer of GalNAc-derived compounds (2d) or (2e), and consequently in this embodiment the aliphatic halogenated 1,3-dipole compound is according to Formula (2d') or (2e'):

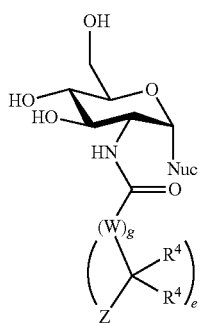

2d'

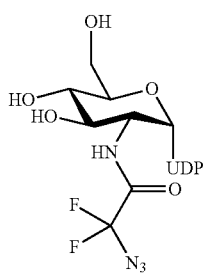

2e' wherein:
Z, W, e, g, R$^4$, Nuc and UDP are as defined above for (2d) and (2e).

Herein, when a compound is defined as the GlcNAc-derived diastereoisomer of a particular GalNAc-derived compound, it is to be understood that said GlcNAc-derived diastereoisomer only differs from said GalNAc-derived compound in the stereochemical configuration at C4, as is shown above for GalNAc-derived (2d) and its GlcNAc-derived diastereoisomer (2d'), and for GalNAc-derived (2e) and its GlcNAc-derived diastereoisomer (2e').

In another particularly preferred embodiment of the process according to the invention, the aliphatic halogenated 1,3-dipole compound is according to Formula (2v) or (2w), or their GlcNAc-derived diastereoisomers:

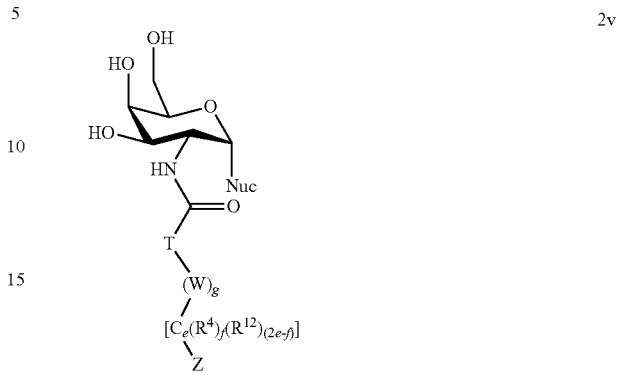

2v

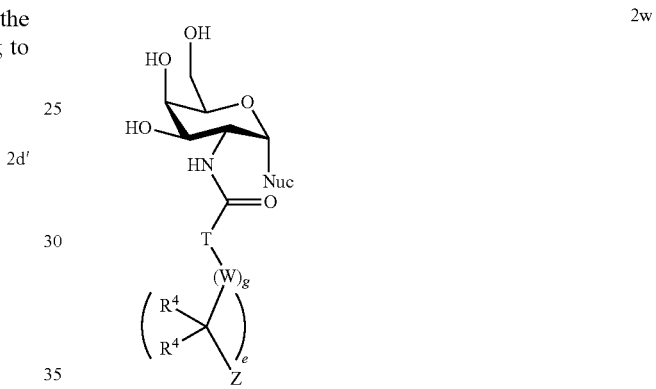

2w wherein:
Z, W, e, g, R$^{12}$ and R$^4$ are as defined above;
T is O or NH; and
Nuc is a nucleotide.

Preferred embodiments for Z, R$^4$, W, Nuc, g and e are as described above. In a preferred embodiment of (2d) and (2e), and in a preferred embodiment of (2v) and (2w), R$^4$ is F, Cl or Br. More preferably, R$^4$ is F or Cl, and most preferably R$^4$ is F. Z is a 1,3-dipole functional group. 1,3-Dipole functional groups are described in more detail above. In a preferred embodiment, Z is a selected from the group consisting of an azide group, a nitrile oxide group, a diazo group and a nitrone group. Preferably, Z is an azide group. In a further preferred embodiment Z is selected from the group consisting of an azide group, a nitrile oxide group, a diazo group and a nitrone group, and R$^4$ is F, Cl or Br. More preferably, Z is an azide group and R$^4$ is F or Cl. Most preferably, Z is an azide group and R$^4$ is F. In these embodiments it is further preferred that W, if present, is —CH$_2$—, —CH$_2$—CH$_2$—, —CH$_2$—CH$_2$—CH$_2$— or —CH$_2$—CH$_2$—CH$_2$—CH$_2$. In these embodiments it is further preferred that T is O.

Throughout this description, the claims and the drawings, when nucleotide Nuc is UDP, the nucleotide has the structure shown below.

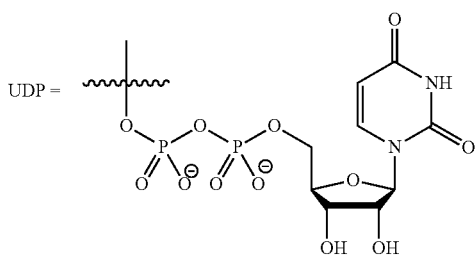

When the halogenated 1,3-dipole compound is according to Formula (2d) or (2w), it is further preferred that said compound is according to Formula (2x), (2y), (2z), (2za) or (2zb), or their GlcNAc-derived diastereoisomers:

wherein UDP is uridine diphosphate and T is O or NH, preferably O.

In (2x), (2y), (2z), (2za) and (2zb) the structure of UDP is as shown above.

In another preferred embodiment, the invention relates to a halogenated 1,3-dipole compound according to formula (2f), (2g), (2h), (2i):

-continued

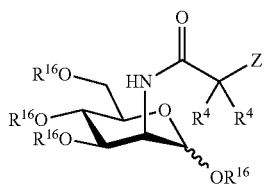

2h

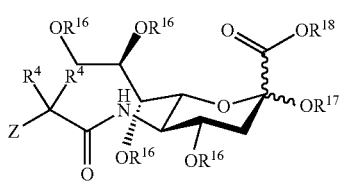

2i wherein:

R⁴ and Z are as defined above;

R¹⁶ and R¹⁷ are independently selected from the group consisting of hydrogen, C(O)NR¹⁸, C(O)R¹⁸ and C(O)OR¹⁸, wherein R¹⁸ is as defined below; and R¹⁸ is independently selected from the group consisting of $C_1$-$C_{24}$ alkyl groups and $C_1$-$C_{24}$ (hetero)aryl groups.

Preferably, R¹⁸ is selected from the group consisting of $C_1$-$C_{12}$ alkyl groups and $C_1$-$C_{12}$ (hetero)aryl groups, more preferably from the group consisting of $C_1$-$C_6$ alkyl groups and $C_1$-$C_6$ (hetero)aryl groups. Most preferably R¹⁸ is methyl, ethyl, n-propyl, i-propyl, n-butyl, t-butyl, phenyl or benzyl.

In a preferred embodiment of (2f), (2g), (2h) or (2i), R⁴ is F, Cl or Br. More preferably, R⁴ is F or Cl, and most preferably R⁴ is F.

Z is a 1,3-dipole functional group. 1,3-Dipole functional groups are described in more detail above. In a preferred embodiment, Z is a selected from the group consisting of an azide group, a nitrile oxide group, a diazo group and a nitrone group. Preferably, Z is an azide group.

In a further preferred embodiment Z is selected from the group consisting of an azide group, a nitrile oxide group, a diazo group and a nitrone group, and R⁴ is F, Cl or Br. More preferably, Z is an azide group and R⁴ is F or Cl. Most preferably, Z is an azide group and R⁴ is F.

In a further preferred embodiment, the invention relates to a halogenated 1,3-dipole compound according to formula (2j), (2k), (2l) or (2m):

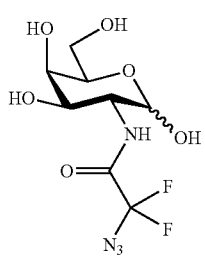

2j

-continued

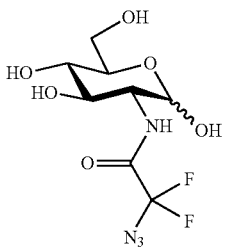

2k

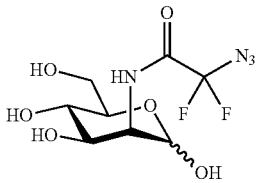

2l

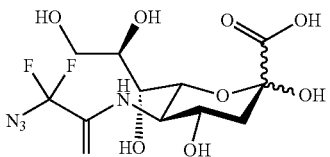

2m

Unless otherwise defined above, when the halogenated aliphatic 1,3-dipole compound is according to Formula (2), (2a), (2b), (2c), (2d), (2e), (2f), (2g), (2h) or (2i), and preferred embodiments thereof, as described above, it is preferred that Z is selected from the group consisting of a nitrone group, an azide group, a diazo group, a nitrile oxide group, a nitronate group, a nitrile imine group, a sydnone group, a sulfon hydrazide group, a pyridine oxide group and a oxadiazole 1-oxide group, more preferably from the group consisting of a nitrone group, an azide group, a diazo group and a nitrile oxide group, and even more preferably from the group consisting of a nitrone group, an azide group and a nitrile oxide group. Most preferably, Z is an azide group.

More than one A' may be present in the halogenated 1,3-dipole compound (u is 1, 2, 3 or 4). A' is independently selected from the group consisting of D, E and Q, wherein D is a molecule of interest, E is a solid surface and Q is a functional group. Molecules of interest D, solid surfaces E and functional groups Q are described in more detail below.

In the process according to the invention, A' is selected independently from A that is present in the (hetero)cycloalkyne. In the (hetero)cycloalkyne, A is also defined as a molecule of interest D, a solid surface E or a functional group Q. However, since A and A' are selected independently, A' in the halogenated 1,3-dipole compound, and preferred embodiments thereof, may be different from A in the (hetero)cycloalkyne according to Formula (1), and preferred embodiments thereof.

A molecule of interest D may for example be a reporter molecule, a diagnostic compound, an active substance, an enzyme, an amino acid (including an unnatural amino acid), a (non-catalytic) protein, a peptide, a polypeptide, an oligonucleotide, a monosaccharide, an oligosaccharide, a polysaccharide, a glycan, a (poly)ethylene glycol diamine (e.g. 1,8-diamino-3,6-dioxaoctane or equivalents comprising longer ethylene glycol chains), a polyethylene glycol chain, a polyethylene oxide chain, a polypropylene glycol chain, a polypropylene oxide chain or a 1,x-diaminoalkane (wherein x is the number of carbon atoms in the alkane).

An active substance is a pharmacological and/or biological substance, i.e. a substance that is biologically and/or pharmaceutically active, for example a drug or a prodrug, a diagnostic agent, an amino acid, a protein, a peptide, a polypeptide, a monosaccharide, an oligosaccharide, a polysaccharide, a glycan, a lipid, a vitamin, a steroid, a nucleotide, a nucleoside, a polynucleotide, RNA or DNA. Examples of suitable peptide tags include a cell-penetrating peptides like human lactoferrin or polyarginine. An example of a suitable glycan is oligomannose. Preferably, the active substance is selected from the group consisting of drugs and prodrugs. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include colchicine, vinca alkaloids, camptothecins, doxorubicin, daunorubicin, taxanes, calicheamycins, duocarmycins, maytansines, auristatins, tubulysin, irinotecans, an inhibitory peptide, amanitin, deBouganin, or pyrrolobenzodiazepines (PBDs).

A reporter molecule is a molecule whose presence is readily detected, for example a diagnostic agent, a dye, a fluorophore, a radioactive isotope label, a contrast agent, a magnetic resonance imaging agent or a mass label. Examples of a fluorophore include all kinds of Alexa Fluor (e.g. Alexa Fluor 555), cyanine dyes (e.g. Cy3 or Cy5), coumarin derivatives, fluorescein, rhodamine, allophycocyanin and chromomycin.

Examples of radioactive isotope label include $^{99m}$Tc, $^{68}$Ga, $^{18}$F, $^{11}$C, $^{64}$Cu, $^{131}$I or $^{123}$I, which may or may not be connected via a chelating moiety such as DTPA, DOTA, NOTA or HYNIC.

A solid surface E is for example a functional surface (e.g. nanomaterials, carbon nanotubes, fullerenes, virus capsids), metal surface (e.g. gold, silver, copper, nickel, tin, rhodium, zinc) or a metal alloy surface (from aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc, zirconium), a polymer surface (e.g. polystyrene, polyvinylchloride, polyethylene, polypropylene, poly(dimethylsiloxane), polymethylmethacrylate, polyisocyanate). E is preferably independently selected from the group consisting of a functional surface or a polymer surface.

A functional group Q is preferably independently selected from the group consisting of hydrogen, halogen, $R^{11}$, —CH=C($R^{11}$)$_2$, —C≡C$R^{11}$, —[C($R^{11}$)$_2$C($R^{11}$)$_2$O]$_q$—$R^{11}$ wherein q is in the range of 1 to 200, —CN, —N$_3$, —NCX, —XCN, —X$R^{11}$, —N($R^{11}$)$_2$, —$^+$N($R^{11}$)$_3$, —C(X)N($R^{11}$)$_2$, —C($R^{11}$)$_2$X$R^{11}$, —C(X)$R^{11}$, —C(X)X$R^{11}$, —S(O)$R^{11}$, —S(O)$_2R^{11}$, —S(O)O$R^{11}$, —S(O)$_2$O$R^{11}$, —S(O)N($R^{11}$)$_2$, —S(O)$_2$N($R^{11}$)$_2$, —OS(O)$R^{11}$, —OS(O)$_2R^{11}$, —OS(O)O$R^{11}$, —OS(O)$_2$O$R^{11}$, —P(O)($R^{11}$)(O$R^{11}$), —P(O)(O$R^{11}$)$_2$, —OP(O)(O$R^{11}$)$_2$, —Si($R^{11}$)$_3$, —XC(X)$R^{11}$, —XC(X)X$R^{11}$, —XC(X)N($R^{11}$)$_2$, —N($R^{11}$)C(X)$R^{11}$, —N($R^{11}$)C(X)X$R^{11}$ and —N($R^{11}$)C(X)N($R^{11}$)$_2$, wherein X is oxygen or sulphur and wherein $R^{11}$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O and N.

Preferably $R^{11}$ is independently selected from the group consisting of hydrogen, halogen and $C_1$-$C_6$ alkyl groups, more preferably from the group consisting of hydrogen, halogen and $C_1$-$C_4$ alkyl groups. Most preferably, $R^{11}$ is independently selected from the group consisting of hydrogen, methyl, ethyl, propyl, i-propyl, butyl and t-butyl. X is preferably oxygen.

Optionally, functional group Q is masked or protected. More preferably, Q is independently selected from the group consisting of —CN, —NCX, —XCN, —X$R^{11}$, —N($R^{11}$)$_2$, —$^+$N($R^{11}$)$_3$, —C(X)N($R^{11}$)$_2$, —C($R^{11}$)$_2$X$R^{11}$, —C(X)$R^{11}$, —C(X)X$R^{11}$, —XC(X)$R^{11}$, —XC(X)X$R^{11}$, —XC(X)N($R^{11}$)$_2$, —N($R^{11}$)C(X)$R^{11}$, —N($R^{11}$)C(X)X$R^{11}$ and —N($R^{11}$)C(X)N($R^{11}$)$_2$, wherein X and $R^{11}$, and preferred embodiments of X and $R^{11}$, are as defined above. Most preferably, Q is selected from the group consisting of —O$R^{11}$, —S$R^{11}$, —N($R^{11}$)$_2$, —$^+$N($R^{11}$)$_3$, —C(O)N($R^{11}$)$_2$, —C(O)O$R^{11}$, —OC(O)$R^{11}$, —OC(O)O$R^{11}$, —OC(O)N($R^{11}$)$_2$, —N($R^{11}$)C(O)$R^{11}$, ($R^{11}$)C(O)O$R^{11}$ and —N($R^{11}$)C(O)N($R^{11}$)$_2$, wherein X and $R^{11}$, and preferred embodiments of X and $R^{11}$, are as defined above.

In a preferred embodiment of the process according to the invention, A' is a molecule of interest D. More preferably, A' is independently selected from the group consisting of a reporter molecule, an active substance, an enzyme, a protein, a glycoprotein, an antibody, a peptide, a polypeptide, an oligonucleotide, a monosaccharide, an oligosaccharide, a polysaccharide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above.

In a particularly preferred embodiment, A' is a glycoprotein, preferably an antibody. When A' is a glycoprotein, it is preferred that the halogenated aliphatic 1,3-dipole compound is bonded to the glycoprotein via a saccharide moiety of the glycoprotein glycan.

In another particularly preferred embodiment, A' is a saccharide moiety. The saccharide moiety may be a monosaccharide moiety, an oligosaccharide moiety or a polysaccharide moiety. The monosaccharide moiety, oligosaccharide moiety or polysaccharide moiety is optionally substituted, for example with a nucleotide. The nucleotide is preferably selected from the group consisting of a nucleoside monophosphate and a nucleoside diphosphate, more preferably from the group consisting of uridine diphosphate (UDP), guanosine diphosphate (GDP), thymidine diphosphate (TDP), cytidine diphosphate (CDP) and cytidine monophosphate (CMP), more preferably from the group consisting of uridine diphosphate (UDP), guanosine diphosphate (GDP), cytidine diphosphate and (CDP). Most preferably, the nucleotide is UDP. Preferably, the saccharide moiety is a monosaccharide moiety, more preferably a saccharide moiety selected from the group consisting of galactose (Gal), mannose (Man), N-acetylglucosamine (GlcNAc), glucose (Glc), N-acetylgalactosamine (GalNAc), fucose (Fuc) and N-acetylneuraminic acid (sialic acid Sia or NeuNAc), even more preferably from the group consisting of GlcNAc, Glc, Gal and GalNAc, yet even more preferably from GlcNAc or GalNAc. Most preferably, the monosaccharide moiety is GalNAc. The nucleotide is preferably bonded to C1 of the monosaccharide moiety, and the halogenated 1,3-dipole functional group is preferably bonded via the N-acetyl group of the GalNAc moiety.

When t is 1, a linker L' is present in the halogenated 1,3-dipole compound. L' is a linker, herein also referred to as linking unit. One or more A' may be bonded via linker L' (u is 1, 2, 3 or 4). When more than one A' is present (u is 2, 3 or 4), each A' is independently selected, in other words each A' may be different from the others. Preferably, u is 1 or 2 and most preferably u is 1.

Linker L' is selected independently selected from linker L that is present in the (hetero)cycloalkyne. In other words, linker L' in the halogenated 1,3-dipole compound, and preferred embodiments thereof, may be different from linker L in the (hetero)cycloalkyne according to Formula (1), and preferred embodiments thereof.

Linkers are well known in the art. L' and L' may for example be independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are substituted, and optionally said groups are interrupted by one or more heteroatoms, preferably 1 to 100 heteroatoms, said heteroatoms preferably being selected from the group consisting of O, S and N.

In another particularly preferred embodiment of the process according to the invention, the halogenated 1,3-dipole compound is according to Formula (2zc) or (2zd), or their GlcNAc-derived diastereoisomers:

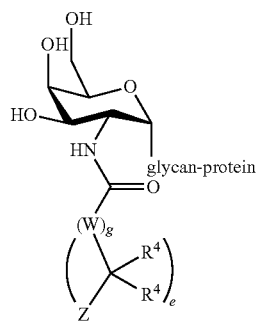

2zc

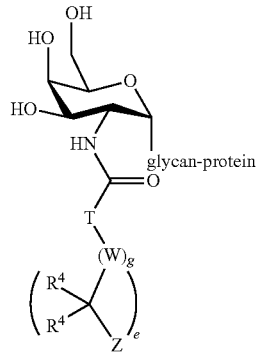

2zd wherein:
W, g, Z, $R^4$ and e are as defined above, and T is O or NH, preferably O.

When the halogenated 1,3-dipole is according to Formula (2zc) or (2zd), it is further preferred that said compound is according to Formula (2ze), (2zf), (2zg), (2zh), (2zi), (2zj) or (2zk), or their GlcNAc-derived diastereoisomers:

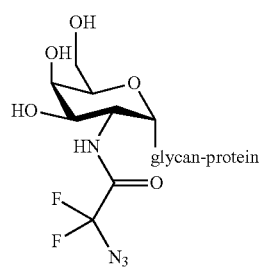

2ze

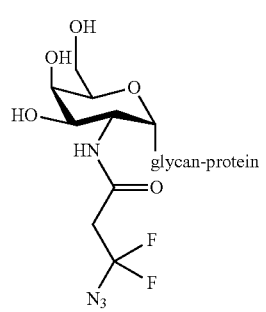

2zf

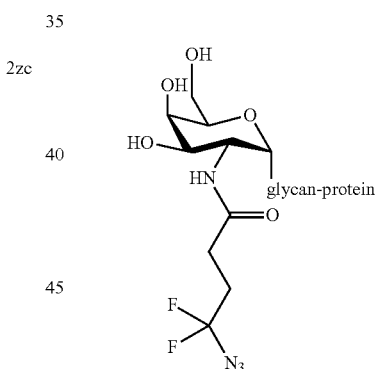

2zg

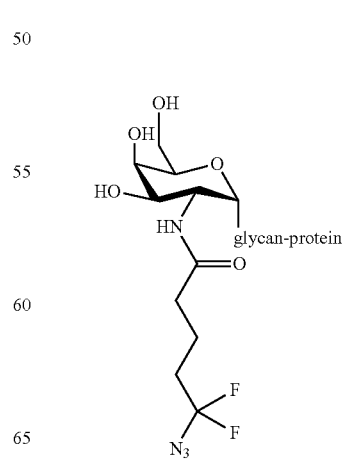

2zh

-continued

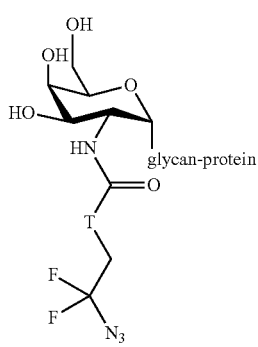

2zi

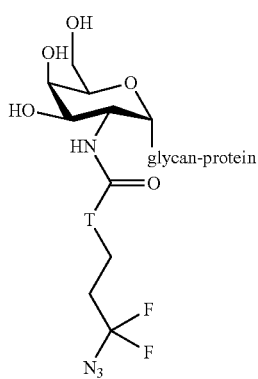

2zj

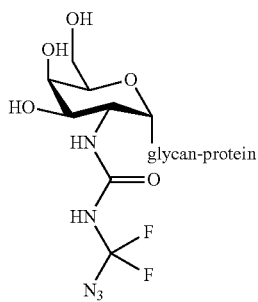

2zk wherein T is O or NH, preferably O.

In these embodiments, when the halogenated 1,3-dipole is according to Formula (2zc), (2zd), (2ze), (2zf), (2zg), (2zh), (2zi), (2zj) or (2zk), A' is a glycoprotein. When A' is a glycoprotein, it is preferred that the halogenated aliphatic 1,3-dipole functional group is bonded to the glycoprotein via a saccharide moiety of the glycoprotein glycan. In a further preferred embodiment A' is an antibody, and in this embodiment it is further preferred that the halogenated aliphatic 1,3-dipole functional group is bonded to the antibody via a saccharide moiety of the antibody glycan. In these embodiments the halogenated 1,3-dipole functional group is bonded to C2 via the N-acetyl group of a GalNAc moiety, said GalNAc moiety being bonded via C1 to a saccharide moiety of the glycan, preferably to a GlcNAc moiety, more preferably to C4 of said GlcNAc moiety, even more preferably via a β(1,4)-glycosidic bond.

In (2zc), (2zd), (2ze), (2zf), (2zg), (2zh), (2zi), (2zj) and (2zk), the term "glycan" may refer to a monosaccharide moiety, but also to an oligosaccharide moiety. When the term "glycan" refers to a monosaccharide moiety, the monosaccharide moiety is preferably a GlcNAc moiety. When the term "glycan" refers to an oligosaccharide moiety, it is preferred that the saccharide moiety that is connected to C1 of the GalNAc moiety comprising the 1,3-dipole functional group, is a GlcNAc moiety.

In a particularly preferred embodiment of the process according to the invention, the halogenated 1,3-dipole compound is according to Formula (2d), (2e), (2f), (2g), (2h), (2i), (2j), (2k), (2l) or (2m) as described in more detail above. In another particularly preferred embodiment of the process according to the invention, the halogenated 1,3-dipole compound is according to Formula (2zc), (2zd), (2v), (2w), (2zc), (2zd), (2x), (2y), (2z), (2za) or (2zb) as described in more detail above.

As described above and below, in another particularly preferred embodiment of the process according to the invention, the (hetero)cycloalkyne is a (hetero)cyclooctyne according to Formula (1) as defined above, wherein a is 0, 1, 2, 3 or 4, a' is 0, 1, 2, 3 or 4 and a" is 0, 1, 2, 3 or 4, with the proviso that a+a'+a"=4, and wherein n is 0-8. In this particularly preferred embodiment it is further preferred that the halogenated 1,3-dipole compound is according to Formula (2d), (2e), (2f), (2g), (2h), (2i), (2j), (2k), (2l) or (2m), or that the halogenated 1,3-dipole compound is according to Formula (2zc), (2zd), (2v), (2w), (2zc), (2zd), (2x), (2y), (2z), (2za) or (2zb).

(Hetero)Cycloalkyne

The term (hetero)cycloalkyne herein refers to cycloalkynes as well as to heterocycloalkynes. In the process according to the invention, the (hetero)cycloalkyne is according to Formula (1), wherein a, a', a", n, p, q, r, B, B', L, A and $R^1$ are as defined above:

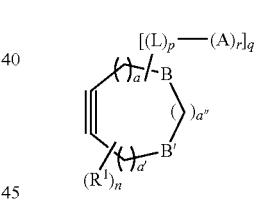

1

As was described above, a is 0 to 8, a' is 0 to 8 and a" is 0 to 8, with the proviso that a+a'+a" is 4, 5, 6, 7 or 8. As a consequence, the (hetero)cycloalkyne according to Formula (1) is a (hetero)cyclooctyne (a+a'+a" is 4), a (hetero)cyclononyne (a+a'+a" is 5), a (hetero)cyclodecyne (a+a'+a" is 6), a (hetero)cycloundecyne (a+a'+a" is 7) or a (hetero)cyclododecyne (a+a'+a" is 8).

When the (hetero)cycloalkyne according to Formula (1) is a (hetero)cyclooctyne and (a+a'+a" is 4), a is 0, 1, 2, 3 or 4, a' is 0, 1, 2, 3 or 4 and a" is 0, 1, 2, 3 or 4. When the (hetero)cycloalkyne according to Formula (1) is a (hetero)cyclononyne and (a+a'+a" is 5), a is 0, 1, 2, 3, 4 or 5, a' is 0, 1, 2, 3, 4 or 5 and a" is 0, 1, 2, 3, 4 or 5. When the (hetero)cycloalkyne according to Formula (1) is a (hetero)cyclodecyne and (a+a'+a" is 6), a is 0, 1, 2, 3, 4, 5 or 6, a' is 0, 1, 2, 3, 4, 5 or 6 and a" is 0, 1, 2, 3, 4, 5 or 6. When the (hetero)cycloalkyne according to Formula (1) is a (hetero)cycloundecyne and (a+a'+a" is 7), a is 0, 1, 2, 3, 4, 5, 6 or 7, a' is 0, 1, 2, 3, 4, 5, 6 or 7 and a" is 0, 1, 2, 3, 4, 5, 6 or 7. When the (hetero)cycloalkyne according to Formula (1) is a (hetero)cyclododecyne and (a+a'+a") is 8), a is 0, 1, 2, 3, 4, 5, 6, 7 or 8, a' is 0, 1, 2, 3, 4, 5, 6, 7 or 8 and a" is 0, 1, 2, 3, 4, 5, 6, 7 or 8.

Preferably, the (hetero)cycloalkyne in the process according to the invention is a (hetero)cyclooctyne, i.e. preferably a+a'+a" is 4 in the (hetero)cycloalkyne according to Formula (1). In this embodiment, a, a' and a" are independently 0, 1, 2, 3 or 4, with the proviso that a+a'+a" is 4. In a preferred embodiment, a is 1, a' is 1 and a" is 2. In another preferred embodiment, a is 2, a' is 2 and a" is 0. In another preferred embodiment, a is 2, a' is 2 and a" is 0, and B or B' is O, S, C(O), $NR^3$ or $C(R^1)(R^3)$. When B or B' is $NR^3$, it is further preferred that $R^3$ is $(L)_p$-$(A)_r$. When B or B' is $C(R^1)(R^3)$, it is further preferred that $R^3$ is $(L)_p$-$(A)_r$.

When a is one or more, the one or more C-atoms present between the C≡C triple bond and B are herein also referred to as a-C-atoms. In analogy, when a' is one or more, the one or more C-atoms present between the C≡C triple bond and B' are herein also referred to as a-C-atoms, and if a" is one or more, the one or more C-atoms present between B and B' are herein also referred to as a"-C-atoms.

$R^1$ is independently selected from the group consisting of oxo, halogen, $-OR^2$, $-NO_2$, $-CN$, $-S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups.

When the (hetero)cycloalkyne according to Formula (1) is a (hetero)cyclooctyne n is 0-8, when the (hetero)cycloalkyne is a (hetero)cyclononyne n is 0-10, when the (hetero)cycloalkyne is a (hetero)cyclodecyne n is 0-12, when the (hetero)cycloalkyne is a (hetero)cycloundecyne n is 0-14 and when the (hetero)cycloalkyne is a (hetero)cyclododecyne n is 0-16. Preferably, n is 0, 1, 2, 3, 4, 5, 6, 7 or 8, more preferably n is 0, 1, 2, 3, 4, 5 or 6, even more preferably n is 0, 1, 2, 3 or 4 and most preferably n is 0, 1 or 2.

As described above, if q in (hetero)cycloalkyne (1) is 0, then:
  (i) B and/or B' is $NR^3$ wherein $R^3$ is $(L)_p$-$(A)_r$;
  (ii) B and/or B' is $C(R^3)_2$ wherein one or more $R^3$ is $(L)_p$-$(A)_r$;
  (iii) n is 2 or more and two $R^1$ groups together form a (hetero)cycloalkyl group wherein the (hetero)cycloalkyl group is substituted with an $(L)_p$-$(A)_r$ substituent; and/or
  (iv) n is 2 or more and two $R^1$ groups together form a (hetero)aryl group wherein the (hetero)aryl group is substituted with an $(L)_p$-$(A)_r$ substituent.

Optionally, when n is 2 or more, two $R^1$ groups on adjacent (hetero)cycloalkyne C-atoms may together form a (hetero)aryl group, the (hetero)aryl group optionally being substituted with an $(L)_p$-$(A)_r$ substituent. Said (hetero)aryl ring is annulated, i.e. fused, to the (hetero)cycloalkyne ring. In this embodiment it is preferred that the (hetero)cycloalkyne is according to Formula (1d) or (1e):

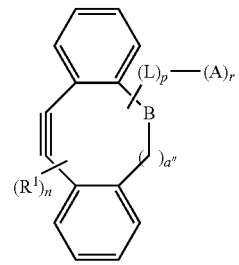

1d

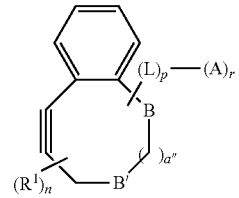

1e wherein $R^1$, B, B', L, A, n, p and r are as defined above; and wherein a" is 0-4.

In this embodiment it is preferred that a" is 1-5. More preferably a" is 1, 2 or 3 and most preferably a" is 1. In other words, most preferably the (hetero)cycloalkyne is a heterocyclooctyne.

Optionally, when n is 2 or more, two $R^1$ groups, preferably on adjacent C-atoms, may together form a (hetero)cycloalkyl group, the (hetero)cycloalkyl group optionally being substituted with an $(L)_p$-$(A)_r$ substituent. Preferably, the two $R^1$-groups, preferably on adjacent C-atoms, together form a (hetero)cyclopropyl group, a (hetero)cyclobutyl group, a (hetero)cyclopentyl group or a (hetero)cyclohexyl group, more preferably a (hetero)cyclopropyl group, a (hetero)cyclobutyl group or a (hetero)cyclopentyl group and most preferably a cyclopropyl group, all optionally being substituted with an $(L)_p$-$(A)_r$ substituent. Preferably, the a (hetero)cycloalkyl group that is formed by the two $R^1$ groups is fused to the (hetero)cycloalkyne. Therefore it is preferred in this embodiment that a is 2 or more, and/or a' is 2 or more, and/or a" is 2 or more. Alternatively, it is preferred in this embodiment that a is 1 and B is $NR^1$ or $C(R^3)_2$ wherein at least one of $R^3$ is $R^1$, and/or a' is 1 and B' is $NR^1$ or $C(R^3)_2$ wherein at least one of $R^3$ is $R^1$.

In this embodiment, it is preferred that the (hetero)cycloalkyne is according to Formula (1c):

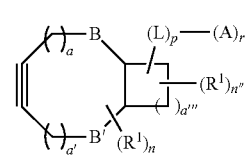

1c wherein B, B', L, A, a, a', p, r and q are as defined above, and wherein n is 0, 1, 2, 3 or 4, n" is 0, 1, 2, 3 or 4 and a'" is 0, 1, 2 or 3.

When p is 1, then A is bonded to the (hetero)cycloalkyne via L. L is a linker, herein also referred to as linking unit. The (hetero)cycloalkyne may be bonded to one or to more A via linker L (r is 1, 2, 3 or 4). When more than one A is present (r is 2, 3 or 4), each A is independently selected, in other words each A may be different from the other(s). Preferably, r is 1 or 2 and most preferably r is 1.

The description of A and preferred embodiments of A corresponds to the description of A' and preferred embodiments of A' in the halogenated 1,3-dipole as described in more detail above. Both A in the (hetero)cycloalkyne and A' in the halogenated 1,3-dipole compound are defined as a molecule of interest D, a solid surface E or a functional group Q. Molecules of interest D, solid surfaces E and functional groups Q are described in more detail above. However, since A and A' are selected independently, A' in the halogenated 1,3-dipole compound according to Formula (2) or (3), and in preferred embodiments thereof, may be different from A in the (hetero)cycloalkyne according to Formula (1), and preferred embodiments thereof.

In a preferred embodiment of the process according to the invention, A is a molecule of interest D. More preferably, A is independently selected from the group consisting of a reporter molecule, an active substance, an enzyme, a protein, a glycoprotein, an antibody, a peptide, a polypeptide, an oligonucleotide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above.

Linker L is selected independently from linker L' that is present in the halogenated 1,3-dipole compound. In other words, linker L in the (hetero)cycloalkyne according to Formula (1) and preferred embodiments thereof, may be different from linker L in the halogenated 1,3-dipole compound according to Formula (2) or (3) and preferred embodiments thereof.

Linking units are described in more detail above. The description of L and preferred embodiments of L correspond to the description of L' and preferred embodiments of L'. However, as described above, L and L' are selected independently from one another, and consequently L may differ from L' in the process according to the invention.

In a preferred embodiment of the process according to the invention, the (hetero)cycloalkyne is a (hetero)aromatic (hetero)cycloalkyne. A (hetero)aromatic (hetero)cycloalkyne is herein defined as a (hetero)cycloalkyne wherein at least one of the $sp^1$ C-atoms of the (hetero)cycloalkyne carbon-carbon triple bond is bonded to an $sp^2$ C-atom. In other words, a (hetero)aromatic (hetero)cycloalkyne herein refers to a (hetero)cycloalkyne wherein at least one of the two C-atoms adjacent to the carbon-carbon triple bond C≡C is an $sp^2$ C-atom.

In this embodiment, it is preferred that:
(i) when a is 2 or more, the (hetero)aryl group is fused to the 2 a-C-atoms that are nearest to the $sp^1$ C-atom of the carbon-carbon triple bond;
(ii) when a' is 2 or more, the (hetero)aryl group is fused to the 2 a'-C-atoms that are nearest to the $sp^1$ C-atom of the carbon-carbon triple bond;
(iii) when a is 1 and B is $C(R^1)(R^3)$, the (hetero)aryl group is fused to the a-C-atom and the C-atom of B; and/or
(iv) when a' is 1 and B' is $C(R^1)(R^3)$, the (hetero)aryl group is fused to the a-C-atom and the C-atom of B'.

In other words, in a (hetero)aromatic (hetero)cycloalkyne, a (hetero)aryl group is annulated to the (hetero)cycloalkyne, and said (hetero)aryl group is present adjacent to the carbon-carbon triple bond.

Preferably, both $sp^1$ C-atoms of the (hetero)cycloalkyne carbon-carbon triple bond are bonded to an $sp^2$ C-atom, i.e. preferably, two (hetero)aryl groups are annulated to the (hetero)cycloalkyne: one (hetero)aryl group at each side of the carbon-carbon triple bond.

It is further preferred that a 6-membered (hetero)aryl group is fused to the (hetero)cycloalkyne.

A (hetero)aromatic (hetero)cycloalkyne wherein one (hetero)aryl group is fused to the (hetero)cycloalkyne, adjacent to the carbon-carbon triple bond, is herein also referred to as a benzoannulated (hetero)cycloalkyne. A (hetero)aromatic (hetero)cycloalkyne wherein two (hetero)aryl groups are fused to the (hetero)cycloalkyne, on both sides of the carbon-carbon triple bond, is herein also referred to as a dibenzoannulated (hetero)cycloalkyne. The term (di)benzoannulated (hetero)cycloalkynes is herein meant to include benzoannulated (hetero)cycloalkynes as well as dibenzoannulated (hetero)cycloalkynes.

When the (hetero)cycloalkyne is a (di)benzoannulated (hetero)cycloalkyne, it is further preferred that a 6-membered (hetero)aryl group is fused to the (hetero)cycloalkyne.

In a preferred embodiment of the process according to the invention, the (hetero)cycloalkyne is a (di)benzoannulated (hetero)cycloalkyne according to Formula (1f):

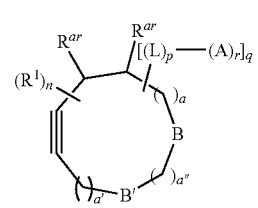

wherein:
a is 0, 1, 2, 3, 4, 5 or 6;
a' is 0, 1, 2, 3, 4, 5 or 6;
a" is 0, 1, 2, 3, 4, 5 or 6;
with the proviso that a+a'+a"=2, 3, 4, 5 or 6;
n is 0-12;
the two $R^{ar}$ groups together form a (hetero)aryl group, the (hetero)aryl group optionally being substituted with an $(L)_p$-$(A)_r$ substituent;
optionally, when a' is 2 or more and n is 2 or more, two $R^1$ groups present on adjacent a'-C-atoms may together form a (hetero)aryl group, the (hetero)aryl group optionally being substituted with an $(L)_p$-$(A)_r$ substituent;
optionally, when a' is 1, n is 1 or more and B' is $C(R^1)(R^3)$, $R^1$ present on the a'-C-atom may together with $R^1$ of B' form a (hetero)aryl group, the (hetero)aryl group optionally being substituted with an $(L)_p$-$(A)_r$ substituent;
$R^1$ is independently selected from the group consisting of oxo, halogen, —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;

B and B' are independently selected from the group consisting of O, S, C(O), NR$^3$ and C(R$^3$)$_2$, wherein R$^3$ is independently selected from the group consisting of hydrogen, R$^1$ and (L)$_p$-(A)$_r$;
p is 0 or 1;
r is 1-4;
L is a linker;
A is independently selected from the group consisting of D, E or Q, wherein D, E and
Q are as defined below;
q is 0-4;
with the proviso that if q is 0, then B and/or B' is NR$^3$ wherein R$^3$ is (L)$_p$-(A)$_r$, and/or B and/or B' is C(R$^3$)$_2$ wherein one or more R$^3$ is (L)$_p$-(A)$_r$, and/or a' is 2 or more and n is 2 or more and two R$^1$ groups present on adjacent a'-C-atoms together form a (hetero)aryl group, the (hetero)aryl group being substituted with an (L)$_p$-(A)$_r$ substituent, and/or the (hetero)aryl group formed by the two R$^{ar}$ groups is substituted with an (L)$_p$-(A)$_r$ substituent;
D is a molecule of interest;
E is a solid surface; and
Q is a functional group.

The preferred embodiments for R$^1$, L' and A' as described above for a (hetero)cycloalkyne according to Formula (1) also apply to the preferred embodiments of R$^1$, L and A of the (hetero)aromatic (hetero)cycloalkyne according to Formula (1f). It is further preferred that r is 1 or 2, preferably 1.

Preferably, the (hetero)cycloalkyne according to Formula (1f) is a (hetero)cyclooctyne. When the (hetero)cycloalkyne according to Formula (1f) is a (hetero)cyclooctyne n is 0-4, when the (hetero)cycloalkyne is a (hetero)cyclononyne n is 0-6, when the (hetero)cycloalkyne is a (hetero)cyclodecyne n is 0-8, when the (hetero)cycloalkyne is a (hetero)cycloundecyne n is 0-10 and when the (hetero)cycloalkyne is a (hetero)cyclododecyne n is 0-12. Preferably, n is 0, 1, 2, 3, 4, 5, 6, 7 or 8, more preferably n is 0, 1, 2, 3, 4, 5 or 6, even more preferably n is 0, 1, 2, 3 or 4 and most preferably n is 0, 1 or 2.

When the (hetero)cycloalkyne according to Formula (1f) is a (hetero)cyclooctyne a+a'+a"=2. When the (hetero)cycloalkyne according to Formula (1f) is a (hetero)cyclononyne a+a'+a"=3. When the (hetero)cycloalkyne according to Formula (1f) is a (hetero)cyclodecyne a+a'+a"=4. When the (hetero)cycloalkyne according to Formula (1f) is a (hetero)cycloundecyne a+a'+a"=5. When the (hetero)cycloalkyne according to Formula (1f) is a (hetero)cyclododecyne a+a'+a"=6.

In a preferred embodiment, a+a'+a"=2, i.e. preferably the (hetero)cycloalkyne is a (hetero)cycooctyne.

In a further preferred embodiment, the (hetero)cycloalkyne is a dibenzoannulated (hetero)cycloalkyne according to Formula (1d), or a benzoannulated (hetero)cycloalkyne according to Formula (1e):

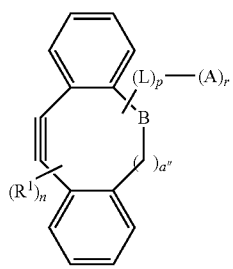

1d

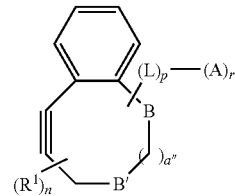

1e wherein B, B', R$^1$, L, A, a, a', n, p, r and q are as defined above.

When the (hetero)cycloalkyne is a (hetero)aromatic (hetero)cycloalkyne, it is further preferred that the (hetero)cycloalkyne is a (hetero)cyclooctyne. More preferably, the (hetero)cyclooctyne is according to Formula (5), (11) or (12):

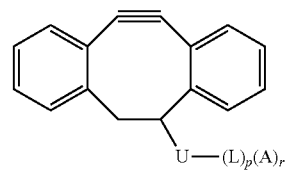

5

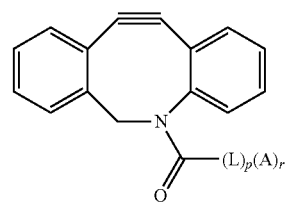

11

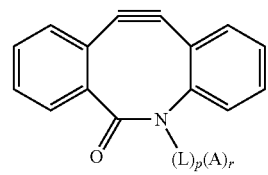

12 wherein L, A, p and r are as defined above; and
U is O, S or NR$^{19}$, wherein R$^{19}$ is selected from the group consisting of hydrogen and C$_1$-C$_{24}$ alkyl groups.

Preferably, U is O or NR$^{19}$, more preferably U is O. Preferably, R$^{19}$ is selected from the group consisting of hydrogen and C$_1$-C$_{12}$ alkyl groups, more preferably from the group consisting of hydrogen and C$_1$-C$_6$ alkyl groups, even more preferably from the group consisting of hydrogen, methyl, ethyl, n-propyl, i-propyl, n-butyl and t-butyl. Most preferably, R$^{19}$ is selected from the group consisting of methyl, ethyl, n-propyl, propyl, n-butyl and t-butyl.

In a (hetero)aromatic (hetero)cycloalkyne according to Formula (1d), (1e), (1f), (5), (11) and (12), r is preferably 1 or 2, more preferably 1, and A is preferably selected from the group consisting of a reporter molecule, an active substance, an enzyme, a protein, a glycoprotein, an antibody, a peptide, a polypeptide, an oligonucleotide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above.

In another preferred embodiment of the process according to the invention, the (hetero)cycloalkyne is an aliphatic (hetero)cycloalkyne. An aliphatic (hetero)cycloalkyne is herein defined as a (hetero)cycloalkyne wherein both $sp^1$ C-atoms of the (hetero)cycloalkyne carbon-carbon triple bond are bonded to an $sp^3$ C-atom. In other words, an aliphatic (hetero)cycloalkyne herein refers to a (hetero)cycloalkyne wherein the two C-atoms on each side of the carbon-carbon triple bond C≡C are $sp^3$ C-atoms.

In a further preferred embodiment, the (hetero)cycloalkyne is an aliphatic (hetero)cycloalkyne according to Formula (3):

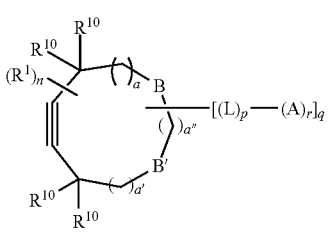

3 wherein:
a is 0, 1, 2, 3, 4, 5 or 6;
a' is 0, 1, 2, 3, 4, 5 or 6;
a" is 0, 1, 2, 3, 4, 5 or 6;
with the proviso that a+a'+a"=2, 3, 4, 5 or 6;
n is 0-12;
$R^1$ is independently selected from the group consisting of halogen, —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;

optionally, when n is 2 or more, two $R^1$ groups may together form a (hetero)cycloalkyl group, the (hetero)cycloalkyl group optionally being substituted with an $(L)_p$-$(A)_r$ substituent;

optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;

$R^{10}$ is independently selected from the group consisting of $(L)_p$-$(A)_r$ wherein L, A, p and r are as defined below, hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted and wherein the alkyl groups, cycloalkyl groups, alkyl(hetero)aryl groups and (hetero)arylalkyl groups are optionally interrupted by one or more heteroatoms selected from the group consisting of O, S and N;

B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;

p is 0 or 1;
r is 1-4;
L is a linker;
A is independently selected from the group consisting of D, E and Q, wherein D, E and
Q are as defined below;
q is 0-4;

with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent, and/or one or more of $R^{10}$ is $(L)_p$-$(A)_r$;

D is a molecule of interest;
E is a solid surface; and
Q is a functional group.

The preferred embodiments for $R^1$, L' and A' as described above for a (hetero)cycloalkyne according to Formula (1) also apply to the preferred embodiments of $R^1$, L and A in an aliphatic (hetero)cycloalkyne according to Formula (3). It is further preferred that r is 1 or 2.

When the aliphatic (hetero)cycloalkyne according to Formula (3) is a (hetero)cyclooctyne n is 0-4, when the (hetero)cycloalkyne is a (hetero)cyclononyne n is 0-6, when the (hetero)cycloalkyne is a (hetero)cyclodecyne n is 0-8, when the (hetero)cycloalkyne is a (hetero)cycloundecyne n is 0-10 and when the (hetero)cycloalkyne is a (hetero)cyclododecyne n is 0-12. Preferably, n is 0, 1, 2, 3, 4, 5, 6, 7 or 8, more preferably n is 0, 1, 2, 3, 4, 5 or 6, even more preferably n is 0, 1, 2, 3 or 4 and most preferably n is 0, 1 or 2.

As described above, if q in aliphatic (hetero)cycloalkyne (3) is 0, then:
(i) B and/or B' is $NR^3$ wherein $R^3$ is $(L)_p$-$(A)_r$;
(ii) B and/or B' is $C(R^3)_2$ wherein one or more of $R^3$ is $(L)_p$-$(A)_r$;
(iii) n is 2 or more and two $R^1$ groups together form a (hetero)cycloalkyl group wherein the (hetero)cycloalkyl group is substituted with an $(L)_p$-$(A)_r$ substituent;
(iv) a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent; and/or
(v) one or more of $R^{10}$ is $(L)_p$-$(A)_r$.

In an aliphatic (hetero)cycloalkyne, when two $R^1$ groups on adjacent a"-C-atoms optionally form a fused (hetero)aryl group it is preferred that the (hetero)cycloalkyne is according to Formula (3b), and when two $R^1$ groups on adjacent a"-C-atoms optionally form a (hetero)cycloalkyl group, it is preferred that the (hetero)cycloalkyne is according to Formula (3c):

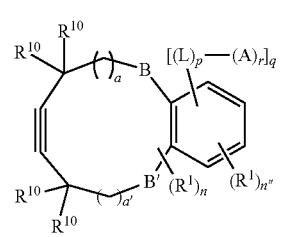

3b

-continued

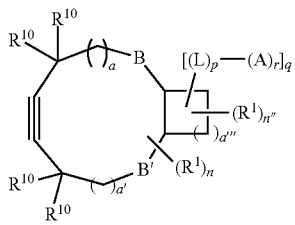
3c

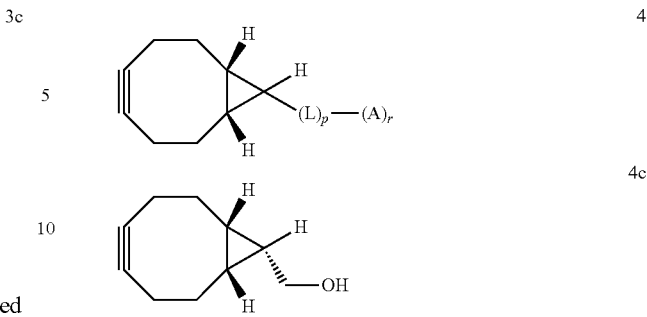
4

4c wherein B, B', $R^1$, $R^{10}$, L, A, a, a', p, r and q are as defined above for (3), and wherein n' is 0, 1, 2, 3 or 4, n" is 0, 1, 2, 3 or 4 and a'" is 0, 1, 2 or 3. The preferred embodiments for $R^1$, L' and A' as described above for a (hetero)cycloalkyne according to Formula (1) also apply to the preferred embodiments of $R^1$, L and A (hetero)cycloalkyne according to Formula (3b) and (3c). It is further preferred that r is 1 or 2.

In a preferred embodiment of the process according to the invention, when the (hetero)cyclooctyne is an aliphatic (hetero)cyclooctyne, the aliphatic (hetero)cycloalkyne is according to Formula (4):

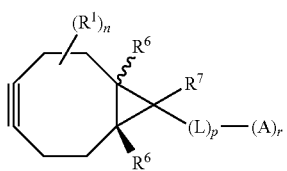
4 wherein:
$R^1$, L, p, r and A and preferred embodiments thereof are as defined above;
n is 0-8;
$R^6$ is independently selected from the group consisting of hydrogen, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and
$R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted.

In a preferred embodiment, n is 0. In another preferred embodiment, $R^6$ is H. In another preferred embodiment, $R^7$ is H. In a further preferred embodiment, n is 0, $R^6$ is H and $R^7$ is H. In another further preferred embodiment, the (hetero)cycloalkyne is according to Formula (4b), wherein L, A, p and r are as defined above:

In another preferred embodiment, n is 0, $R^6$ is H, $R^7$ is H and p is 1. More preferably, r is 1 or 2, most preferably r is 1. An example of a (hetero)cycloalkyne according to Formula (4b) is (hetero)cycloalkyne (4c), wherein p is 1, L is $CH_2$, r is 1 and A is a functional group Q, namely —OH.

In another preferred embodiment of the process according to the invention, when the (hetero)cyclooctyne is an aliphatic (hetero)cyclooctyne, the (hetero)cyclooctyne is according to Formula (6), (7), (8), (9) or (10):

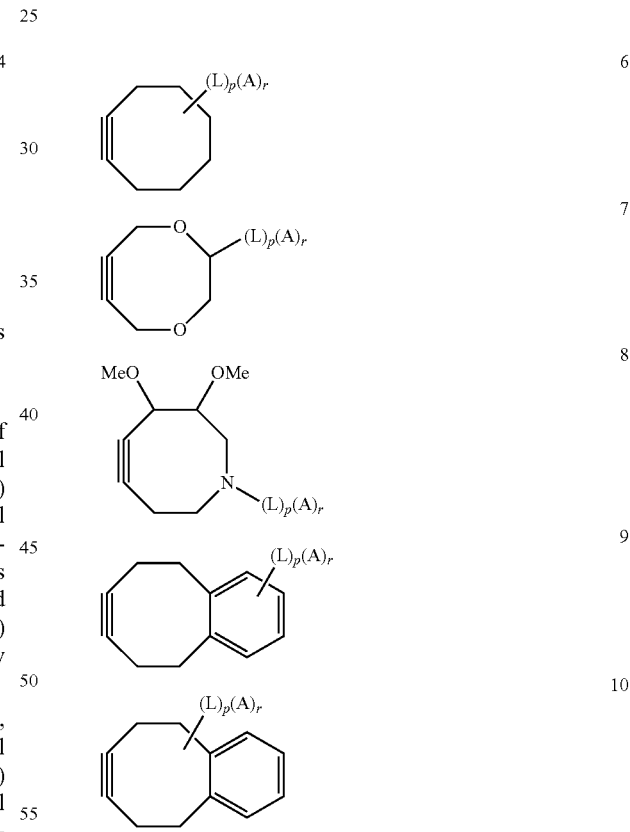

wherein L, p, r and A, as well as preferred embodiments thereof, are as described above.

When the (hetero)cycloalkyne is according to Formula (7), it is preferred that -$(L)_p$-$(A)_r$ is present on C5 of the cyclooctyne.

Also in a (hetero)cycloalkyne according to Formula (4), (4b), (4c), (5), (6), (7), (8), (9) and (10), r is preferably 1 or 2, more preferably 1, and A is preferably selected from the group consisting of a reporter molecule, an active substance, an enzyme, a protein, a glycoprotein, an antibody, a peptide, a polypeptide, an oligonucleotide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above.

In one embodiment of the cycloaddition process according to the invention, a halogenated aliphatic 1,3-dipole compound according to Formula (2), or a preferred embodiment thereof as described in more detail above, reacts with a (hetero)cycloalkyne according to Formula (1), or a preferred embodiment thereof. In this embodiment, the (hetero)cycloalkyne may be an aliphatic (hetero)cycloalkyne or an aromatic (hetero)cycloalkyne. Aliphatic (hetero)cycloalkyne and aromatic (hetero)cycloalkynes are described in more detail above.

In another embodiment of the cycloaddition process according to the invention, a halogenated aliphatic 1,3-dipole compound according to Formula (2), or a preferred embodiment thereof as described in more detail above, reacts with an aliphatic (hetero)cycloalkyne according to Formula (3), or a preferred embodiment thereof.

In another embodiment of the cycloaddition process according to the invention, a halogenated aliphatic 1,3-dipole compound according to Formula (2), or a preferred embodiment thereof as described in more detail above, reacts with a (di)benzoannulated (hetero)cycloalkyne according to Formula (1f), or a preferred embodiment thereof.

In a preferred embodiment of the process according to the invention, the (hetero)cycloalkyne is a (hetero)cyclooctyne, as was described in more detail above. The (hetero)cyclooctyne may be an aliphatic (hetero)cyclooctyne, e.g. according to Formula (3), but the (hetero)cyclooctyne may also be a benzoannulated or a dibenzoannulated (hetero)cyclooctyne, e.g. according to Formula (1f).

In a particularly preferred embodiment of the process according to the invention, the (hetero)cycloalkyne is according to formula (4), (5), (6), (7), (8), (9), (10), (11) or (12), or preferred embodiments thereof. In another particularly preferred embodiment of the process according to the invention, the (hetero)cycloalkyne is according to formula (4), more preferably according to Formula (4b) or (4c).

In another particularly preferred embodiment of the process according to the invention, L' is absent and A' in the halogenated aliphatic 1,3-dipole compound is a glycoprotein, preferably an antibody. When A' is a glycoprotein, it is preferred that the halogenated aliphatic 1,3-dipole functional group is bonded to the glycoprotein via a saccharide moiety of the glycoprotein glycan. The halogenated aliphatic 1,3-dipole compound is preferably according to Formula (2) or preferred embodiments thereof.

Figure 7:
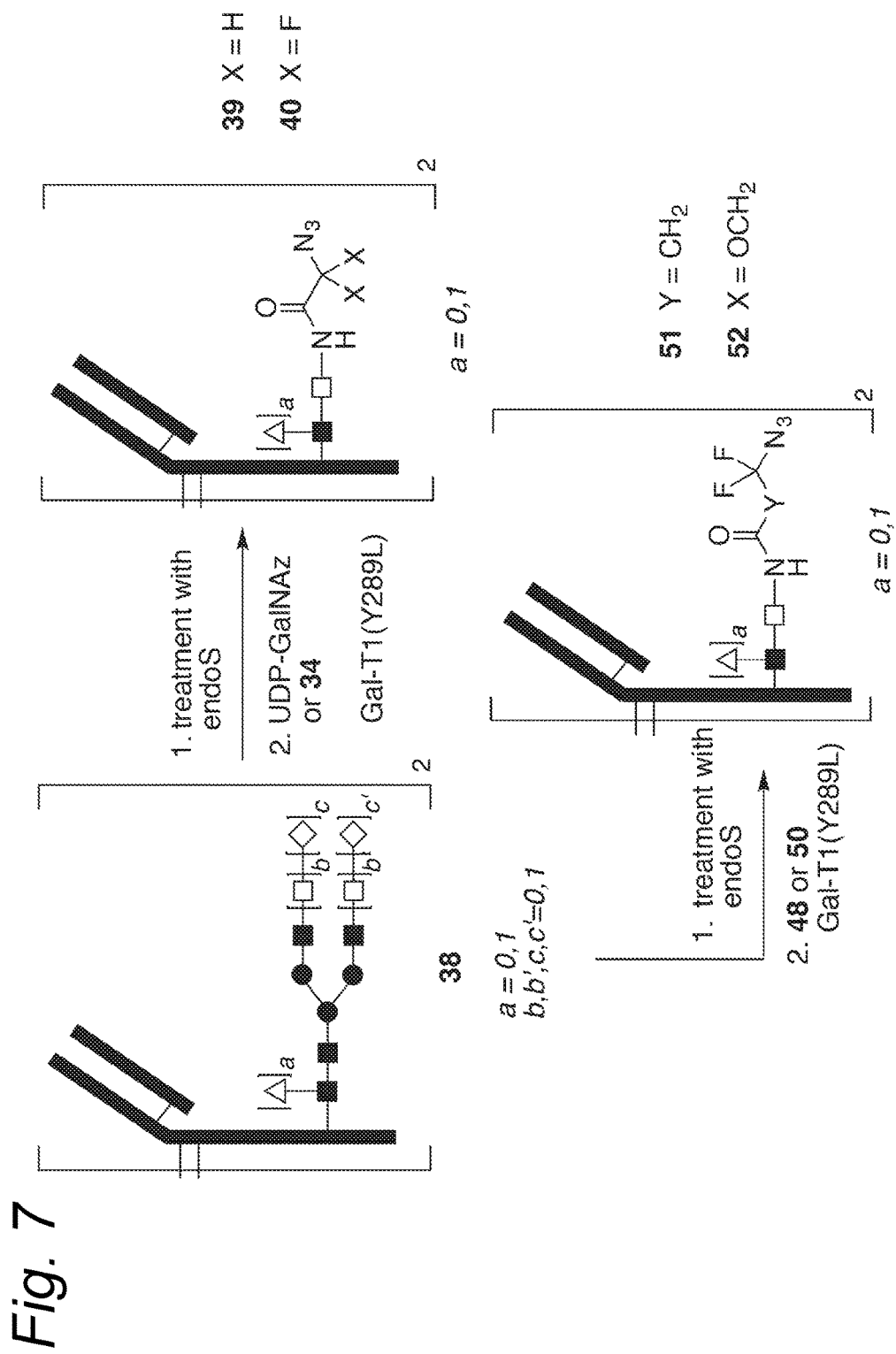
FIG. 7 shows the scheme for conversion of an IgG (38) into an azido-modified IgG upon treatment with endoglycosidase (endo S), followed by enzymatic introduction of an azidosugar under the action of Gal-T1(Y289L) in the presence of UDP-GalNAz, UDP-F$_2$-GalNAz (34), UDP-homo-F$_2$-GalNAz (48) or UDP-F$_2$-GalNAz-carbamate (50). The starting IgG may contain different glycan isoforms, including fucosylation of the core GlcNAc (a=0 or 1), and terminal galactose sugars (b,b'=0 or 1). If a terminal galactose is present, the glycan may be further glycosylation with a sialic acid residue (c,c'=0 or 1).

In FIG. 7, a process is shown for the preparation of a halogenated aliphatic 1,3-dipole compound (40), wherein A' is an antibody. In a first step, the antibody is treated with endoS in order to trim the antibody glycan and leave only the core-GlcNAc on the antibody. In a second step, a halogenated aliphatic 1,3-dipole compound according to Formula (2), wherein A' is a UDP-galactose derivative and Z is an azide group, is coupled to the core-GlcNAc on the antibody in the presence of mutant galactosyltransferase Y289L, to obtain halogenated aliphatic 1,3-dipole compound (40).

Reaction Rate k and Relative Reaction Rate $k_{rel}$

One of the advantages of the cycloaddition process according to the invention is that the reaction rate of the cycloaddition of a halogenated aliphatic 1,3-dipole compound with a (hetero)cycloalkyne may be tailored by the halogen substituents present in the halogenated aliphatic 1,3-dipole compound.

We here wish to disclose that the reaction rate of a 1,3-dipole compound, e.g. an azide, can be enhanced by introduction of (one or more) neighbouring halogen substituents on an aliphatic 1,3-dipole compound.

The presence of one or more neighbouring halogen substituents on the 1,3-dipole compound, leads to a significant reaction rate enhancement of the process according to the invention. Despite the electron-withdrawing character of the substituent, reaction rate with cyclic (hetero)alkynes is enhanced upon halogen substitution. The increase in reaction rate of the cycloaddition is observed both when the (hetero)cycloalkyne is aliphatic and when the (hetero)cycloalkyne is (hetero)aromatic.

Aliphatic and (hetero)aromatic (hetero)cycloalkynes and halogenated aliphatic 1,3-dipole compounds, as well as their preferred embodiments, are described in more detail above.

In a preferred embodiment of the process according to the invention, the process has a relative rate constant $k_{rel}$ of 1 or more, wherein the relative rate constant $k_{rel}$ is defined as the rate constant of the process according to the invention, i.e. the cycloaddition of a (hetero)cycloalkyne according to Formula (1) with a halogenated aliphatic 1,3-dipole compound, divided by the rate constant of the cycloaddition of the same (hetero)cycloalkyne according to Formula (1) with the non-halogenated reference 1,3-dipole compound for the process. When the halogenated 1,3-dipole compound is a halogenated aliphatic 1,3-dipole compound (as defined above), the reference 1,3-dipole compound is the same aliphatic dipole with hydrogens in the position of the halogen atoms, i.e. non-halogenated.

Preferably, the relative rate constant $k_{rel}$ as defined above is 1 or more. In other words, the rate constant of the cycloaddition of a specific (hetero)cycloalkyne with a specific halogenated 1,3-dipole compound preferably is equal to or larger than the rate constant of the cycloaddition of the same (hetero)cycloalkyne with the reference non-halogenated 1,3-dipole compound.

In a further preferred embodiment, $k_{rel}$ is more than 1. Preferably, $k_{rel}$ is 1.3 or more, more preferably 1.4 or more, even more preferably 1.5 or more, even more preferably 1.7 or more, even more preferably 2.0 or more, yet even more preferably 2.2 or more and most preferably 2.5 or more.

Figure 2:
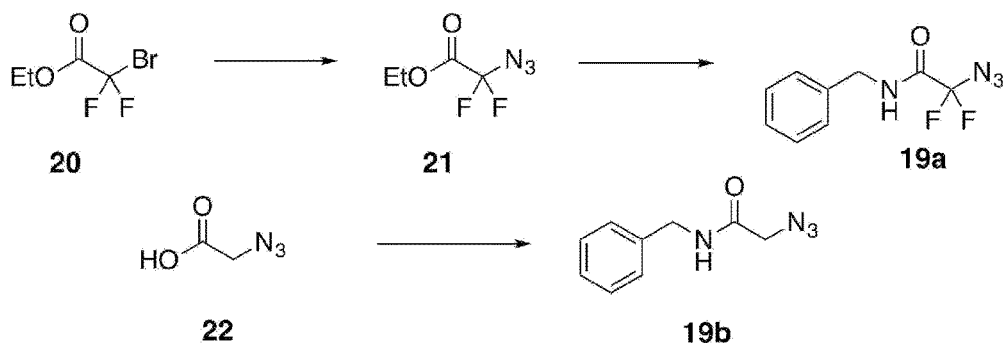
FIG. 2 shows the synthetic scheme for the preparation of compounds benzylamide derivative 19a and 19b.

In Table 1 the rate constants k and relative rate constants $k_{rel}$ of several examples of the process according to the invention are tabulated, wherein the (hetero)cycloalkyne is according to Formula (4c) or Formula (11b) and the halogenated aliphatic 1,3-dipole compound is according to Formula (19a) or (19b). Compounds 19a and 19b were prepared according to FIG. 2.

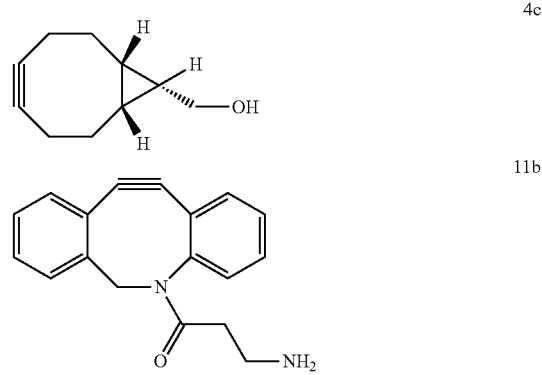

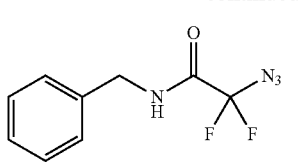

19a

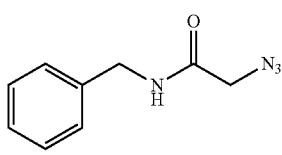

19b

TABLE 1

Rate constants k and relative rate constants $k_{rel}$ of the cycloaddition of difluorinated acetamide (19a) with (hetero)cycloalkyne (4c) and with (di)benzoannulated (hetero)cycloalkyne (11b). All experiments performed in THF/$H_2O$ = 9/1.

| | | Column 3-4 (4c) | | Column 4-5 (11b) | |
|---|---|---|---|---|---|
| Entry | azide | k ($M^{-1} s^{-1}$) | $k_{rel}$ | k ($M^{-1} s^{-1}$) | $k_{rel}$ |
| 1 | 19b (reference compound) | 0.048 | 1 (by definition) | 0.20 | 1 (by definition) |
| 2 | 19a | 0.11 | 2.3 | 0.24 | 1.2 |

These results clearly show that halogenated aliphatic azides give rise to a considerable rate enhancement with respect to the non-halogenated version of the same azide.

Figure 5:
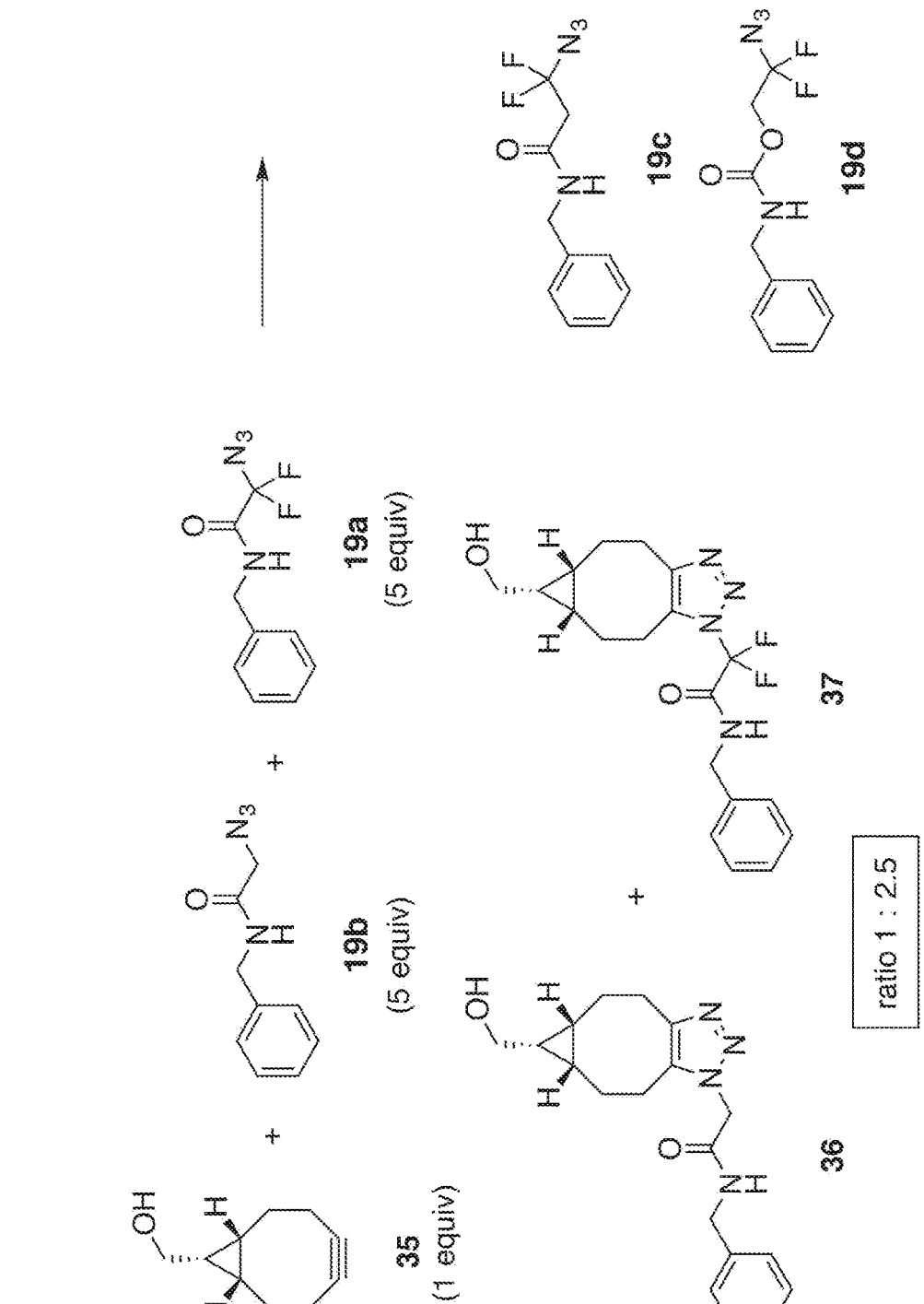
FIG. 5 shows the competition experiment on reactivity of regular azidoacetamide 19b versus difluoroazidoacetamide 19a with BCN-alcohol 35. Also shown are structures of difluorosubstituted azides 19c and 19b.
Figure 6:
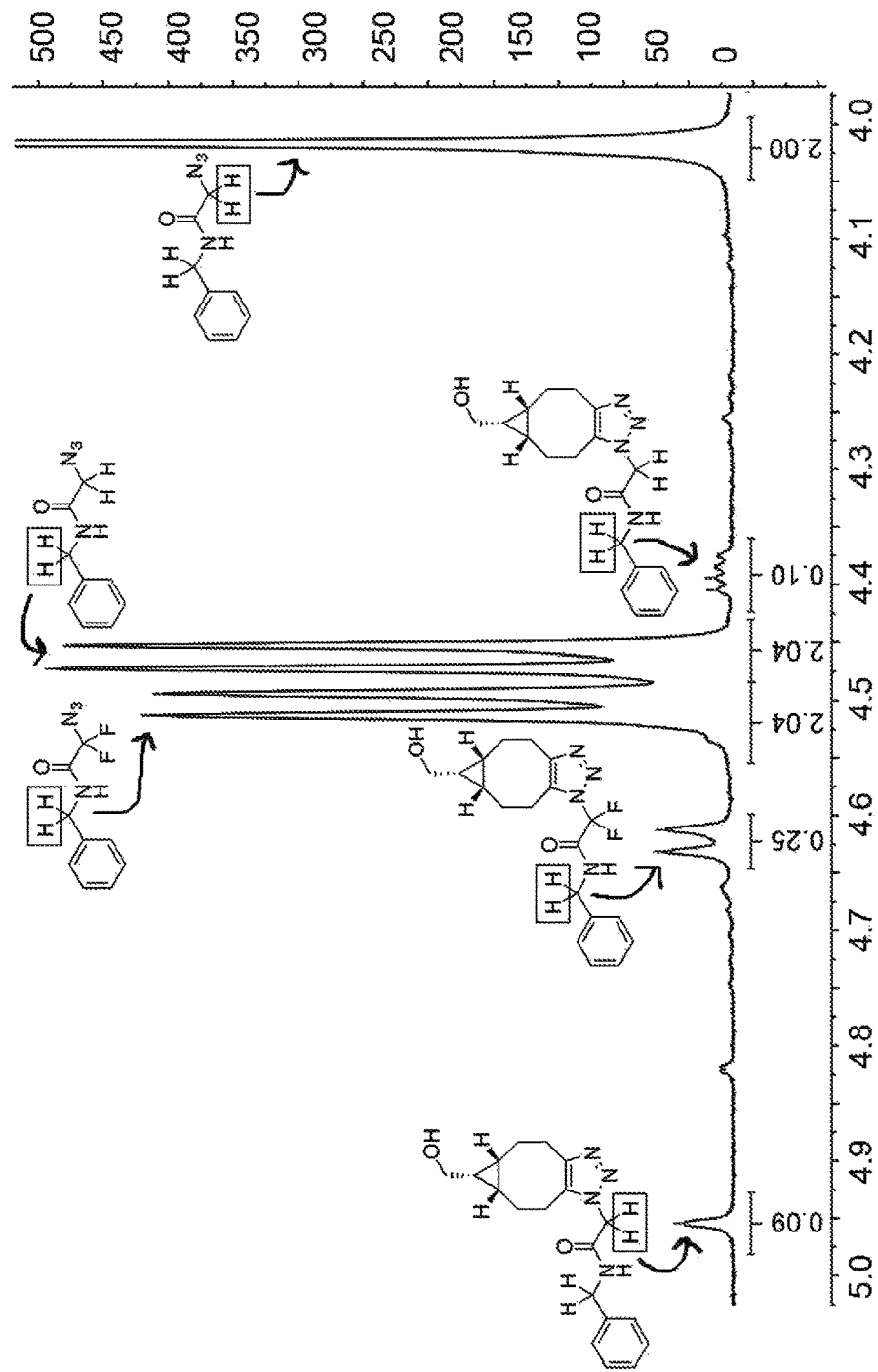
FIG. 6 shows the zoom of the crude NMR spectrum of the competition experiment between 19a and 19b with BCN alcohol 4a. Clearly visible are the methylene protons of cycloaddition of 19b as well as the benzylic protons for cycloadducts of both 19a and 19b.

FIG. 5 shows the competition experiment between regular azidoacetamide 19b and difluoroazidoacetamide 19a, both of which were added in 5-fold excess with respect to BCN-alcohol, in order to determine the relative reactivity of the two azides by analysis of the mixture of triazoles 36 and 37, respectively, formed upon cycloaddition. FIG. 6 shows the zoom of the NMR spectrum with the relevant protons of the two formed triazoles products 36 and 37. The relative ratio of triazoles 36:37 (1:2.5) can be calculated from the benzyl protons of 36 and the triazolylmethylene protons of both 36 and 37.

This observation is in contrast to the general opinion that 1,3-cycloaddition reactions of a (hetero)cycloalkyne and a 1,3-dipole proceed most efficiently with an electron-rich azide and an electron-deficient alkyne.

For example, the vast majority of model cycloadditions of SPAAC applications involve the reaction with an aliphatic azide, e.g. benzyl azide or azidoacetic acid. In general, aliphatic azides have been found to be more reactive than aromatic azides. For example, Hosoya et al. have reported that cycloadditions of benzyl azide or phenyl azide with Sondheimer's diyne (a dibenzoannulated cyclooctyne) in MeOH proceed with a reaction rate constant of 0.06 or 0.0088 $M^{-1}s^{-1}$, respectively, hence a factor 6.8 faster for benzyl azide (FIG. 1). Comparison of azides in reaction with DIBAC, as performed in our laboratory (undisclosed), shows a similar 7.3× higher reaction rate for benzyl azide versus phenyl azide. A similar observation was disclosed by Zimmerman et al., *Bioconj. Chem.* 2014, 25, 351-361, incorporated by reference herein. Interestingly, Hosoya et al., *Scientific Reports* 2011, 1, article number 82 (doi: 10.1038/srep00082), incorporated by reference herein, also recently reported that the reaction rate of Sondheimer's diyne with an aromatic azide can be increased by double ortho substitution of the aryl moiety of phenyl azide with alkyl groups, leading to a $k_{rel}$ of 36, 43 or even 76 for o,o-dimethyl, o,o-diethyl or o,o-diisopropyl substituents, respectively. Apart from the influence of steric hindrance, Hosoya et al. also explored the influence of electronegativity of substituents (FIG. 1). A modest positive effect on reaction rate (×3.8) was also noted for introduction of an electron-donating para-substituent (MeO). In contrast, an electron-withdrawing group (p-$CF_3$) led to an opposite effect (reaction rate×0.9). It has also been demonstrated that introduction of an electron-withdrawing substituent on the cyclooctyne instead of on the azide component has the opposite effect on reaction rate, as demonstrated by Bertozzi et al. for fluoride-substitution of BARAC in *J. Am. Chem. Soc.* 2012, 134, 9199, incorporated by reference. An important finding of the same report involves the enhancement of reaction rate of benzyl azide with BARAC upon difluorination of the latter. Based on free energy calculations, it is concluded that the reaction rate enhancement is a result of electronic modulation that generates enhanced stabilizing interactions in the transition state. The finding that the introduction of electron-withdrawing fluoride substituents on the cyclooctyne BARAC leads to reaction rate increase with azide is nicely in line with earlier observations for different versions of DIFO (Bertozzi et al., *Proc. Natl. Acad. Sci.* 2007, 104, 16793 and *J. Am. Chem. Soc.* 2008, 130, 11486, incorporated by reference). In both cases, it is reasoned that installing fluorine atoms leads to lowering of the cyclooctyne LUMO, thereby increasing its interaction energy with the HOMO of the azide. Hence, it can be concluded that an electron-rich azide, with higher HOMO, will react faster with cyclooctyne than an electron-poor azide.

According to these results from the prior art, it can be concluded that the most efficient cycloadditions of azides and cyclic alkynes involve electron-rich azides with electron-deficient alkynes.

Finally, Pezacki et al. (*Org. Biomol. Chem.* 2012, 10, 3066, incorporated by reference) have explored the influence of aromatic substituents on reaction rate of benzaldehyde-derived nitrones with BARAC. It was established that the nitrone-BARAC cycloaddition is poorly sensitive to substituents on the nitrone α-aryl group, so it was concluded that no significant rate enhancement can be obtained through aromatic substitution.

Halogenated 1,3-Dipole Compounds

The present invention discloses a number of halogenated aliphatic 1,3-dipole compounds.

The invention therefore also relates to halogenated 1,3-dipole compounds, in particular to halogenated 1,3-dipole compounds comprising N-acetylgalactosamine-UDP (GalNAc-UDP), and to halogenated 1,3-dipole compounds comprising (peracylated)N-acetylglucosamine (GlcNAc), N-acetylgalactosamine (GalNAc), N-acetylmannosamine (ManNAc) and N-acetylneuraminic acid (NeuNAc).

In a preferred embodiment, the invention relates to a halogenated 1,3-dipole compound according to Formula (2r), (2s), (2t) or (2u):

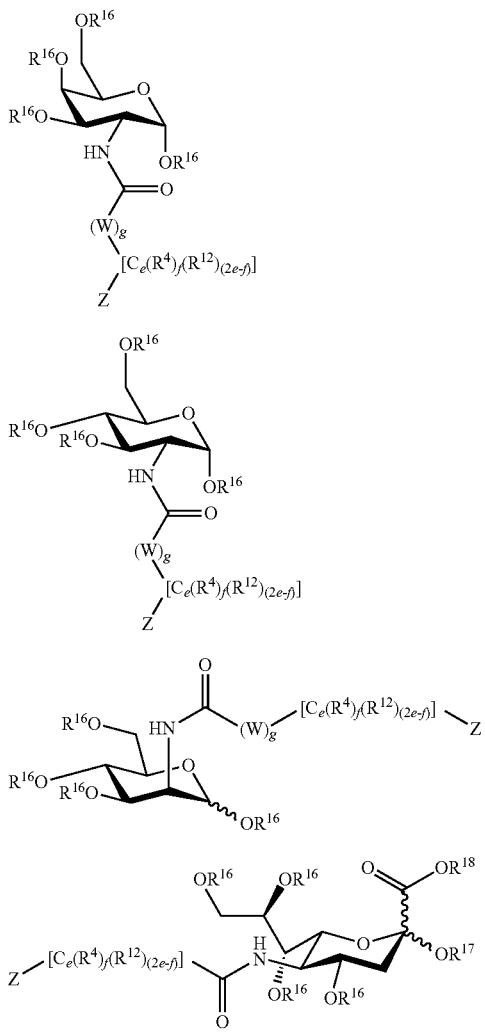

wherein:
W, g, Z, R$^4$, R$^{12}$, e and f are as defined above for (2);
R$^{16}$ and R$^{17}$ are independently selected from the group consisting of hydrogen, C(O)NR$^{18}$, C(O)R$^{18}$ and C(O)OR$^{18}$ wherein R$^{18}$ is as defined below; and
R$^{18}$ is selected from the group consisting of C$_1$-C$_{24}$ alkyl groups and C$_1$-C$_{24}$ (hetero)aryl groups.

In a preferred embodiment, the invention relates to a halogenated 1,3-dipole compound according to Formula (2d) or (2e), or their GlcNAc-derived diastereoisomers:

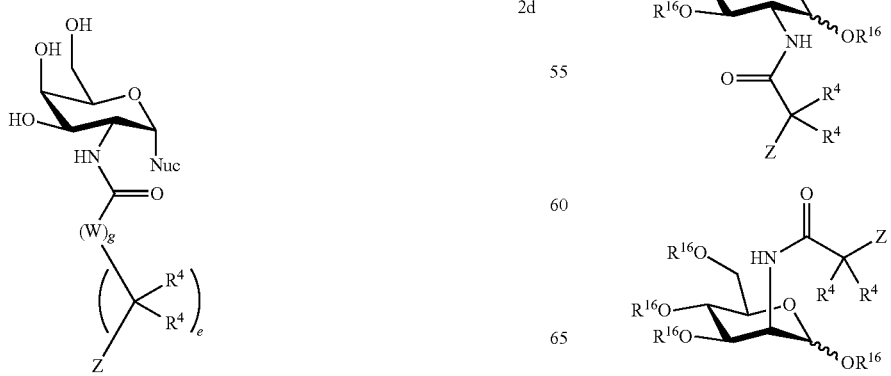

wherein:
W, Z, R$^4$, e and g are as defined above for (2); and
Nuc is selected from the group consisting of a nucleoside monophosphate and a nucleoside diphosphate.

In a preferred embodiment, Nuc is UDP. In a further preferred embodiment, R$^4$ is F, Cl or Br, more preferably F or Cl. Most preferably, R$^4$ is F. It is further preferred that e is 1, 2, 3, 4, 5, 6, 7 or 8, preferably 1, 2, 3, 4, 5 or 6, more preferably 1, 2, 3 or 4, even more preferably 1, 2 or 3, yet even more preferably 1 or 2. In a particularly preferred embodiment, e is 1. It is further preferred that f is 2e, i.e. when e is 4, f is preferably 8, when e is 3, f is preferably 6, when e is 2, f is preferably 4, and when e is 1, f is preferably 2.

Preferably, Z is selected from the group consisting of an azide group, a nitrone group, a diazo group and a nitrile oxide group.

In another preferred embodiment, the invention relates to a halogenated 1,3-dipole compound according to Formula (2f), (2g), (2h) or (2i):

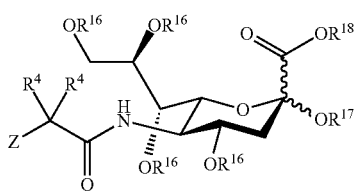

wherein:

$R^4$ and Z are as defined above for (2);

$R^{16}$ and $R^{17}$ are independently selected from the group consisting of hydrogen, $C(O)NR^{18}$, $C(O)R^{18}$ and $C(O)OR^{18}$ wherein $R^{18}$ is as defined below; and $R^{18}$ is selected from the group consisting of $C_1$-$C_{24}$ alkyl groups and $C_1$-$C_{24}$ (hetero)aryl groups.

In a preferred embodiment of (2f), (2g), (2h) or (2i), $R^4$ is F, Cl or Br. More preferably, $R^4$ is F or Cl, and most preferably $R^4$ is F.

Z is a 1,3-dipole functional group. 1,3-Dipole groups are described in more detail above. In a preferred embodiment, Z is a selected from the group consisting of an azide group, a nitrile oxide group, a diazo group and a nitrone group. Preferably, Z is an azide group.

In a further preferred embodiment Z is selected from the group consisting of an azide group, a nitrile oxide group, a diazo group and a nitrone group and $R^4$ is F, Cl or Br. Most preferably, Z is an azide group and $R^4$ is F.

$R^{18}$ is preferably selected from the group consisting of $C_1$-$C_{12}$ alkyl groups and $C_1$-$C_{12}$ (hetero)aryl groups, more preferably from the group consisting of $C_1$-$C_6$ alkyl groups and $C_1$-$C_6$ (hetero)aryl groups. Most preferably $R^{18}$ is methyl, ethyl, n-propyl, i-propyl, n-butyl, t-butyl, phenyl or benzyl.

In a further preferred embodiment, the invention relates to a halogenated 1,3-dipole compound according to formula (2j), (2k), (2l) or (2m):

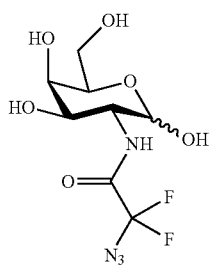

2j

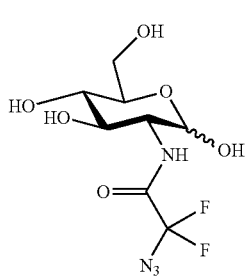

2k

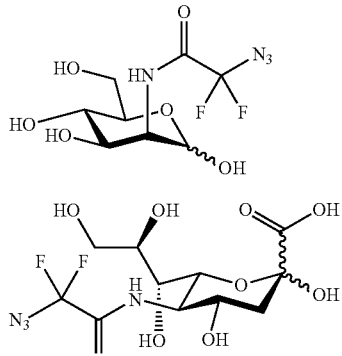

2l

2m

In another further preferred embodiment, the invention relates to a halogenated aliphatic 1,3-dipole compound according to formula (2n), (2o), (2p) or (2q):

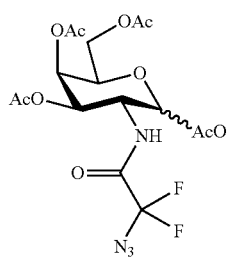

2n

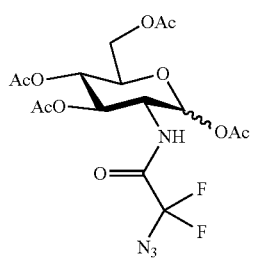

2o

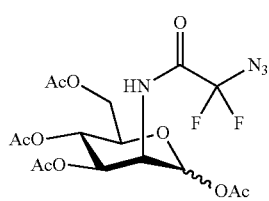

2p

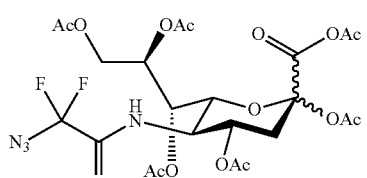

2q

The invention also relates to a compound according to Formula (2v) or (2w), or their GlcNAc-derived diastereoisomers:

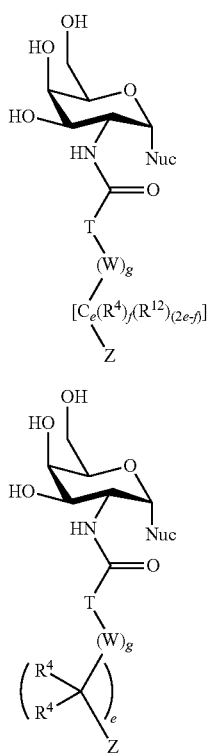

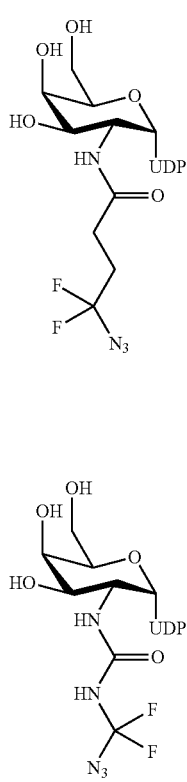

wherein:
Z, W, e, g, $R^{12}$ and $R^4$ are as defined above;
T is O or NH; and
Nuc is a nucleotide.

Preferred embodiments for Z, $R^4$, W, Nuc, g and e are as described above. In a preferred embodiment, Z is selected from the group consisting of an azide group, a nitrile oxide group, a diazo group and a nitrone group. Preferably, Z is an azide group. In a further preferred embodiment Z is selected from the group consisting of an azide group, a nitrile oxide group, a diazo group and a nitrone group, and $R^4$ is F or Cl. More preferably, Z is an azide group and $R^4$ is F or Cl. Most preferably, Z is an azide group and $R^4$ is F. In these embodiments it is further preferred that W, if present, is —$CH_2$—, —$CH_2$—$CH_2$—, —$CH_2$—$CH_2$—$CH_2$— or —$CH_2$—$CH_2$—$CH_2$—$CH_2$—. In these embodiments it is further preferred that T is NH or O, more preferably T is O.

When nucleotide Nuc is UDP, the nucleotide has the structure as shown above.

In a preferred embodiment, the invention relates a compound according to Formula (2x), (2y), (2z), (2za), (2zb) or (2zl), or their GlcNAc-derived diastereoisomers:

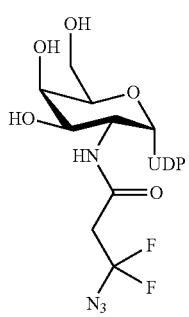

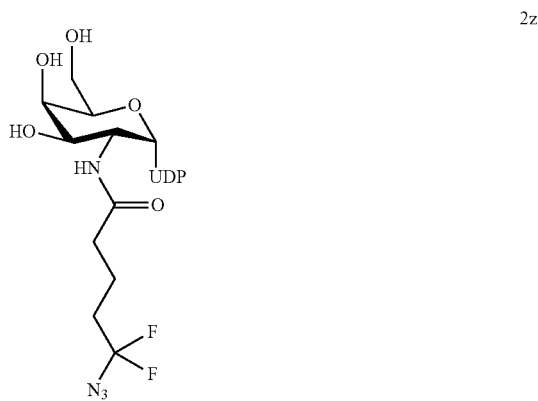

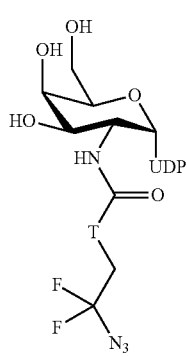

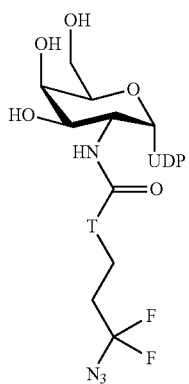
2zb

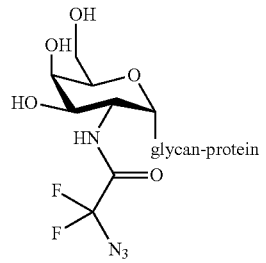
2ze

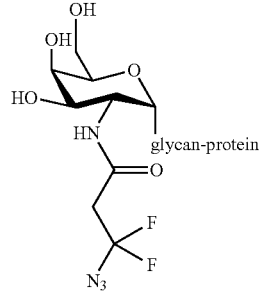
2zf wherein UDP is uridine diphosphate and T is O or NH, preferably O.

In (2x), (2y), (2z), (2za), (2zb) and (2zl) the structure of UDP is as shown above.

The invention further relates to a compound according to Formula (2zc) or (2zd), or their GlcNAc-derived diastereoisomers:

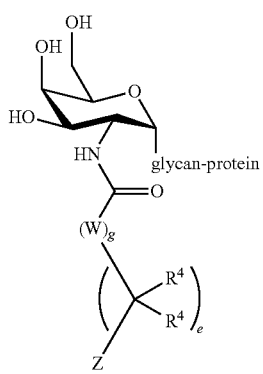
2zc

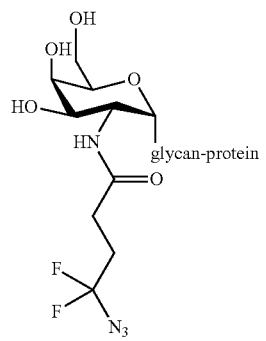
2zg

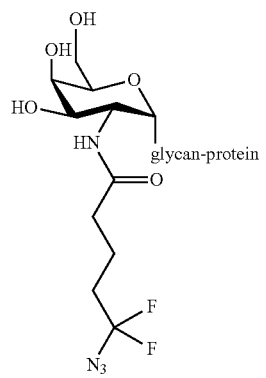
2zh

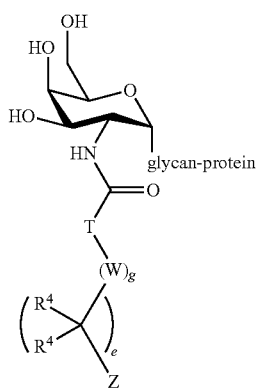
2zd

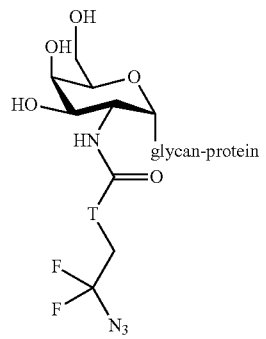
2zi wherein:
T, W, g, Z, $R^4$ and e are as defined above.

In a further preferred embodiment, the compound is according to Formula (2ze), (2zf), (2zg), (2zh), (2zi) or (2zj), or their GlcNAc-derived diastereoisomers:

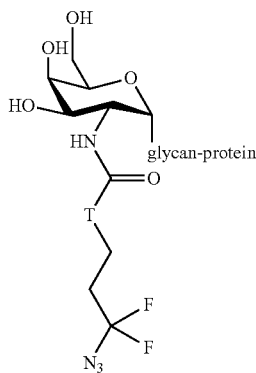

2zj wherein T is O or NH, preferably O.

As described in more detail above, when the halogenated 1,3-dipole is according to Formula (2zc), (2zd), (2ze), (2zf), (2zg), (2zh), (2zi), (2zj) or (2zk), A' is a glycoprotein. When A' is a glycoprotein, it is preferred that the halogenated aliphatic 1,3-dipole functional group is bonded to the glycoprotein via a saccharide moiety of the glycoprotein glycan. In a further preferred embodiment A' is an antibody, and in this embodiment it is further preferred that the halogenated aliphatic 1,3-dipole functional group is bonded to the antibody via a saccharide moiety of the antibody glycan. In these embodiments the halogenated 1,3-dipole functional group is bonded to C2 via the N-acetyl group of a GalNAc moiety, said GalNAc moiety being bonded via C1 to a saccharide moiety of the glycan, preferably to a GlcNAc moiety, more preferably to C4 of said GlcNAc moiety, even more preferably via a β(1,4)-glycosidic bond.

In (2zc), (2zd), (2ze), (2zf), (2zg), (2zh), (2zi), (2zj) and (2zk), the term "glycan" may refer to a monosaccharide moiety, but also to an oligosaccharide moiety. When the term "glycan" refers to a monosaccharide moiety, the monosaccharide moiety is preferably a GlcNAc moiety. When the term "glycan" refers to an oligosaccharide moiety, it is preferred that the saccharide moiety that is connected to C1 of the GalNAc moiety comprising the 1,3-dipole functional group, is a GlcNAc moiety.

Cycloaddition Products

The present invention further relates to a product, obtainable by the process according to the invention. The invention thus relates to a cycloaddition product, obtainable by the process according to the invention.

In a preferred embodiment, the invention relates to a cycloaddition product, obtainable by the cycloaddition of a (hetero)cycloalkyne according to Formula (1) and a halogenated 1,3-dipole compound according to Formula (2), wherein the (hetero)cycloalkyne according to Formula (1) and the halogenated 1,3-dipole compound according to Formula (2) are as defined above.

In a preferred embodiment, the invention therefore relates to a compound according to Formula (13a), (13b), (13c) or (13d):

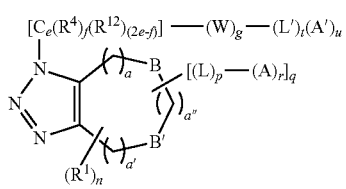

13a

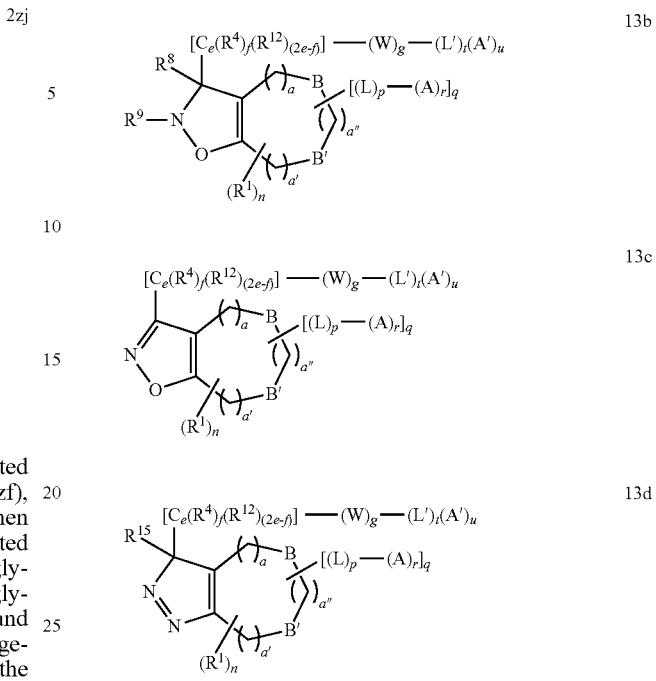

wherein:

$R^1$ n, B, B', a, a', a", L, p, q, r and A are as defined above for (1);

L', A', W, $R^4$, $R^{12}$, W, e, f, g, t, u and m are as defined above for (2); $R^8$ is selected from the group consisting of hydrogen, $C_1$-$C_{12}$ alkyl groups and $(L")_i A"$, wherein L" is as defined for L', A" is as defined for A', i is 0 or 1, wherein L" is selected independently from L' and L'" and wherein A" is selected independently from A' and A'";

$R^9$ is selected from the group consisting of $C_1$-$C_{12}$ alkyl groups and $(L''')_w A'''$, $(L")_i A"$, wherein L" is as defined for L', A" is as defined for A', w is 0 or 1, wherein L" is selected independently from L' and L" and wherein A" is selected independently from A' and A'";

optionally $R^8$ and $R^9$ may together form a (hetero)cycloalkyl group, the (hetero)cycloalkyl group optionally being substituted; and $R^{15}$ is selected from the group consisting of hydrogen, $C_1$-$C_{24}$ alkyl groups, $C_2$-$C_{24}$ (hetero)aryl groups, $C_3$-$C_{24}$ alkyl(hetero)aryl groups, $C_3$-$C_{24}$ (hetero)arylalkyl groups, $C(O)R^{21}$, $C(O)OR^{21}$ and CN (nitrile), wherein $R^{21}$ is selected from the group consisting of $C_1$-$C_{12}$ alkyl groups and $C_2$-$C_{12}$ (hetero)aryl groups, and wherein the alkyl groups, (hetero)aryl groups, alkyl(hetero)aryl groups and (hetero)arylalkyl groups are independently optionally interrupted by one or more hetero-atoms selected from the group consisting of O, N and S, and wherein the alkyl groups, (hetero)aryl groups, alkyl(hetero)aryl groups and (hetero)arylalkyl groups are independently optionally substituted.

In the process according to the invention, when the halogenated 1,3-dipole compound is a diazo compound, an isomer (13m) of compound (13d) may be formed, when $R^{15}$ is hydrogen. The invention therefore further relates to a compound according to Formula (13m):

(13m)

wherein:
R$^1$, n, B, B', a, a', a", L, p, q, r and A are as defined above for (1);
L', A', W, R$^4$, R$^{12}$, W, e, f, g, t, u and m are as defined above for (2); and
R$^{15}$ is hydrogen.

As described above, in the process according to the invention it is preferred that the (hetero)cycloalkyne according to Formula (1) is a (hetero)cyclooctyne. Therefore, in a preferred embodiment of the compound according to Formula (13a), (13b), (13c), (13d) or (13m), a is 0, 1, 2, 3 or 4, a' is 0, 1, 2, 3 or 4 and a" is 0, 1, 2, 3 or 4, with the proviso that a+a'+a"=4, and n is 0-8.

In another preferred embodiment, the invention relates to a cycloaddition product, obtainable by the cycloaddition of a (hetero)cycloalkyne according to Formula (1f) and a halogenated 1,3-dipole compound according to Formula (2), wherein the (hetero)cycloalkyne according to Formula (1f) and the halogenated 1,3-dipole compound according to Formula (2) are as defined above.

The invention therefore also relates to a compound according to Formula (13e), (13f), (13g) or (13h):

(13e)

(13f)

(13g)

(13h)

wherein:
R$^1$, n, B, B', a, a', a", L, p, q, r and A are as defined above for (1f);
L', A', R$^4$, R$^{12}$, e, f, g, t, and u are as defined above for (2);
R$^8$ and R$^9$ are as defined above for (13b); and
R$^{15}$ is as defined above for (13d).

In the process according to the invention, when the halogenated 1,3-dipole compound is a diazo compound, an isomer (13n) of compound (13h) may be formed when R$^{15}$ is hydrogen. The invention therefore further relates to a compound according to Formula (13n):

(13n)

wherein:
R$^1$, n, B, B', a, a', a", L, p, q, r and A are as defined above for (1f);
L', A', W, R$^4$, R$^{12}$, e, f, g, t, and u are as defined above for (2); and
R$^{15}$ is hydrogen.

As described above, in the process according to the invention it is preferred that the (hetero)cycloalkyne according to Formula (1f) is a (hetero)cyclooctyne. Therefore, in a preferred embodiment of the compound according to Formula (13e), (13f), (13g), (13h), or (13n), a is 0, 1 or 2, a' is 0, 1 or 2 and a" is 0, 1 or 2, with the proviso that a+a'+a"=2, and n is 0, 1, 2, 3 or 4.

In another preferred embodiment, the invention relates to a cycloaddition product, obtainable by the cycloaddition of a (hetero)cycloalkyne according to Formula (3) and a halogenated 1,3-dipole compound according to Formula (2), wherein the (hetero)cycloalkyne according to Formula (3) and the halogenated 1,3-dipole compound according to Formula (2) are as defined above.

The invention therefore also relates to a compound according to Formula (13i), (13j), (13k) or (13l):

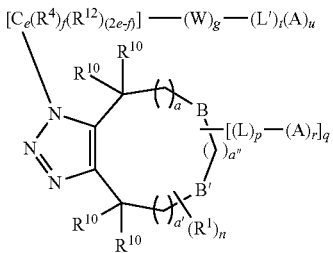

13i

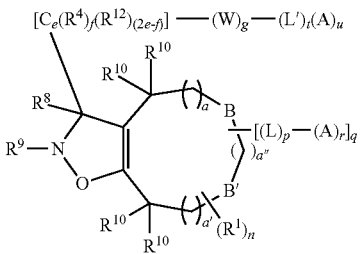

13j

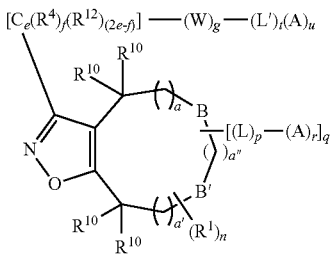

13k

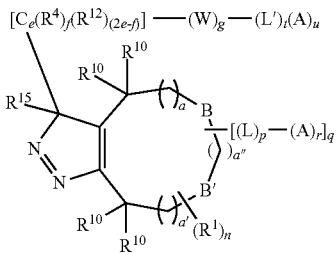

13l wherein:
$R^{10}$, $R^1$, n, B, B', a, a', a", L, p, q, r and A are as defined above for (3);
L', A', $R^4$, $R^{12}$, e, f, g, t, and u are as defined above for (2);
$R^8$ and $R^9$ are as defined above for (13b); and
$R^{15}$ is as defined above for (13d).

In the process according to the invention, when the halogenated 1,3-dipole compound is a diazo compound, an isomer (13o) of compound (13l) may be formed when $R^{15}$ is hydrogen. The invention therefore further relates to a compound according to Formula (13o):

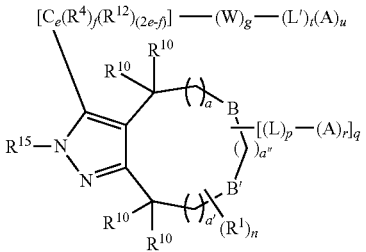

13o wherein:
$R^{10}$, $R^1$, n, B, B', a, a', a", L, p, q, r and A are as defined above for (3);

L', A', $R^4$, $R^{12}$, e, f, g, t, and u are as defined above for (2); and
$R^{15}$ is hydrogen.

As described above, in the process according to the invention it is preferred that the (hetero)cycloalkyne according to Formula (3) is a (hetero)cyclooctyne. Therefore, in a preferred embodiment of the compound according to Formula (13i), (13j), (13k), (13l) or (13o), a is 0, 1 or 2, a' is 0, 1 or 2 and a" is 0, 1 or 2, with the proviso that a+a'+a"=2, and n is 0, 1, 2, 3 or 4.

In another preferred embodiment, the invention relates to a cycloaddition product, obtainable by the cycloaddition of a (hetero)cycloalkyne according to Formula (3b) and a halogenated 1,3-dipole compound according to Formula (2), wherein the (hetero)cycloalkyne according to Formula (3b) and the halogenated 1,3-dipole compound according to Formula (2) are as defined above.

The invention therefore also relates to a compound according to Formula (13p), (13q), (13r) or (13s):

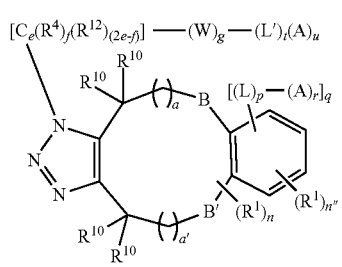

13p

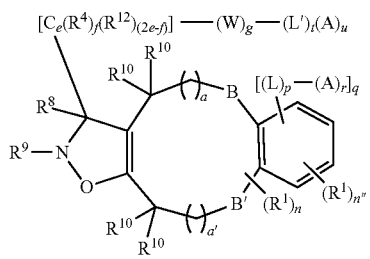

13q

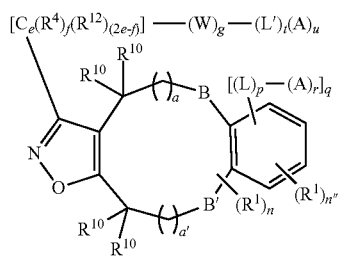

13r

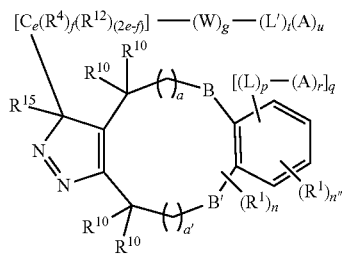

13s wherein:
$R^{10}$, $R^1$, n, B, B', a, a', a", L, p, q, r and A are as defined above for (3);

L', A', $R^4$, $R^{12}$, e, f, g, t, and u are as defined above for (2);
$R^8$ and $R^9$ are as defined above for (13b); and
$R^{15}$ is as defined above for (13d).

In the process according to the invention, when the halogenated 1,3-dipole compound is a diazo compound, an isomer (13t) of compound (13s) may be formed when $R^{15}$ is hydrogen. The invention therefore further relates to a compound according to Formula (13t):

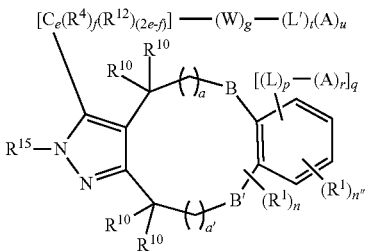

(13t)

wherein:
$R^{10}$, $R^1$, n, B, B', a, a', a", L, p, q, r and A are as defined above for (3);
L', A', $R^4$, $R^{12}$, e, f, g, t, and u are as defined above for (2); and
$R^{15}$ is hydrogen.

As described above, in the process according to the invention it is preferred that the (hetero)cycloalkyne according to Formula (3b) is a (hetero)cyclooctyne. Therefore, in a preferred embodiment of the compound according to Formula (13p), (13q), (13r), (13s), (13t), a+a'+a"=0, i.e. a, a' and a" are 0, and n is 0.

In another preferred embodiment, the invention relates to a cycloaddition product, obtainable by the cycloaddition of a (hetero)cycloalkyne according to Formula (4) and a halogenated 1,3-dipole compound according to Formula (2), wherein the (hetero)cycloalkyne according to Formula (4) and the halogenated 1,3-dipole compound according to Formula (2) are as defined above.

The invention therefore also relates to a compound according to Formula (14a), (14b), (14c) or (14d):

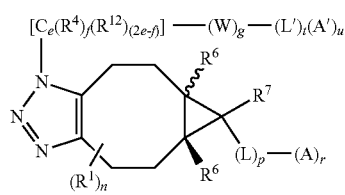

(14a)

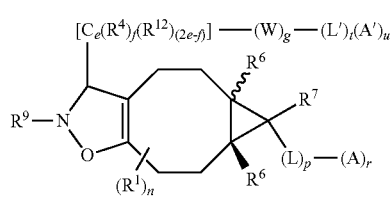

(14b)

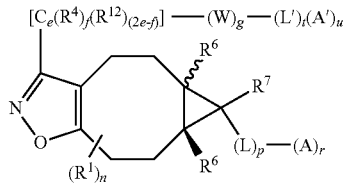

(14c)

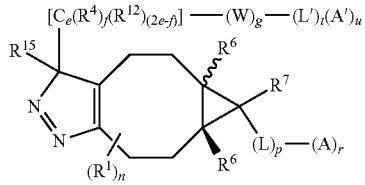

(14d)

wherein:
$R^1$ n, $R^6$, $R^7$, L, p, r and A are as defined above for (4);
L', A', $R^4$, $R^{12}$, e, f, g, t, and u are as defined above for (2);
$R^8$ and $R^9$ are as defined above for (13b); and
$R^{15}$ is as defined above for (13d).

In the process according to the invention, when the halogenated 1,3-dipole compound is a diazo compound, an isomer (14e) of compound (14d) may be formed when $R^{15}$ is hydrogen. The invention therefore further relates to a compound according to Formula (14e):

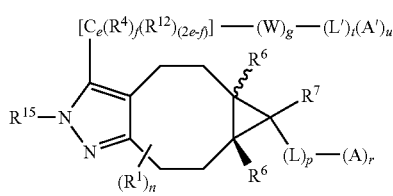

(14e)

wherein:
$R^1$, n, $R^6$, $R^7$, L, p, r and A are as defined above for (4);
L', A', $R^4$, $R^{12}$, e, f, g, t, and u are as defined above for (2); and
$R^{15}$ is hydrogen.

The process according to the invention and the products obtainable by said process have a number of advantages. One particular application of strain-promoted cycloaddition is in the field of metabolic labeling of cell surface glycans with unnatural, azide-bearing monosaccharides, followed by visualization upon treatment with a cyclooctyne-modified reporter molecule. For example, an azide-modified derivative of N-acetylmannosamine (ManNAc) termed N-azidoacetylmannosamine (ManNAz) is metabolized and incorporated into cell surface glycoconjugates, presumably as the corresponding sialic acid (SialNAz). Similarly, it has been shown that N-azidoacetylglucosamine (GlcNAz) and N-azidoacetylgalactosamine (GalNAz) can be tolerated in vitro by the enzymes of the human salvage pathway and that incubation with cell-permeable, peracetylated GlcNAz ($Ac_4$GlcNAz) or GalNAz ($Ac_4$GalNAz) labels proteins in cultured human cells. However, one disadvantage of the current kinetics of strain-promoted cycloaddition between cyclooctynes and azides is the relatively high concentration of cyclooctyne probe (50-100 µM), which may have an adverse effect on cell viability or induce cell death. Hence, azidosugars for metabolic labeling with higher reaction rate constants are highly desirable.

EXAMPLES

Synthesis of Azides

Example 1: Synthesis of ethyl 2-azido-2,2-difluoroacetate (21)

To a solution of ethyl 2-bromo-2,2-difluoroacetate (20) (950 mg, 4.68 mmol) in dry DMSO (5 mL) was added sodium azide (365 mg, 5.62 mmol). After stirring overnight at room temperature, the reaction mixture was poured out into water (150 mL). The layers were separated, dichloromethane was added to the organic layer and the layer was dried over sodium sulfate ($Na_2SO_4$). After filtration, the solvent was removed under reduced pressure (300 mbar) at 35° C. affording the crude product 21 (250 mg, 1.51 mmol, 32%).

$^1$H-NMR (300 MHz, $CDCl_3$): δ 4.41 (q, J=7.2 Hz, 2H), 1.38 (t, J=6.9 Hz, 3H).

Example 1-1. Synthesis of ethyl 3-azido-3,3-difluoropropanoate

To a solution of ethyl 3-bromo-3,3-difluoropropanoate (260 mg, 1.20 mmol) in acetone (1.2 mL) was added sodium azide (117 mg, 1.797 mmol) and the resulting suspension was stirred overnight at r.t. The reaction mixture was diluted with $H_2O$ (3 mL) and extracted with DCM (3×15 mL). The combined organic layers were dried over sodium sulfate, filtered and the solvent was removed under reduced pressure (500 mbar) to afford crude ethyl 3-azido-3,3-difluoropropanoate (174 mg, 0.97 mmol, 81%).

$^1$H-NMR (400 MHz, $CDCl_3$): δ 4.24 (q, J=7.2 Hz, 2H), 3.04 (t, J=11.2 Hz, 2H), 1.30 (t, =7.2 Hz, 3H).

Example 2: Synthesis of 2-azido-N-benzyl-2,2-difluoroacetamide (19a)

Ethyl 2-azido-2,2-difluoroacetate (2l) (48 mg, 0.291 mmol) was dissolved in dichloromethane (4 mL) and benzylamine (32 μL, 0.291 mmol) and $Et_3N$ (60 μL, 0.436 mmol) were added. The reaction was allowed to stir overnight and the solvent was removed under reduced pressure. Flash chromatography (15:1 pentane:EtOAc) afforded the product 19a.

$^1$H-NMR (300 MHz, $CDCl_3$): δ 7.40-7.25 (m, 5H), 4.50 (d, J=5.7 Hz, 2H).

Example 3: Synthesis of 2-azido-N-benzylacetamide (19b)

Azidoacetic acid succinimidyl ester was prepared from azidoacetic acid (22) according to the procedure in Hamilton et al., Chem. Eur. 1, 2012, 18, 2361-2365. Next, azidoacetic acid succinimidyl ester (67 mg, 0.338 mmol) was dissolved in dichloromethane (4 mL) and benzylamine (44 μL, 0.406 mmol) and $Et_3N$ (70 μL, 0.507 mmol) were added. The reaction was allowed to stir overnight and the solvent was removed under reduced pressure. Flash chromatography (1:1-9:1 EtOAc:pentane) afforded the product.

$^1$H-NMR (300 MHz, $CDCl_3$): δ 7.37-7.24 (m, 5H), 4.44 (d, J=5.7 Hz, 2H), 3.97 (s, 2H).

Example 3-1. Synthesis of 3-azido-N-benzyl-3,3-difluoropropanamide (19c)

To a solution of ethyl 3-azido-3,3-difluoropropanoate (174 mg, 0.972 mmol) in THF (1 mL) was added lipase immobilized from *Candida Antarctica* (170 mg) and 9 mL PBS buffer. The reaction mixture was shaken overnight at r.t., filtered and rinsed with THF (2 mL) and $H_2O$ (5 mL). The THF was removed under reduced pressure and the resulting mixture acidified to pH 2. The mixture was then extracted with EtOAc (3×20 mL), the combined organic layers dried over sodium sulfate and concentrated in vacuo. Flash chromatography (3:1-1:3 pentane:EtOAc+0.1% formic acid) afforded 3-azido-N-benzyl-3,3-difluoropropanoic acid (70 mg, 0.46 mmol, 48%). $^1$H-NMR (400 MHz, $CDCl_3$): δ 8.97 (br s, 1H), 3.10 (t, J=11.2 Hz, 2H).

Next, to a solution of 3-azido-3,3-difluoropropanoic acid (50 mg, 0.33 mmol) in dichloromethane (3 mL) were added EDCI (70 mg, 0.364 mmol), DMAP (4 mg, 0.033 mmol) and DIPEA (82 μL, 0.494 mmol). The resulting solution was stirred for 30 min, after which benzylamine (43 μL, 0.396 mmol) was added. The reaction mixture was allowed to stir overnight and DCM (5 mL) was added. The resulting solution was washed with $H_2O$ (2×3 mL), dried over sodium sulfate and the solvent removed under reduced pressure. Flash chromatography (9:1-4:1 pentane:EtOAc) afforded 19c. $^1$H-NMR (400 MHz, $CDCl_3$): δ 7.37-7.28 (m, 5H), 4.48 (d, J=5.6 Hz, 2H), 2.98 (t, J=12 Hz, 2H). LRMS (ESI+) calcd for $C_{10}H_{10}F_2N_4O$ (M+H$^+$) 241.22. found 241.31.

Example 3-2. Synthesis of 2-azido-2,2-difluoroethyl benzylcarbamate (19d)

2-azido-2,2-difluoroacetic acid ethyl ester (21, 100 mg, 0.6 mmol) was suspended in water (2 mL), cooled to 0° C. and $NaBH_4$ (30 mg, 0.8 mmol) was added. After stirring overnight the reaction was quenched with 0.1 M HCl until pH=2 was reached, then NaCl (2 g) was added. DCM (10 mL) was added and the reaction was extracted with DCM (2×10 mL). The combined organic layers were dried over $Na_2SO_4$, filtrated and concentrated under reduced pressure (carefully at 500 mbar) to yield crude 2-azido-2,2-difluoroethanol (41 mg, 0.33 mmol, 56%). $^1$H-NMR (400 MHz, $CDCl_3$): δ 3.84 (t, 2H, J=9.6 Hz).

Next, to a solution of 2-azido-2,2-difluoroethanol (41 mg, 0.33 mmol) in DCM (4 mL) was added CDI (27 mg, 0.17 mmol) and after stirring for 1 h benzylamine (36 μL, 0.33 mmol) was added. The reaction mixture was stirred overnight followed by addition of water (4 mL) and the organic layer was washed with water (2×4 mL), dried over $Na_2SO_4$, filtrated and concentrated under reduced pressure. Purification via flash chromatography (pentane:EtOAc 100:0→5:1) gave the product (19d, 43 mg, 0.17 mmol, 99%). $^1$H-NMR (400 MHz, $CDCl_3$): δ 7.37-7.26 (m, 5H), 5.21 (bs, 1H), 4.41-4.35 (m, 4H).

Figure 3:
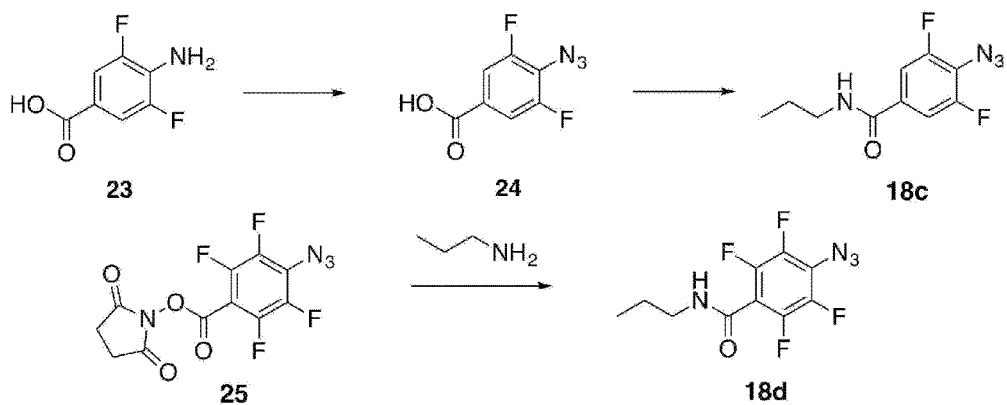
FIG. 3 shows the synthetic scheme for the preparation of azidobenzoyl amide derivatives 18c and 18d (comparative examples).

Example 4: Synthesis of 1-azido-2,6-difluoro-4-(n-propylcarboxamido)benzene (18c), Prepared According to FIG. 3

First, 4-amino-3,5-difluorobenzoic acid (23) was prepared according literature procedure: Bléger et al., J Am. Chem. Soc. 2012, 134, 20597. Then, to a solution of 4-amino-3,5-difluorobenzoic acid (23, 1 g, 4.77 mmol) in TFA (25 mL) was added slowly at 0° C. $NaNO_2$ (658 mg, 9.54 mmol). The mixture was stirred for 1 h at 0° C. $NaN_3$ (3.10 g, 47.7 mmol) was added in small portions to keep the temperature below 5° C. Et₂O (20 mL) was added and the solution was stirred 2 h at rt. The reaction mixture was quenched with H$_2$O (30 mL) and extracted with Et$_2$O. The organic layer was washed with sat. NaCl, dried (Na$_2$SO$_4$), filtered and concentrated in vacuo. The product 24 was used without further purification in the next step.

$^1$H NMR (CDCl$_3$, 400 MHz): δ 7.70-7.63 (m, 2H).

Next, to a solution of 4-azido-3,5-difluorobenzoic acid (24, 250 mg, 1.26 mmol) in THF (10 mL) was added at 0° C. ClCO$_2$iBu (179 mL, 1.38 mmol) and NEt$_3$ (192 mL, 1.38 mmol). The mixture was stirred for 0.5 h at 0° C. A solution of nPrNH$_2$ (155 mL, 1.88 mmol) in THF (2 mL) was added dropwise at 0° C. After stirring for 1 h at 0° C., the mixture was quenched with H$_2$O (20 mL), and extracted with EtOAc (3×30 mL). The organic layer was washed with sat. NaHCO$_3$, dried (Na$_2$SO$_4$), filtered and concentrated in vacuo. The residue was purified by column chromatography (EtOAc/heptane, 1:1) to afford the product (230 mg, 76%) as a white solid.

$^1$H NMR (CDCl$_3$, 400 MHz): δ 7.38-7.32 (m, 2H), 6.10 (bs, 1H), 3.43-3.38 (m, 2H), 1.68-1.59 (m, 2H), 0.99 (t, 3H).

Example 5: Synthesis of 1-azido-2,3,5,6-tetrafluoro-4-(n-propylcarboxamido)benzene (18d)

To a solution of the N-succinimidyl 4-azido-2,3,5,6-tetrafluorobenzoate (25, 250 mg, 0.753 mmol), commercially available from Iris-Biotech, in DCM (5 mL) was added nPrNH$_2$ (620 mL, 7.53 mmol). The mixture was stirred at it for 15 min. The excess nPrNH$_2$ was evaporated, the residue was dissolved in DCM and washed with H$_2$O. The organic layer was dried (Na$_2$SO$_4$), filtered and concentrated in vacuo. The residue was purified by column chromatography (EtOAc/pentane 1:4) to afford the product (173 mg, 83%) as a white solid.

$^1$H NMR (CDCl$_3$, 400 MHz): δ 5.95 (bs, 1H), 3.46-3.41 (m, 2H), 1.69-1.60 (m, 2H), 0.99 (t, 3H).

Figure 11:
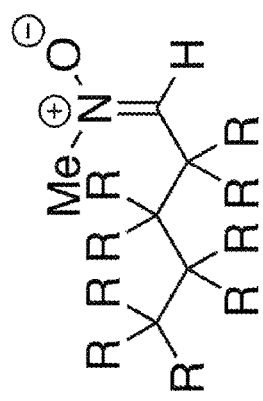
FIG. 11 shows the synthetic route to nitrones 42 and 44 derived from 1-pentanal 41 or perfluoro-1-butanal 43, respectively.
Figure 11:
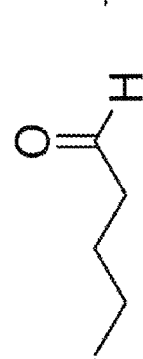
Figure 11:
Figure 11:
Figure 11:
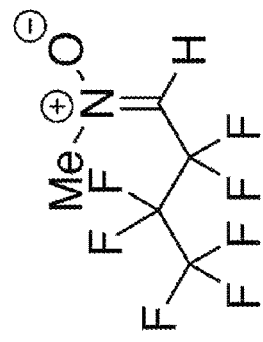
Figure 11:
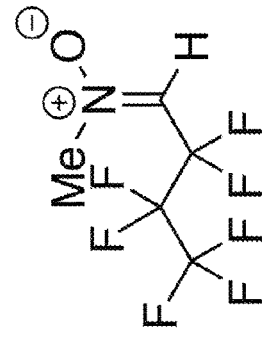

Example 5-1. Synthesis of N-methylpentan-1-imine oxide (42), exemplified in FIG. 11

To a suspension of N-methyl hydroxylamine.HCl (290 mg, 3.5 mmol), NaHCO$_3$ (294 mg, 3.5 mmol) and CaCl$_2$ (971 mg, 8.7 mmol) in Et$_2$O/H$_2$O (1:1, 3 mL each) was added pentanal (41) (185 μL, 1.7 mmol). After stirring for 1 h the reaction was quenched with DCM (10 mL) and water (10 mL) followed by DCM extraction (3×10 mL). The combined organic layers were dried over Na$_2$SO$_4$, filtrated and concentrated under reduced pressure to yield the product (42) in quantitative yield, which was used without further purification. $^1$H-NMR (400 MHz, CDCl$_3$): δ 6.67 (dt, J=0.8 Hz, J=5.6 Hz), 5.31 (q, J=1.6 Hz, 3H), 2.52-2.47 (m, 2H), 1.54-1.47 (m, 2H), 1.41-1.34 (m, 2H), 0.93 (t, J=7.2 Hz, 3H).

Example 5-2. Synthesis of 2,2,3,3,4,4,4-heptafluoro-N-methylbutan-1-imine oxide (44), Exemplified in FIG. 11

To a suspension of N-methyl hydroxylamine.HCl (78 mg, 0.94 mmol), NaHCO$_3$ (98 mg, 1.18 mmol) and NaSO$_4$ in CHCl$_3$ (4 mL) was added heptafluorobutyraldehyde (43, 100 mg, 0.47 mmol)(commercially available as the hydrate form). After stirring for 48 h, the reaction was quenched with DCM (10 mL) and water (10 mL) followed by DCM extraction (2×10 mL). The combined organic layers were dried over Na$_2$SO$_4$, filtrated and concentrated under reduced pressure to yield the product (44, 46 mg, 0.20 mmol, 43%), which was used without further purification. $^1$H-NMR (400 MHz, CDCl$_3$): δ 6.92 (t, J=10 Hz, 1H), 3.90 (t, J=1.6 Hz, 3H).

Example 6: Synthesis of 2-azidogalactose 1-phosphate Derivative (26)

Compound 26 was prepared from D-galactosamine according to the procedure described for D-glucosamine in Linhardt et al., *J. Org. Chem.* 2012, 77, 1449-1456. $^1$H-NMR (300 MHz, CD$_3$OD): δ 5.69 (dd, J=7.2, 3.3 Hz, 1H), 5.43-5.42 (m, 1H), 5.35 (dd, J=11.1, 3.3 Hz, 1H), 4.53 (t, J=7.2 Hz, 1H), 4.21-4.13 (m, 1H), 4.07-4.00 (m, 1H), 3.82 (dt, J=10.8, 2.7 Hz, 1H), 2.12 (s, 3H), 2.00 (s, 3H), 1.99 (s, 3H).

LRMS (ESI−) calcd for C$_{12}$H$_{17}$N$_3$O$_{11}$P (M−H$^+$) 410.06. found 410.00.

Example 7: Synthesis of 2-azidogalactose UDP Derivative (27)

Compound 26 was coupled to UMP according to Baisch et al. *Bioorg. Med. Chem.*, 1997, 5, 383-391.

Thus, a solution of D-uridine-5'-monophosphate disodium salt (1.49 g, 4.05 mmol) in H$_2$O (15 mL) was treated with DOWEX 50W×8 (H$^+$ form) for 30 minutes and filtered. The filtrate was stirred vigorously at room temperature while tributylamine (0.966 mL, 4.05 mmol) was added dropwise. After 30 minutes of further stirring, the reaction mixture was lyophilized and further dried over P$_2$O$_5$ under vacuum for 5 h. The resulting tributylammonium uridine-5'-monophosphate was dissolved in dry DMF (25 mL) in an argon atmosphere. Carbonyldiimidazole (1.38 g, 8.51 mmol) was added and the reaction mixture was stirred at r.t. for 30 min. Next, dry MeOH (180 μL) was added and stirred for 15 min to remove the excess carbonyldiimidazole. The leftover MeOH was removed under high vacuum for 15 min. Subsequently, compound 26 (2.0 g, 4.86 mmol) was dissolved in dry DMF (25 mL) and added dropwise to the reaction mixture. The reaction was allowed to stir at rt for 2 d before concentration in vacuo. The consumption of the imidazole-UMP intermediate was monitored by MS. Flash chromatography (7:2:1-5:2:1 EtOAc:MeOH:H$_2$O) afforded product 27 (1.08 g, 1.51 mmol, 37%).

$^1$H-NMR (300 MHz, D$_2$O): δ 7.96 (d, J=8.0 Hz, 1H), 5.98-5.94 (m, 2H), 5.81-5.79 (m, 1H), 5.70 (dd, J=7.1, 3.3 Hz, 1H), 5.49 (dd, J=15.2, 2.6 Hz, 1H), 5.30 (ddd, J=18.5, 11.0, 3.2 Hz, 2H), 4.57 (q, J=6.0 Hz, 2H), 4.35-4.16 (m, 9H), 4.07-3.95 (m, 2H), 2.17 (s, 3H), 2.08 (s, 3H), 2.07 (s, 3H).

LRMS (ESI−) calcd for C$_{21}$H$_{29}$N$_5$O$_{19}$P$_2$ (M−H$^+$) 716.09. found 716.3.

Example 8: Synthesis of Deacetylated 2-azidogalactose UDP Derivative (28)

Deacetylation was performed according to Kiso et al., *Glycoconj. J.*, 2006, 23, 565. Thus, compound 27 (222 mg, 0.309 mmol) was dissolved in H$_2$O (2.5 mL) and triethylamine (2.5 mL) and MeOH (6 mL) were added. The reaction mixture was stirred for 3 h and then concentrated in vacuo to afford crude UDP-2-azido-2-deoxy-D-galactose (28). $^1$H-NMR (300 MHz, D$_2$O): δ 7.99 (d, J=8.2 Hz, 1H), 6.02-5.98 (m, 2H), 5.73 (dd, J=7.4, 3.4 Hz, 1H), 4.42-4.37 (m, 2H), 4.30-4.18 (m, 4H), 4.14-4.04 (m, 2H), 3.80-3.70 (m, 2H), 3.65-3.58 (m, 1H).

Example 9: Synthesis of UDP-galactosamine (29)

Finally, to a solution of compound 28 in H$_2$O:MeOH 1:1 (4 mL) was added Lindlar's catalyst (50 mg). The reaction was stirred under a hydrogen atmosphere for 5 h and filtered over celite. The filter was rinsed with H$_2$O (10 ml) and the filtrate was concentrated in vacuo to afford the UDP-D-galactosamine (UDP-GalNH$_2$, 29) (169 mg, 0.286 mmol, 92% yield over two steps). $^1$H-NMR (300 MHz, D$_2$O): δ 7.93 (d, J=8.1 Hz, 1H), 5.99-5.90 (m, 2H), 5.76-5.69 (m, 1H), 4.39-4.34 (m, 2H), 4.31-4.17 (m, 5H), 4.05-4.01 (m, 1H), 3.94-3.86 (m, 1H), 3.82-3.70 (m, 3H), 3.30-3.16 (m, 1H). LRMS (ESI−) calcd for C$_{15}$H$_{25}$N$_3$O$_{16}$P$_2$ (M−H$^+$) 564.06. found 564.1.xxx.

Example 10: Synthesis of 4-azido-3,5-difluorobenzoyl Derivative of UDP-GalNH$_2$ (UDP-GalNBAz, 30)

Figure 4:
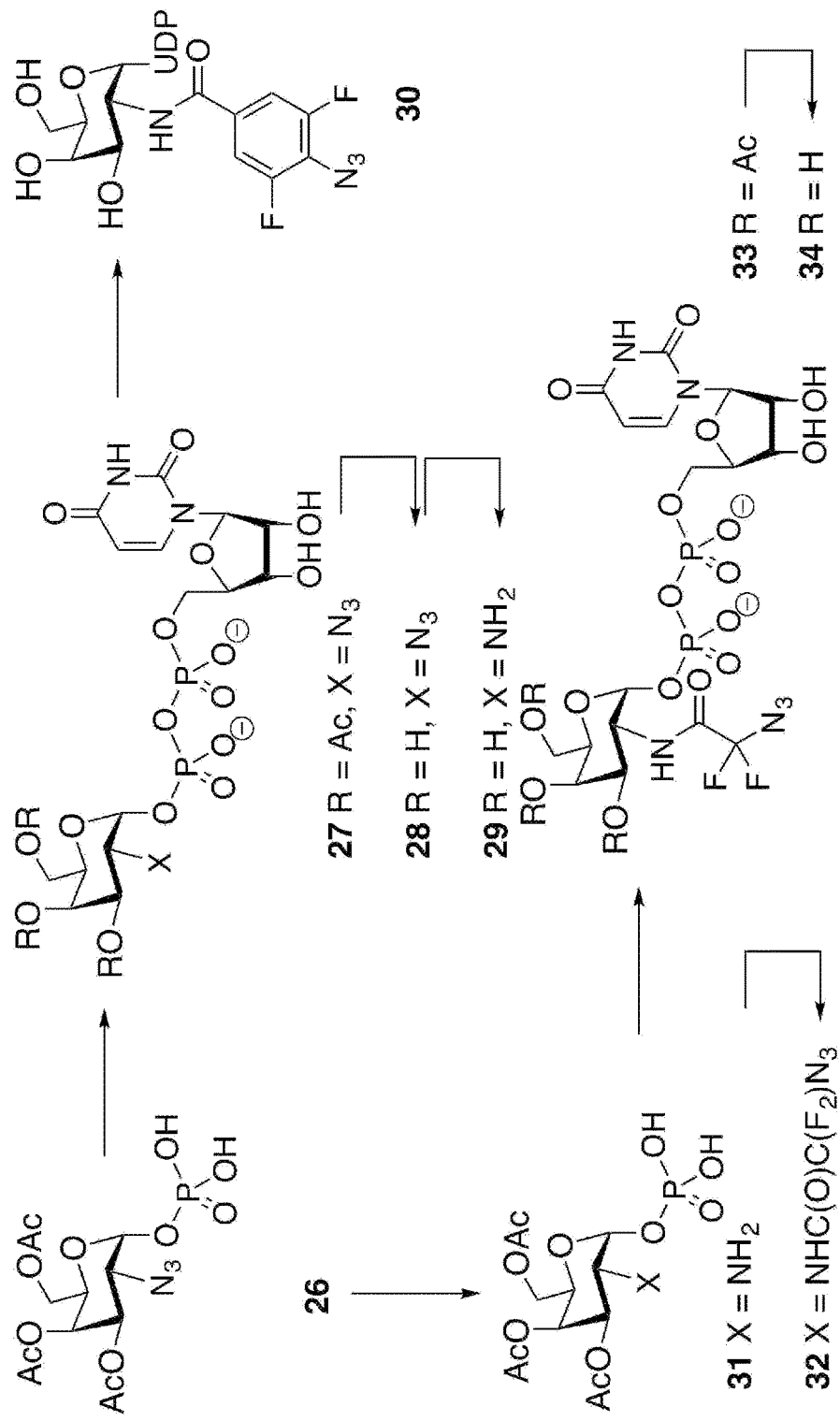
FIG. 4 shows the synthetic scheme for the preparation of UDP-galactose derivatives UDP-F$_2$-GalNBAz (30) and UDP-F$_2$-GalNAz (34).

The synthetic scheme for the preparation of UDP-GalNBAz, (30) is shown in FIG. 4. 4-Azido-3,5-difluorobenzoic acid succinimidyl ester was prepared according to the procedure for pent-4-ynoic acid succinimidyl ester according to Rademann et al., *Angew. Chem. Int. Ed.*, 2012, 51, 9441-9447.

Thus, to a solution of 4-azido-3,5-difluorobenzoic acid 24 was added dicyclohexylcarbodiimide (1.1 equiv) and N-hydroxysuccinimide (1.2 equiv) and the resulting suspension was stirred overnight followed by vacuum filtration. The filtrate was concentrated and dissolved in EtOAc followed by washing with saturated NaHCO$_3$ and brine. The organic layer was dried over Na$_2$SO$_4$, filtrated and concentrated in vacuo to use crude in the next reaction.

$^1$H-NMR (300 MHz, CDCl$_3$): δ 7.74-7.66 (m, 2H), 2.91 (s, 4H).

Next, UDP-GalNH$_2$ (29, 30 mg, 0.0531 mmol) was dissolved in 0.1 M NaHCO$_3$ (0.2 M) and the N-hydroxysuccinimide ester of 4-azido-3,5-difluorobenzoic acid (31 mg, 0.106 mmol, 2 equiv.), dissolved in DMF (0.2 M), was added. The reaction was stirred overnight at r.t. and concentrated in vacuo. Flash chromatography (7:2:1-5:2:1 EtOAc:MeOH:H$_2$O) afforded the product 30 (8 mg, 0.0107 mmol, 20%).

$^1$H-NMR (300 MHz, D$_2$O): δ 7.73 (d, J=8.4 Hz, 1H), 7.52-7.31 (m, 2H), 5.87-5.71 (m, 2H), 5.65-5.57 (m, 1H), 5.47-5.33 (m, 1H), 4.43-3.96 (m, 8H), 3.76-3.60 (m, 2H). LRMS (ESI−) calcd for C$_{22}$H$_{25}$F$_2$N$_6$O$_{17}$P$_2$ (M−H$^+$) 745.07. found 744.9.

Example 11: Synthesis of 2-aminogalactose 1-phosphate Derivative (31)

To a solution of azide 26 (105 mg, 0.255 mmol) in MeOH (3 mL) was added Pd/C (20 mg). The reaction was stirred under a hydrogen atmosphere for 2 h and filtered over celite. The filter was rinsed with MeOH (10 ml) and the filtrate was concentrated in vacuo to afford the free amine 31 (94 mg, 0.244 mmol, 96%).

$^1$H-NMR (300 MHz, D$_2$O): δ 5.87-5.76 (m, 1H), 5.44 (br s, 1H), 5.30-5.20 (m, 1H), 4.55 (t, J=6.3 Hz, 1H), 4.28-4.00 (m, 3H), 2.11 (s, 3H), 2.03 (s, 3H), 2.00 (s, 3H).

LRMS (ESI−) calcd for C$_{12}$H$_{19}$NO$_{11}$P (M−H$^+$) 384.07. found 384.1.

Example 12: Synthesis of 2-azido-2,2-difluoroacetamido Derivative of 2-aminogalactose 1-phosphate (32)

To a solution of amine 31 (94 mg, 0.244 mmol) in dry DMF (3 mL), were added ethyl difluoroazidoacetate 21 (48 mg, 0.293 mmol) and Et$_3$N (68 µL, 0.488 mmol). The reaction was stirred for 6 h, followed by concentration in vacuo to afford the crude product. Flash chromatography (100:0-50:50 EtOAc:MeOH) afforded the product 32 (63 mg, 0.125 mmol, 51%).

$^1$H-NMR (300 MHz, CD$_3$OD): δ 5.64 (m, 1H), 5.47 (d, J=2.4 Hz, 1H), 5.35 (dd, J=11.4, 3.0 Hz, 1H), 4.58-4.48 (m, 2H), 4.25-4.15 (m, 1H), 4.09-4.00 (m, 1H), 2.14 (s, 3H), 2.00 (s, 3H), 1.93 (s, 3H).

LRMS (ESI−) calcd for C$_{14}$H$_{18}$F$_2$N$_4$O$_{12}$P (M−H$^+$) 503.06. found 503.0.

Example 13: Synthesis of Acetylated UDP-2-(2'-azido-2',2'-difluoroacetamido)-galactose (33)

Monophosphate 32 was coupled to UMP according to Baisch et al. *Bioorg. Med. Chem.*, 1997, 5, 383-391).

Thus, a solution of D-uridine-5'-monophosphate disodium salt (98 mg, 0.266 mmol) in H$_2$O (1 mL) was treated with DOWEX 50W×8 (H$^+$ form) for 40 minutes and filtered. The filtrate was stirred vigorously at r.t. while tributylamine (63 µL, 0.266 mmol) was added dropwise. After 30 minutes of further stirring, the reaction mixture was lyophilized and further dried over P$_2$O$_5$ under vacuum for 5 h.

The resulting tributylammonium uridine-5'-monophosphate was dissolved in dry DMF (15 mL) under an argon atmosphere. Carbonyl diimidazole (35 mg, 0.219 mmol) was added and the reaction mixture was stirred at r.t. for 30 min. Next, dry MeOH (4.63 µL) was added and stirred for 15 min to remove the excess carbonyl diimidazole. The leftover MeOH was removed under high vacuum for 15 min. Subsequently, N-methylimidazole, HCl salt (61 mg, 0.52 mmol) was added to the reaction mixture and the monophosphate 32 (63 mg, 0.125 mmol) was dissolved in dry DMF (15 mL) and added dropwise to the reaction mixture. The reaction was allowed to stir at r.t. for o.n. before concentration in vacuo. The consumption of the imidazole-UMP intermediate was monitored by MS. Flash chromatography (7:2:1-5:2:1 EtOAc:MeOH:H$_2$O) afforded the product 33.

$^1$H-NMR (300 MHz, D$_2$O): δ 7.87 (d, J=8.1 Hz, 1H), 5.913-5.85 (m, 2H), 5.67 (dd, J=6.6, 2.7 Hz, 1H), 5.56-5.50 (m, 1H), 5.47-5.43 (m, 1H), 5.31-5.25 (m, 2H), 4.61-4.43 (m, 2H), 4.31-4.05 (m, 5H), 2.16 (s, 3H), 2.02 (s, 3H), 1.94 (s, 3H).

LRMS (ESI−) calcd for C$_{23}$H$_{29}$F$_2$N$_6$O$_{20}$P$_2$ (M−H$^+$) 809.09. found 809.1.

Example 14: Synthesis of UDP-2-(2'-azido-2',2'-difluoroacetamido)-2-deoxy-D-galactose (UDP-diF-GalNAz, 34)

Deacetylation was performed according to Kiso et al., *Glycoconj. J.*, 2006, 23, 565. Thus, compound 33 was dissolved in H$_2$O (1 mL) and triethylamine (1 mL) and MeOH (2.4 mL) were added. The reaction mixture was stirred for 2 h and then concentrated in vacuo. Flash chromatography (7:2:1-5:2:1 EtOAc:MeOH:H$_2$O) afforded UDP-2-(2'-azido-2',2'-difluoroacetamido)-2-deoxy-D-galactose (34).

$^1$H-NMR (300 MHz, D$_2$O): δ 7.86 (d, J=8.1 Hz, 1H), 5.91-5.85 (m, 2H), 5.54 (dd, J=6.6, 3.6 Hz, 1H), 4.31-3.95 (m, 9H), 3.74-3.62 (m, 2H).

LRMS (ESI–) calcd for C$_{17}$H$_{23}$F$_2$N$_6$O$_{17}$P$_2$ (M–H$^+$) 683.06. found 683.10.

Figure 12:
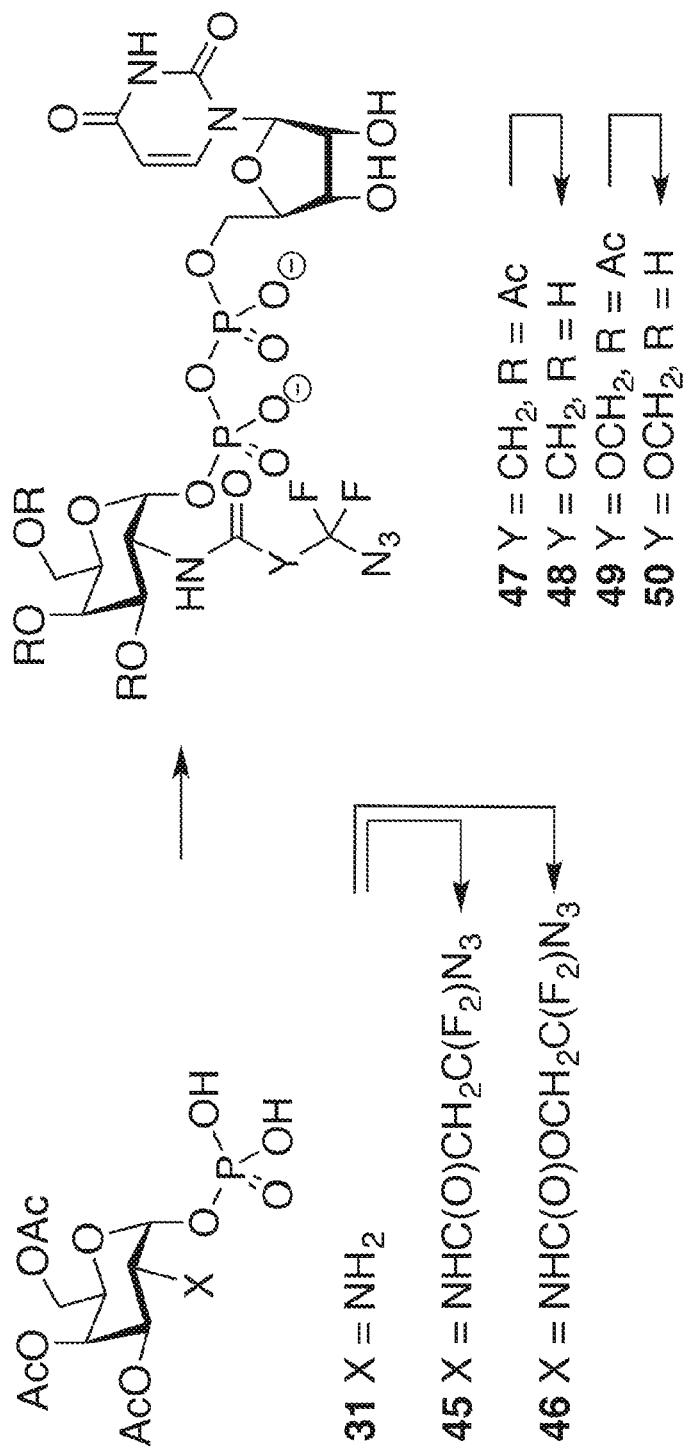
FIG. 12 shows the synthetic scheme for the preparation of UDP-galactosamine derivatives UDP-homo-F$_2$-GalNAz (48) and UDP-F$_2$-carbamate-GalNAz (50).

Example 14-1. Synthesis of 3'-azido-3',3'-difluoropropionyl Derivative of 2-aminogalactose 1-phosphate (45), as Depicted in FIG. 12

To a solution of 3-azido-3,3-difluoropropanoic acid (13 mg, 0.086 mmol) in dry DCM (1 mL) was added p-nitrophenyl chloroformate (14.4 mg, 0.072 mmol) and DIPEA (23.7 µL, 0.143 mmol) and the resulting mixture was stirred for 1 h at r.t. Then, amine 31 (14 mg, 0.0358 mmol) was added and the reaction was allowed to stir overnight at r.t. Additional DIPEA (12 µL, 0.072 mmol) was added and after 3 h, the reaction mixture was quenched with benzylamine (8 µL, 0.072 mmol). The reaction was again stirred overnight and the solvent was removed under reduced pressure.

Purification was performed with a preparative LCMS system (MeCN:H$_2$O+0.1% formic acid) on a Xbridge™ Prep C18, 5 µm OBD™, 30×100 mm column and product 45 (7 mg, 0.014 mmol, 37%).

$^1$H-NMR (400 MHz, CD$_3$OD): δ 5.86 (s, 1H), 5.51-5.38 (m, 1H), 5.29 (d, J=11.6 Hz, 1H), 4.65-4.56 (m, 1H), 4.32-4.18 (m, 2H), 4.15-4.00 (m, 2H), 3.66-3.56 (m, 1H), 2.15 (s, 3H), 2.07 (s, 3H), 2.04 (s, 3H). LRMS (ES$^-$) calcd for C$_{15}$H$_{21}$F$_2$N$_4$O$_{12}$P (M–H$^+$) 517.08. found 517.08.

Example 14-2. Synthesis of UDP-2-N-(3'-azido-3,3'-difluorpropionyl)-2-deoxy-D-galactose (48), as Depicted in FIG. 12

Monophosphate 45 was coupled to UMP according to Baisch et al. *Bioorg. Med. Chem.,* 1997, 5, 383-391).

Thus, tributylammonium uridine-5'-monophosphate (7 mg, 0.014 mmol) was dissolved in dry DMF (0.5 mL) under an argon atmosphere. Carbonyl diimidazole (4.4 mg, 0.027 mmol) was added and the reaction mixture was stirred at r.t. for 30 min. Next, dry MeOH (1 µL) was added and stirred for 15 min to remove the excess CDI. The leftover MeOH was removed under high vacuum for 15 min. Subsequently, N-methylimidazole, HCl salt (8 mg, 0.068 mmol) was added to the reaction mixture and the monophosphate 45 (7 mg, 0.014 mmol) was dissolved in dry DMF (0.5 mL) and added dropwise to the reaction mixture. The reaction was allowed to stir at r.t. overnight. A second amount of tributylammonium uridine-5'-monophosphate was added and the reaction mixture concentrated to approx. 0.5 mL. The resulting solution was again stirred overnight after which the reaction was concentrated in vacuo. Consumption of the imidazole-UMP intermediate was monitored by MS.

The crude compound 47 was deacetylated according to Kiso et al., *Glycoconj.* 1, 2006, 23, 565-573).

Thus, compound 47 was dissolved in H$_2$O (150 µL) and triethylamine (150 µL) and MeOH (350 µL) were added. The reaction mixture was stirred for 2 h and then concentrated in vacuo. Purification was performed with ion-exchange chromatography (Q HITRAP, 1×5 mL columns). First binding on the column was achieved via loading with buffer A (10 mM NH$_4$HCO$_3$) and the column was rinsed with 40 mL buffer A. Next, a gradient of 115 mL to 100% buffer B (250 mM NH$_4$HCO$_3$ was performed to elute the product. The fractions containing the product were freeze-dried to afford a mixture of UMP and the desired product 48. LRMS (ESI–) calcd for C$_{18}$H$_{26}$F$_2$N$_6$O$_{17}$P$_2$ (M–H$^+$) 697.07. found 696.92.

Example 14-3. Synthesis of 2'-azido-2',2'-difluoroethyl carbamate Derivative of 2-galactosamine 1-phosphate (46), as Depicted in FIG. 12

To a solution of 2-azido-2,2-difluoroethanol (149 mg, 1.21 mmol) in DCM (4 mL) was added CDI (98 mg, 0.61 mmol) and after stirring for 1 h, 2-amino-D-galactose 1-phosphate (31, 60 mg, 0.31 mmol) in DMF (4 mL) was added. After stirring overnight the reaction mixture was concentrated and purification using a preparative LCMS system (MeCN:H$_2$O+0.1% formic acid) with a Xbridge™ Prep C18, 5 µm OBD™, 30×100 mm column yielded the product (46, 19 mg, 0.04 mmol, 13%). $^1$H-NMR (400 MHz, CDCl$_3$): δ 5.71-5.69 (m, 1H), 5.49-5.48 (m, 1H), 5.21 (dd, J=3.2 Hz, J=8.4 Hz, 1H), 4.63-4.49 (m, 2H), 4.39-4.31 (m, 1H), 4.26-4.21 (m, 2H), 4.11-4.06 (m, 1H), 2.18 (s, 3H), 2.04 (s, 3H), 1.99 (s, 3H).

Example 14-4. Synthesis of UDP-2-N-(2'-azido-2',2'-difluorethyl carbamate)-2-deoxy-D-galactose (50), as Depicted in FIG. 12

Next, compound 46 was coupled to UMP according to Baisch et al. Bioorg. Med. Chem., 1997, 5, 383-391).

Thus, a solution of D-uridine-5'-monophosphate disodium salt (1.49 g, 4.05 mmol) in H$_2$O (15 mL) was treated with DOWEX 50W×8 (H+ form) for 30 minutes and filtered. The filtrate was stirred vigorously at rt while tributylamine (0.966 mL, 4.05 mmol) was added dropwise. After 30 minutes of further stirring, the reaction mixture was lyophilized.

The resulting tributylammonium uridine-5'-monophosphate (21 mg, 0.04 mmol) was dissolved in dry DMF (1 mL) in an argon atmosphere. Carbonyldiimidazole (11 mg, 0.08 mmol) was added and the reaction mixture was stirred at r.t. for 30 min. Next, dry MeOH (1.6 µL) was added and stirred for 15 min to remove the excess CDI. The leftover MeOH was removed under high vacuum for 15 min. Subsequently, compound 46 (19 mg, 0.036 mmol) and N-methylimidazole HCl (25 mg, 0.18 mmol) were dissolved in dry DMF (1 mL) and added dropwise to the reaction mixture. The reaction was allowed to stir overnight before concentration in vacuo. Subsequent the crude mixture was dissolved in a mixture of water:MeOH:Et$_3$N (3:7:3, 2 mL) and stirred until full protection was achieved according to LCMS. The reaction was concentrated under reduced pressure and purified on anion exchange column (Q HITRAP, 1×5 mL columns). First binding on the column was achieved via loading with buffer A (10 mM NaHCO$_3$) and the column was rinsed with 40 mL buffer A. Next a gradient to 25% B (250 mM NaHCO$_3$) was performed to elute the product. The fractions containing the product were freeze-dried to afford the product 50 (15 mg, 0.02 mmol, 58%). LRMS (ESI–) calcd for C$_{18}$H$_{25}$F$_2$N$_6$O$_{18}$P$_2$ (M) 713.07. found 713.4. $^1$H-NMR (400 MHz, D$_2$O): δ 7.85 (d, J=8.0 Hz, 1H), 5.87-5.84 (m, 2H), 5.49 (dd, J=3.2 Hz, J=4 Hz, 1H), 4.44-4.07 (m, 7H), 3.92-3.81 (m, 3H), 3.66-3.63 (m, 2H).

Example 15: Competition Experiment of Between 2-azido-N-benzyl-2,2-difluoroacetamide (19a) and 2-azido-N-benzylacetamide (19b) with BCN—OH (35)

First, 2-azido-N-benzylacetamide (19b) (10.0 mg, 0.044 mmol) and 2-azido-N-benzyl-2,2-difluoroacetamide (19a) (8.4 mg, 0.044 mmol) were dissolved in CD$_3$CN (815 µL) and D$_2$O (407 µL) was added. Next, BCN—OH (35) (1.33 mg, 0.0088 mmol, 0.2 equiv. With respect to each azide) was dissolved in CD$_3$CN:D$_2$O 2:1 and added to the reaction mixture. After 2 h, the solvent was removed under reduced pressure, the crude product was dissolved in CDCl$_3$ and an $^1$H-NMR spectrum was measured to determine the ratio of the formed products 36 and 37. $^1$H-NMR (300 MHz, CDCl$_3$): δ 7.42-7.23 (m, 11H), 7.18-7.14 (m, 0.11H), 6.69 (br s, 1H), 6.61 (br s, 1H), 4.95 (s, 0.10H), 4.62 (d, J=6.0 Hz, 0.25H), 4.50 (d, J=5.7 Hz, 2H), 4.46 (d, J=6.0 Hz, 2H), 4.39 (dd, J=6.0, 3.3 Hz, 0.1H), 4.02 (s, 2H), 3.78-3.65 (m), 3.24-2.82 (m), 2.35-2.19 (m), 1.78-1.52 (m), 1.40-1.05 (m), 1.04-0.79 (m).

Example 15-1. Competition Experiment Between 3-azido-N-benzyl-3,3-difluoropropanamide (19c) and 2-azido-N-benzylacetamide (19b) with BCN—OH (35)

2-Azido-N-benzylacetamide 19b (1.85 mg, 9.70 µmol) and 3-azido-N-benzyl-3,3-difluoropropanamide 19c (2.33 mg, 9.70 µmol) were dissolved in CD$_3$CN:D$_2$O 2:1 (400 µL). Next, BCN—OH 35 (0.292 mg, 1.95 µmol) was dissolved in 200 µL CD$_3$CN:D$_2$O 2:1 and added to the reaction. The resulting solution was allowed to stir o.n. at r.t., and concentrated in vacuo. The residue was taken up in CDCl$_3$ (700 µL) and an $^1$H-NMR experiment was performed to check the ratio of the two formed triazole products, which indicated an approx. 2:1 ratio of the triazole product resulting from 19c with 35 versus 36 (the triazole product resulting from 19b with 35).

$^1$H-NMR (400 MHz, CDCl$_3$): δ 7.38-7.27 (m, 11H), 4.97 (d, J=2 Hz, 0.15H), 4.48 (d, J=3.6 Hz, 3.69H), 4.43 (d, J=2.4 Hz, 0.38H), 4.40 (d, J=5.2 Hz, 0.20H), 4.05 (s, 1.82H), 3.79 (t, J=13.2 Hz, 0.28H), 3.74-3.65 (m, 0.51H). The region of the spectrum at higher field remains undefined due to overlapping peaks. MS showed the presence of the two clicked products: LRMS (ESI+) calcd for C$_{20}$H$_{24}$F$_2$N$_4$O$_2$ (M+H$^+$) 391.19. found 391.12 (triazole product resulting from 19c with 35), and calcd for C$_{19}$H$_{24}$N$_4$O$_2$ (M+H$^+$) 341.20. found 341.19 (36).

Mass Spectral Analysis of Monoclonal Antibodies by Reduction

A solution of 50 µg (modified) IgG, 1 M Tris-HCl pH 8.0, 1 mM EDTA and 30 mM DTT in a total volume of approximately 70 µL was incubated for 20 minutes at 37° C. to reduce the disulfide bridges allowing to analyze both light and heavy chain. If present, azide-functionalities are reduced to amines under these conditions. Reduced samples were washed trice with milliQ using an Amicon Ultra-0.5, Ultracel-10 Membrane (Millipore) and concentrated to 10 µM (modified) IgG. The reduced IgG was analyzed by electrospray ionization time-of-flight (ESI-TOF) on a JEOL AccuTOF. Deconvoluted spectra were obtained using Magtran software.

Mass Spectral Analysis of Monoclonal Antibodies by Treatment with Fabricator™

A solution of 20 µg (modified) IgG was incubated for 1 hour at 37° C. with fabricator (commercially available from Genovis, Lund, Sweden) (1.25 U/µL) in phosphate-buffered saline (PBS) pH 6.6 in a total volume of 10 µL. Fabricator-digested samples were washed trice with milliQ using an Amicon Ultra-0.5, Ultracel-10 Membrane (Millipore) resulting in a final sample volume of approximately 40 µL. The Fc/2 fragment was analyzed by electrospray ionization time-of-flight (ESI-TOF) on a JEOL AccuTOF. Deconvoluted spectra were obtained using Magtran software.

Example 16: Preparation of Deglycosylated (Trimmed) Trastuzumab by Endo S Treatment Glycan trimming of trastuzumab (38) was performed with endo S from *Streptococcus pyogenes* (commercially available from Genovis, Lund, Sweden). Thus, trastuzumab (10 mg/mL) was incubated with endo S (40 U/mL) in 25 mM Tris pH 8.0 for approximately 16 hours at 37° C. The deglycosylated (i.e. trimmed) IgG was concentrated and washed with 10 mM MnCl$_2$ and 25 mM Tris-HCl pH 8.0 using an Amicon Ultra-0.5, Ultracel-10 Membrane (Millipore).

After deconvolution of peaks, the mass spectrum showed one peak of the light chain and two peaks of the heavy chain. The two peaks of heavy chain belonged to one major product (49496 Da, 90% of total heavy chain), resulting from core GlcNAc(Fuc) substituted trastuzumab, and a minor product (49351 Da, ±10% of total heavy chain), resulting from deglycosylated trastuzumab.

Protocol for Glycosyltransfer of Galactosamine Derivative UDP-GalNAz or 34 with Gal-T1(Y289L)

Enzymatic introduction of UDP-GalNAz or 34 onto deglycosylated (herein also referred to as trimmed) trastuzumab was effected with a mutant of bovine β(1,4)-galactosyltransferase [β(1,4)-Gal-T1(Y289L)]. The deglycosylated trastuzumab (10 mg/mL) was incubated with the appropriate UDP-galactose derivative (0.4 mM) and β(1,4)-Gal-T1(Y289L) (1 mg/mL) in 10 mM MnCl$_2$ and 25 mM Tris-HCl pH 8.0 for 16 hours at 30° C.

Next, the functionalized trastuzumab was incubated with protein A agarose (40 µL per mg IgG) for 2 hours at 4° C. The protein A agarose was washed three times with PBS and the IgG was eluted with 100 mM glycine-HCl pH 2.7. The eluted IgG was neutralized with 1 M Tris-HCl pH 8.0 and concentrated and washed with PBS using an Amicon Ultra-0.5, Ultracel-10 Membrane (Millipore) to a concentration of 15-20 mg/mL.

Said mutant of bovine β(1,4)-galactosyltransferase [Gal-T1(Y289L)] is the catalytic domain consisting of residues 130-402 of a mutant of bovine β(1,4)-galactosyltransferase [β(1,4)-Gal-T1] with the Y289L and C342T mutations. GalT(Y289L) was expressed, isolated and refolded from inclusion bodies according to the reported procedure by Qasba et al. (*Prot. Expr. Pur.* 2003, 30, 219-76229, incorporated by reference herein).

Example 17: Preparation of Trastuzumab-(GalNAz) 39

Trimmed trastuzumab was subjected to the glycosyltransfer protocol with [β(1,4)-Gal-T1(Y289L)] and UDP-N-azidoacetylgalactosamine (UDP-GalNAz, (Carbosynth, Compton, Berkshire, UK)). After protein A affinity purification, mass spectral analysis indicated the formation of a one major product of (49713 Da, 90% of total heavy chain), resulting from GalNAz transfer to core GlcNAc(Fuc) substituted trastuzumab, and a minor product (49566 Da, ±10% of total heavy chain), resulting from GalNAz transfer to core GlcNAc substituted trastuzumab.

Example 18: Preparation of Trastuzumab-(F$_2$-GalNAz) 40

Deglycosylated (trimmed) trastuzumab was subjected to the glycosyltransfer protocol with bovine β(1,4)-galactosyltransferase [β(1,4)-Gal-T1(Y289L)] and UDP-F$_2$-GalNAz 34 as substrate. After reduction with DTT, mass spectral analysis indicated the formation of one major heavy chain product (49865 Da, approximately 90% of total heavy chain), resulting from F$_2$-GalNAz transfer to core GlcNAc(Fuc)-substituted trastuzumab which has reacted with DTT during sample preparation.

Example 19: Preparation of Trastuzumab-(F$_2$-GalNBAz)

Figure 8:
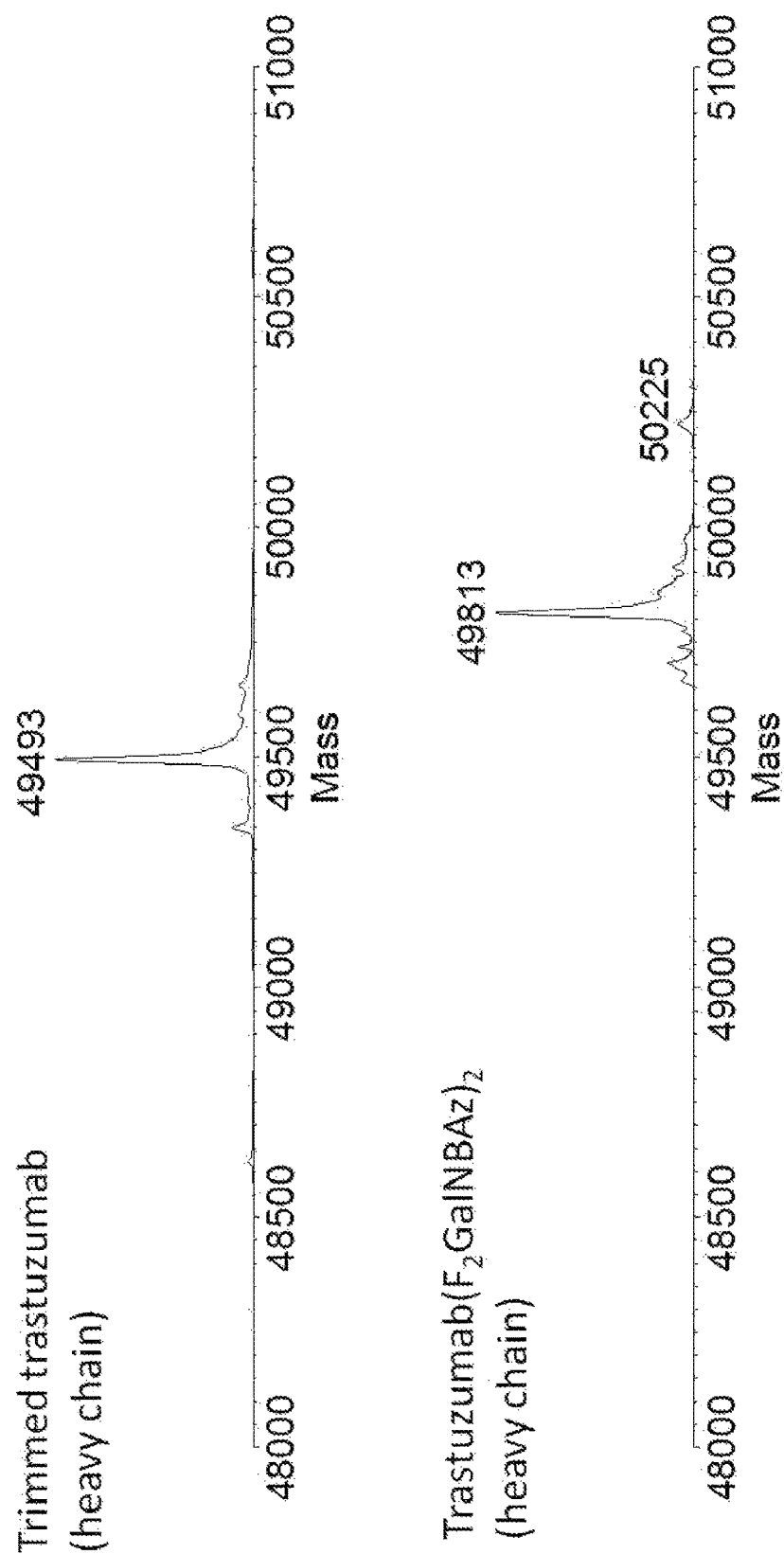
FIG. 8 shows the mass spectral profile of the trastuzumab heavy chain after deglycosylation (top spectrum) and after GalT-induced introduction of azidosugar F$_z$-GalNBAz (comparative example).

Trimmed trastuzumab (10 mg/mL, 6.6 nmol), obtained by Endo S treatment of trastuzumab, was incubated with UDP-F$_2$GalNBAz (30, 7 mM) and β(1,4)-Gal-T1(Y289L) (2 mg/mL) in 10 mM MnCl$_2$ and 25 mM Tris-HCl pH 8.0 at 30° C. overnight. Mass spectral analysis of the reduced sample indicated the formation of a one major product (49813 Da, approximately 90% of total heavy chain), resulting from F$_2$GalNBAz transfer to core GlcNAc(Fuc) substituted trastuzumab heavy chain. FIG. 8 shows the heavy chain of trimmed trastuzumab (upper spectrum) and the heavy chain of trastuzumab conjugated to F$_2$GalNBAz (lower spectrum).

Example 19-1. Preparation of Trastuzumab Derivative 51

Trimmed trastuzumab (10 mg/mL, 13 nmol), obtained by Endo S treatment of trastuzumab, was incubated with 48 (1 mM) and [β(1,4)-Gal-T1(Y289L)] (0.9 mg/mL) in 10 mM MnCl$_2$ and 25 mM Tris-HCl pH 7.5 at 30° C. overnight. Spectral analysis after digestion with Fabricator™ (50 U in 10 μL Tris pH 6.6) and subsequent wash with MiliQ using an Amicon Ultra-0.5, Ultracel-10 Membrane (Millipore) indicated the formation of a one major product (24449 Da, expected mass 24449), resulting from transfer of 2-N-(3'-azido-3',3'-difluorpropionyl)-2-deoxy-D-galactose from 48 to core GlcNAc(Fuc) substituted trastuzumab heavy chain.

Example 19-2. Preparation of Trastuzumab Derivative 52

Trimmed trastuzumab (4 mg/mL, 13 nmol), obtained by Endo S treatment of trastuzumab, was incubated with 50 (0.75 mM) and [β(1,4)-Gal-T1(Y289L)] (0.63 mg/mL) in 8 mM MnCl$_2$ and 25 mM Tris-HCl pH 7.5 at 30° C. overnight. Spectral analysis after digestion with Fabricator™ (50 U in 10 μL Tris pH 6.6) and subsequent wash with MiliQ using an Amicon Ultra-0.5, Ultracel-10 Membrane (Millipore) indicated the formation of a one major product (24432 Da, expected mass 24433), resulting from transfer of 2-N-(2'-azido-2',2'-difluorethyl carbamate)-2-deoxy-D-galactose from 50 to core GlcNAc(Fuc) substituted trastuzumab heavy chain.

Example 20: Conjugation of Trast-(GalNAz)$_2$ 39 and Trast-(F$_2$-GalNAz)$_2$ 40 with BCN-PEG$_{2000}$ at Variable IgG Concentrations

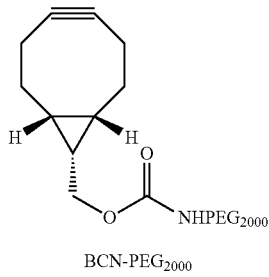

BCN-PEG$_{2000}$

Figure 9:
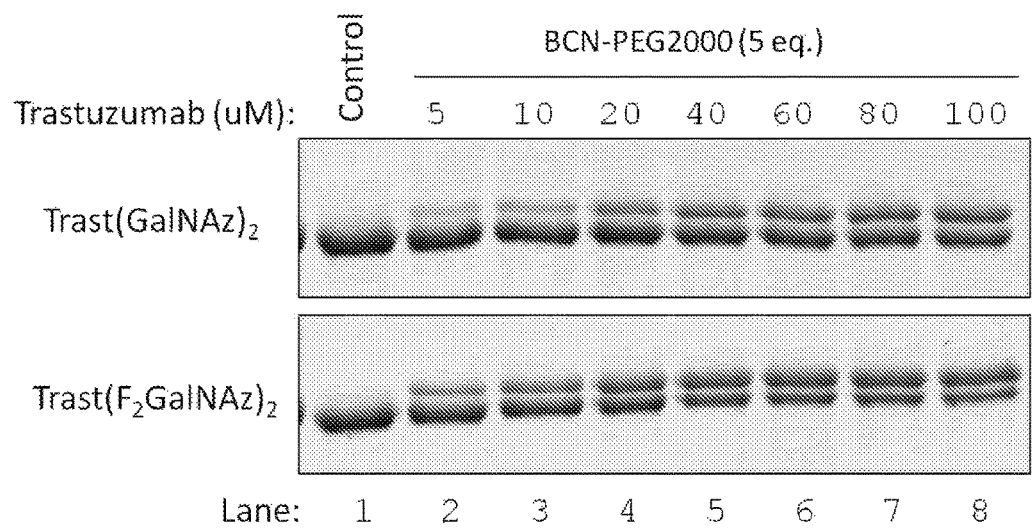
FIG. 9 shows the SDS-PAGE of the heavy chain of deglycosylated azido-derivative of trastuzumab 39 (trast-(GalNAz)$_2$) and 40 (trast-(F$_2$-GalNAz)$_2$) before conjugation to BCN-PEG$_{2000}$ (lower band) and after conjugation to BCN-PEG$_{2000}$ (upper band). Trastuzumab that has not been incubated with BCN-PEG$_{2000}$ was used as a negative control (lane 1).

A dilution series of either trast(GalNAz)$_2$ (39) or trast(F$_2$-GalNAz)$_2$ (40) (5, 10, 20, 40 60, 80 and 100 μM) in PBS was incubated overnight at room temperature with 5 equivalents of BCN-PEG$_{2000}$ (SynAffix B.V., Oss, the Netherlands) (25, 50, 100, 200, 300, 400 and 500 Reaction products were analyzed through reduced SDS-PAGE gel followed by coomassie staining. FIG. 9 shows the SDS-PAGE of the heavy chain of deglycosylated azido-derivative of trastuzumab 39 (trast-(GalNAz)$_2$) and 40 (trast-(F$_2$-GalNAz)$_2$) before conjugation to BCN-PEG$_{2000}$ (lower band) and after conjugation to BCN-PEG$_{2000}$ (upper band). Trastuzumab which has not been incubated with BCN-PEG$_{2000}$ was used as a negative control (lane 1). Trast(GalNAz)$_2$ 39 shows approximately 50% conversion at an IgG concentration of 100 μM (upper panel, lane 8) while trast(F$_2$-GalNAz)$_2$ 40 shows approximately 50% conversion at an IgG concentration of 40 μM (lower panel, lane 5).

Example 21: Conjugation of Trast-(GalNAz)$_2$ 39 and Trast(F$_2$-GalNAz)$_2$ 40 with BCN-PEG$_{2000}$ at Variable Concentrations of BCN-PEG$_{2000}$ Trast-(GalNAz)$_2$ (39) and trast-(F$_2$-GalNAz)$_2$ (40) (10 μM IgG) in PBS was incubated overnight at room temperature with 0 to 20 equivalents of BCN-PEG$_{2000}$ (0 to 200 Reaction products were separated by reducing SDS-PAGE followed by coomassie staining.

Figure 10:
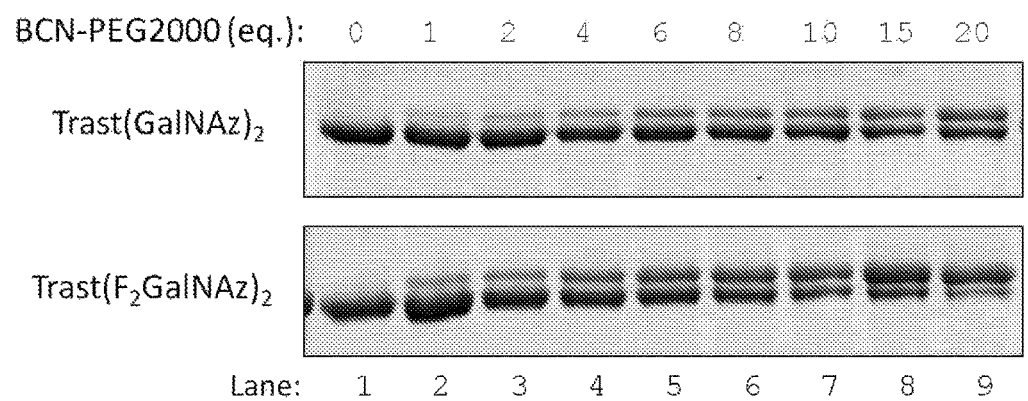
FIG. 10 shows the SDS-PAGE of the heavy chain of trastuzumab 39 (trast-(GalNAz)$_2$) and 40 (trast-(F$_2$-GalNAz)$_2$) before conjugation to BCN-PEG$_{2000}$ (lower band) and after conjugation to BCN-PEG$_{2000}$ (upper band).

FIG. 10 shows the heavy chain of trastuzumab 39 (trast-(GalNAz)$_2$) and 40 (trast-(F$_2$-GalNAz)$_2$) before conjugation to BCN-PEG$_{2000}$ (lower band) and after conjugation to BCN-PEG$_{2000}$ (upper band). Trast-(GalNAz)$_2$ shows less than 50% conversion when incubated with 20 equivalents BCN-PEG$_{2000}$ (upper panel, lane 9) while trast-(F$_2$-GalNAz)$_2$ shows approximately 50% conversion when incubated with only 8 equivalents BCN-PEG$_{2000}$ (lower panel, lane 6).

Example 22: Competition Experiment Between Trastuzumab Derivative 39 (Trast-GalNAz) and Trastuzumab Carbamate Derivative 52 with BCN-Biotin

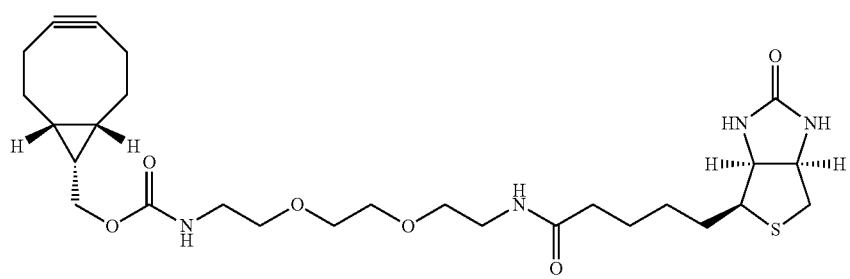

BCN-biotin

To a mixture of 39 and 52 (5 mg/mL each, 0.1 mL each) in 25 mM Tris-HCl pH 7.5 was added BCN-biotin (SynAffix B.V., Oss, the Netherlands) (6 μL, 0.2 mM) and the reaction was incubated overnight at room temperature. Spectral analysis after digestion with Fabricator™ (50 U in 10 μL Tris pH 6.6) and subsequent wash with MiliQ using an Amicon Ultra-0.5, Ultracel-10 Membrane (Millipore) showed the formation of both triazole products (masses 24933 and 25000, expected masses 24933 and 25000) in a ratio of 2:1 in favour of the triazole product resulting from the reaction of 52 with BCN-biotin versus the triazole product resulting from the reaction of 39 with BCN-biotin.

Example 23: Synthesis of 4-(((1R,8S,9s)-bicyclo [6.1.0]non-4-yn-9-ylmethyl (4-oxo-4-((pyren-1-ylm-ethyl)amino)butyl)carbamate (BCN-pyrene)

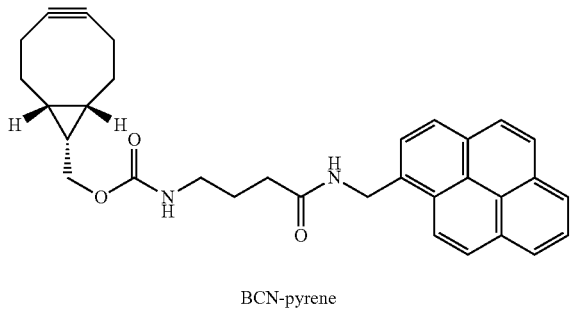 [SMILES: O=C(CCCNC(=O)OC[C@@H]1[C@@H]2CCC#CCC[C@@H]21)NCc1ccc2ccc3cccc4ccc1c2c34]

BCN-pyrene 4-((((1R,8S,9s)-bicyclo[6.1.0]non-4-yn-9-ylmethoxy) carbonyl)amino)butanoic acid (260 mg, 0.69 mmol) was dissolved in DCM (7 mL) followed by the addition of 1-aminomethyl pyrene HCl (221 mg, 0.83 mmol) and Et$_3$N (143 μL, 1 mmol). The reaction was stirred overnight followed by the addition of water (10 mL) and DCM (10 mL). The organic layer was subsequent washed with saturated aqueous NaHCO$_3$ solution (10 mL) and 0.1 M HCl (10 mL), dried over Na$_2$SO$_4$, filtrated and concentrated under reduced pressure. Purification via flash chromatography (pentane:EtOAc 1:3→1:8) gave the product BCN-pyrene (227 mg, 0.46 mmol, 67%). $^1$H-NMR (400 MHz, CDCl$_3$): δ 8.26-7.95 (m, 9H), 6.34 (bs, 1H), 5.14 (d, J=5.2 Hz, 2H), 4.96 (bs, 1H), 4.05 (d, J=8 Hz, 2H), 3.24-3.19 (m, 2H), 2.28-2.14 (m, 6H), 1.86 (q, J=7.2 Hz, 2H), 1.65-1.62 (m, 1H), 1.53-1.48 (m, 2H), 1.29-1.23 (m, 2H), 0.89-0.85 (m, 2H).

Example 24: Reaction Rate Comparison for Azides (19a, b and d) with BCN-Pyrene

In a sample jar 40 μL BCN-pyrene stock (10 mM in DMF) was added to 440 μL MeCN and subsequently H$_2$O (320 μL) and a stock solution of azide 19a, 19b, or 19d (200 μL of 10 mM azide in MeCN) were added (final concentration 0.4 mM BCN-pyrene, 2 mM azide, approximately 5-fold excess of azide). The reaction was incubated at room temperature and at indicated time points HPLC measurements (Phenomenex Luna 5u C18 column and H$_2$O/MeOH+0.1% TFA as eluens) were performed. The intensity of the peaks of the product and starting material at 340 nm were used to calculate the conversion.

TABLE 2

Time-dependent conversion of BCN-pyrene upon incubation with excess (5 equiv.) of azide 19a, 19b or 19d.

| Time (min) | 19a | 19b | 19d |
|---|---|---|---|
| 15 | 25% | 49% | 53% |
| 35 | 40% | 73% | 72% |
| 75 | 64% | 95% | 92% |

From Table 2, it becomes clear that both fluorinated azides 19b and 19d display an approximately 1.8 times accelerated reaction rate for cycloaddition with BCN-pyrene with respect to regular azide 19a.

Example 25: Reaction Speed Comparison for Azides (19a and 19b) with Cyclooctyne

In a sample jar 50 μL cyclooctyne stock (100 mM in DMF) was added to 533 μL MeCN and subsequently H$_2$O (316 μL) and a stock solution of azide 19a or 19b (100 μL of 10 mM azide in MeCN) were added (final concentration 5 mM cyclooctyne, 1 mM azide, approximately 5-fold excess of cyclooctyne). The reaction was incubated at room temperature and at indicated time points LCMS measurements (Xbridge™ C18, with H$_2$O/MeCN+0.1% TFA as eluens) were performed. The intensity of the peaks of the product and starting material at 254 nm were used to calculate the conversion.

TABLE 3

Time-dependent conversion of azide 19a or 19b upon incubation with excess cyclooctyne.

| Time (min) | 19a | 19b |
|---|---|---|
| 50 | 13% | 57% |
| 150 | 32% | 78% |

From Table 3, it becomes clear that fluorinated azide 19b displays an approximately 3 times accelerated reaction rate for cycloaddition with cyclooctyne with respect to regular azide 19a.

Example 26: Reaction Speed Comparison for Nitrones (42a-b) with BCN-Pyrene

In a sample jar, a solution of BCN-pyrene (40 μL of a 10 mM stock solution in DMF) was added to MeCN (440 μL) and subsequently, H$_2$O (320 μL) and a solution of nitrone (200 μL of a 10 mM stock solution in MeCN) were added (final concentration 0.4 mM BCN-pyrene, 2 mM nitrone, approximately 5-fold excess of nitrone). The reaction was incubated at room temperature and at indicated time points HPLC measurements (Phenomenex Luna 5u C18 column and H$_2$O/MeOH+0.1% TFA as eluens) were performed. The intensity of the peaks of the product and starting material at 340 nm were used to calculate the conversion.

TABLE 4

Time-dependent conversion of BCN-pyrene upon incubation with excess (5 equiv.) of nitrone 42 or 44.

| Time (min) | 42 | 44 |
|---|---|---|
| 15 | 0% | 91% |
| 120 | 1% | 100% |

From Table 4, it becomes clear that fluorinated nitrone 44 displays at least a 50-fold accelerated reaction rate for cycloaddition with BCN-pyrene with respect to regular nitrone 42.

Example 27: Synthesis of Cyclooctyne

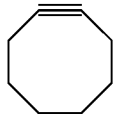

Synthesis according to procedure described in: L. Brandsma, H. D. Verkruijsse, *Synthesis*, 1978, 290, incorporated by reference herein.

The invention claimed is:

1. A process comprising reacting a halogenated 1,3-dipole compound with a (hetero)cyclooctyne, wherein the halogenated 1,3-dipole compound is defined according to Formula (2):

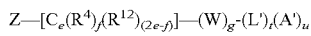

wherein:
t is 1;
u is 1-4;
Z is a 1,3-dipole functional group;
L' is a linker;
A' is a glycoprotein or an, optionally substituted, saccharide moiety;
$R^4$ is independently selected from the group consisting of F, Cl, Br and I and $-C_yR^{13}_{(2y+1)}$, wherein y is 1-6 and $R^{13}$ is selected from the group consisting of F, Cl, Br and I;
$R^{12}$ is independently selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, and wherein the alkyl groups, cycloalkyl groups, (hetero)aryl groups, alkyl(hetero)aryl groups and (hetero)arylalkyl groups are optionally interrupted by one or more heteroatoms selected from the group consisting of O, S and N;
e is 1-10;
f is 1-2e;
g is 0 or 1; and
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N, wherein the 1,3-dipole functional group is bonded to an $sp^3$ C-atom, and at least one of the one or more substituents $R^4$ is bonded to that same $sp^3$ C-atom;
and wherein the (hetero)cyclooctyne is according to Formula (1):

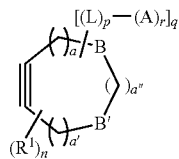

wherein:
a is 0, 1, 2, 3 or 4;
a' is 0, 1, 2, 3 or 4;
a" is 0, 1, 2, 3 or 4;
with the proviso that a+a'+a"=4;
n is 0-8;
$R^1$ is independently selected from the group consisting of oxo, halogen, $-OR^2$, $-NO^2$, $-CN$, $-S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl (hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein R2 is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when n is 2 or more, two $R^1$ groups may together form a (hetero)aryl group, the (hetero)aryl group optionally being substituted with an $(L)_p$-$(A)_r$ substituent;
p is 0 or 1;
r is 1-4;
L is a linker;
A is independently selected from the group consisting of D, E or Q, wherein D, E and Q are as defined below;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or n is 2 or more and two $R^1$ groups together form a (hetero)aryl group wherein the (hetero)aryl group is substituted with an $(L)_p$-$(A)_r$ substituent;
D is a molecule of interest;
E is a solid surface; and
Q is a functional group.

2. The process according to claim 1, wherein the molecule of interest is selected from the group consisting of a reporter molecule, a diagnostic compound, an active substance, an enzyme, an amino acid, a (non-catalytic) protein, a peptide, a polypeptide, an oligonucleotide, a monosaccharide, an oligosaccharide, a polysaccharide, a glycan, a (poly)ethylene glycol diamine, a polyethylene glycol chain, a polyethylene oxide chain, a polypropylene glycol chain, a polypropylene oxide chain and a 1,x-diaminoalkane, wherein x is the number of carbon atoms in the alkane.

3. The process according to claim 1, wherein the solid surface is selected from the group consisting of a functional surface, a nanomaterial, a carbon nanotube, a fullerene, a virus capsid, a metal surface, a metal alloy surface and a polymer surface.

4. The process according to claim 1, wherein Q is a functional group independently selected from the group consisting of hydrogen, halogen, $R^{11}$, —CH=C($R^{11}$)$_2$, —C≡C$R^{11}$, —[C($R^{11}$)$_2$C($R^{11}$)$_2$O]$_q$$R^{11}$ wherein q is in the range of 1 to 200, —CN, —N$_3$, —NCX, —XCN, —X$R^{11}$, —N($R^{11}$)$_2$, —+N($R^{11}$)$_3$, —C(X)N($R^{11}$)$_2$, —C($R^{11}$)$_2$X$R^{11}$, —C(X)$R^{11}$, —C(X)X$R^{11}$, —S(O)$R^{11}$, —S(O)$_2$$R^{11}$, —S(O)O$R^{11}$, —S(O)$_2$O$R^{11}$, —S(O)N($R^{11}$)$_2$, —S(O)$_2$N($R^{11}$)$_2$, —OS(O)$R^{11}$, —OS(O)$_2$$R^{11}$, —OS(O)O$R^{11}$, —OS(O)$_2$O$R^{11}$, —P(O)($R^{11}$)(O$R^{11}$), —P(O)(O$R^{11}$)$_2$, —OP(O)(O$R^{11}$)$_2$, —Si($R^{11}$)$_3$, —XC(X)$R^{11}$, —XC(X)X$R^{11}$, —XC(X)N($R^{11}$)$_2$, —N($R^{11}$)C(X)$R^{11}$, —N($R^{11}$)C(X)X$R^{11}$ and —N($R^{11}$)C(X)N($R^{11}$)$_2$, wherein X is oxygen or sulphur and wherein $R^{11}$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O and N.

5. The process according to claim 1, wherein the halogenated aliphatic 1,3-dipole compound is selected from the group consisting of a halogenated aliphatic nitrone compound, a halogenated aliphatic azide compound, a halogenated aliphatic diazo compound, a halogenated aliphatic nitrile oxide compound, a halogenated aliphatic nitronate compound, a halogenated aliphatic nitrile imine compound, a halogenated aliphatic sydnone compound, a halogenated aliphatic sulfon hydrazide compound, a halogenated aliphatic pyridine oxide compound, a halogenated aliphatic oxadiazole 1-oxide compound, a halogenated aliphatic dipole resulting from deprotonation of an alkylated pyridinium compound, a halogenated aliphatic [1,2,3]triazol-8-ium-1-ide compound, a halogenated aliphatic 1,2,3-oxadiazol-3-ium-5-olate compound and a halogenated aliphatic 5-oxopyrazolidin-2-ium-1-ide compound.

6. The process according to claim 1, wherein Z is selected from the group consisting of an azide group, a nitrone group, a nitrile oxide group and a diazo group.

7. The process according to claim 1, wherein the halogenated 1,3-dipole is according to the Formula (2a):

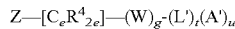

wherein:
Z, L', A', $R^4$, W, g, e, t and u are as defined in claim 1.

8. The process according to claim 1, wherein A' is independently selected from the group consisting of a reporter molecule, an active substance, an enzyme, a protein, a glycoprotein, an antibody, a peptide, a polypeptide, an oligonucleotide, a monosaccharide, an oligosaccharide, a polysaccharide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane wherein x is the number of carbon atoms in the alkane.

9. The process according to claim 1, wherein A' is an N-acetylglucosamine (GlcNAc) moiety or an N-acetylgalactosamine (GalNAc) moiety, the GlcNAc moiety and GalNAc moiety optionally being substituted.

10. The process according to claim 1, wherein A' is a glycoprotein and wherein the halogenated 1,3-dipole functional group is bonded to the glycoprotein via a saccharide moiety of the glycoprotein glycan.

11. The process according to claim 1, wherein the glycoprotein is an antibody.

12. The process according to claim 1, wherein the halogenated 1,3-dipole compound is according to Formula (2zc) or (2zd), or their GlcNAc-derived diastereoisomers:

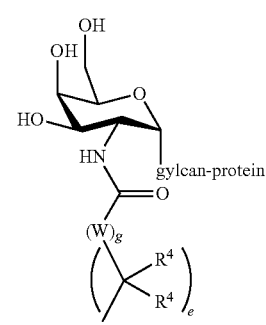

2zc

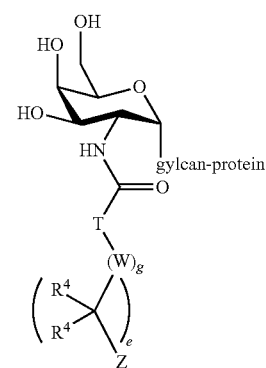

2zd wherein:
W, g, Z, $R^4$ and e are as defined in claim 1; and
T is O or NH.

13. The process according to claim 1, wherein the 1,3-halogenated dipole compound is according to Formula (2ze), (2zf), (2zg), (2zh), (2zi), (2zj) or (2zk), or their GlcNAc-derived diastereoisomers:

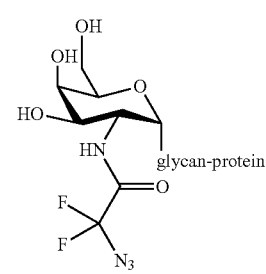

2ze

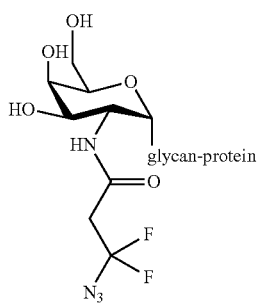
2zf
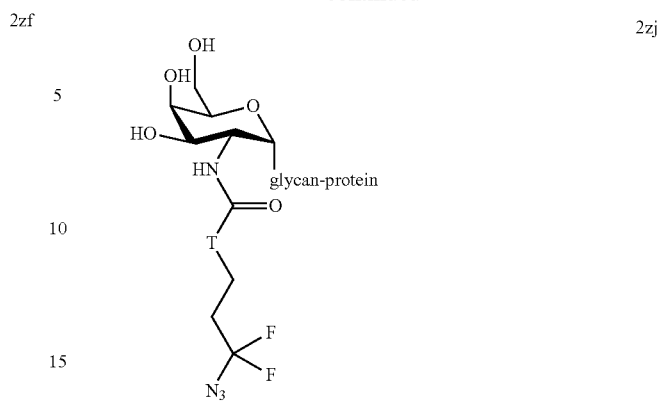
2zj
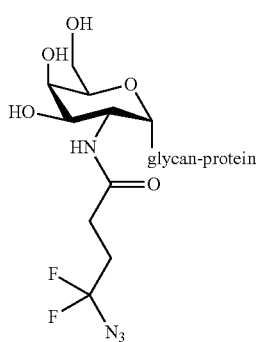
2zg
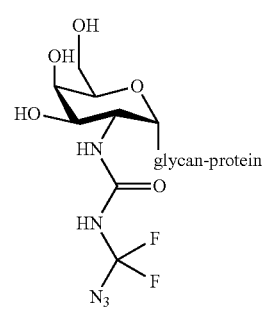
2zk
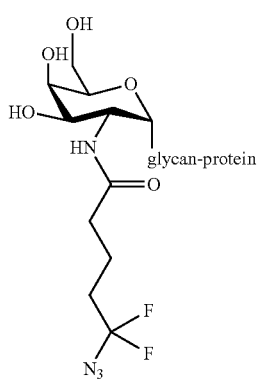
2zh
wherein T is O or NH.
14. The process according to claim 1, wherein the (hetero)cyclooctyne is according to Formula (4), (5), (6), (7), (8), (9), (10), (11) or (12):
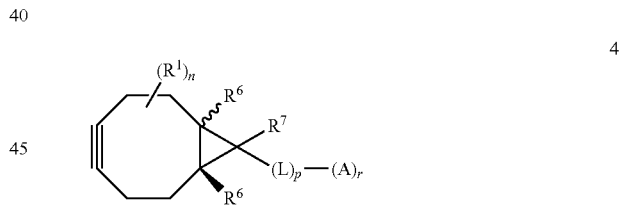
4
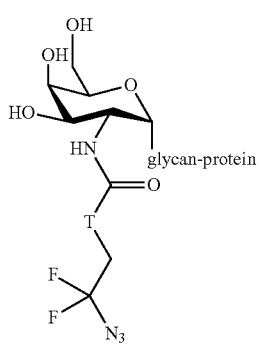
2zi
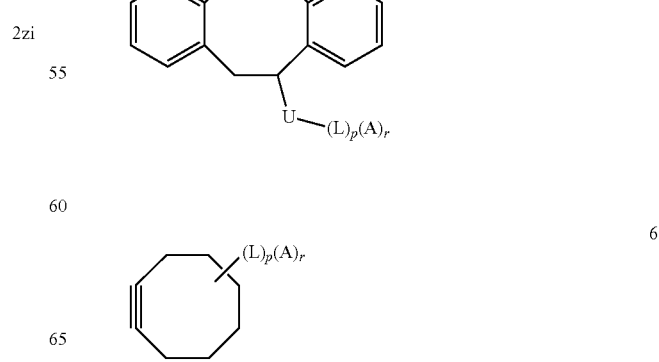
5
6

-continued

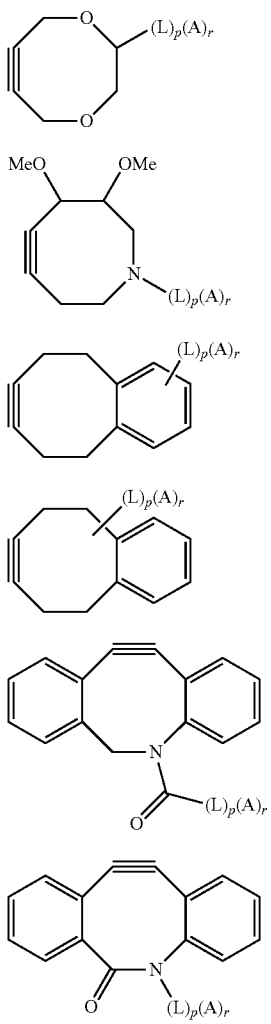

wherein:
L, p, r and A are as defined in claim 1;
U is O, S or $NR^{19}$, wherein $R^{19}$ is selected from the group consisting of hydrogen and $C_1$-$C_{24}$ alkyl groups;
n is 0-8;
$R^6$ is independently selected from the group consisting of hydrogen, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and
$R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted.

15. The process according to claim 1, wherein A and/or A' is independently selected from the group consisting of a reporter molecule, an active substance, a solid surface, an enzyme, a protein, a glycoprotein, an antibody, a peptide, a polypeptide, an oligonucleotide, a saccharide, an oligosaccharide, a polysaccharide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane).

* * * * *